US006956026B2

(12) United States Patent
Beeley et al.

(10) Patent No.: US 6,956,026 B2
(45) Date of Patent: Oct. 18, 2005

(54) USE OF EXENDINS FOR THE REDUCTION OF FOOD INTAKE

(75) Inventors: Nigel Robert Arnold Beeley, Solana Beach, CA (US); Sunil Bhavsar, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/003,869

(22) Filed: Jan. 7, 1998

(65) Prior Publication Data

US 2002/0137666 A1 Sep. 26, 2002

Related U.S. Application Data

(60) Provisional application No. 60/065,442, filed on Nov. 14, 1997, provisional application No. 60/066,029, filed on Nov. 14, 1997, provisional application No. 60/055,404, filed on Aug. 8, 1997, and provisional application No. 60/034,905, filed on Jan. 7, 1997.

(51) Int. Cl.$^7$ .......................... A61K 38/00; A61K 37/18
(52) U.S. Cl. ............................ 514/12; 514/2; 530/300; 530/324; 424/185.1
(58) Field of Search ...................... 514/2, 12; 530/300, 530/324; 424/185.1

(56) References Cited

U.S. PATENT DOCUMENTS

| | | | |
|---|---|---|---|
| 5,118,666 A | 6/1992 | Habener | 514/12 |
| 5,120,712 A | 6/1992 | Habener | 514/12 |
| 5,424,286 A | * 6/1995 | Eng | 514/2 |
| 5,512,549 A | 4/1996 | Chen | 514/12 |
| 5,545,618 A | 8/1996 | Buckley | 514/12 |
| 5,574,008 A | 11/1996 | Johnson | 514/12 |
| 5,686,511 A | 11/1997 | Bobo | 523/412 |
| 6,191,102 B1 | 2/2001 | DiMarchi et al. | 514/2 |

FOREIGN PATENT DOCUMENTS

| | | |
|---|---|---|
| AU | 199731732 B2 | 6/1997 |
| WO | WO 9011296 | 4/1990 |
| WO | WO 9111457 | 8/1991 |
| WO | WO 9318786 | 9/1993 |
| WO | WO 9325579 | 12/1993 |
| WO | WO 96/40196 | * 12/1996 |
| WO | WO 97/46584 | 12/1997 |
| WO | WO 98/05351 A1 | 2/1998 |
| WO | WO 98/19698 A1 | 5/1998 |
| WO | WO-9830231 A1 | * 7/1998 |
| WO | WO 98/30231 A1 | 7/1998 |
| WO | WO 99/07404 A1 | 2/1999 |

OTHER PUBLICATIONS

Goldstone et al., FEBS Letters, vol. 415, No. 2, Sep. 29, 1997, pp. 134–138.*
Navarro et al., Journal of Neurochemistry, vol. 67, No. 5, pp. 1982–1991, 1996.*
Turton et al., Nature, vol. 379, pp. 69–72, 1996.*
Goldstone et al, FEBS Letters, vol. 415, pp. 134–138, 1997.*
Adelhorst, K., et al., "Structure–activity studies of glucagon–like peptide–1 (GLP–1)," *J. Biol. Chem.*, 269(9):6275–8 (1994).
Bartlett, et al, "Inhibition of Chymotrypsin by Phosphonate and Phosphonamidate Peptide Analogs," *Bioorg. Chem.*, 14:356–377 (1986).
Bhavsar, "Inhibition of gastric emptying and of food intake appear to be independently controlled in rodents," *Soc. Neurosci. Abst.*, 21:460 (188.8) (1995).
Cohen, et al, *The Pico Tag Method: A Manual of Advanced Techniques for Amino Acid Analysis*, pp. 11–52, Millipore Corporation (1989).
D'Alessio et al. "Elimination of the Action of glucagon–like Peptide 1 Causes an Impairment of glucose tolerance after Nutrient Ingestion by Healthy Baboons," *J. Clin. Invest.*, 97:133–38 1996.
Eissele et al. "Rat Gastric somatostatin and Gastrin Release: Interactions of Exendin–4 and Truncated Glucagon–Like Peptide–1 (GLP–1)Amide," *Life Sci.*, 55:629–34 1994.
Eng et al. "Isolation and Characterization of Exendin–4, and Exendin–3 Analogue, from *Heloderma suspectum* Venom", *J. Biol. Chem.*, 267:7402–05 1992.
Eng et al. "Purification and Structure of Exendin–3, a New Pancreatic Secretagogue Isolated from *Heloderma horridum* Venom," *J. Biol. Chem.*, 265:20259–62 1990.
Fehmann et al. "Stable Expression of the Rat GLP–1 Receptor in CHO Cells: Activation and Binding Characteristics Utilizing GLP–I(7–36)–Amide, Oxyntomodulin, Extendin–4, and Exendin(9–39)," *Peptides*, 15(3):453–6 1994.
Ferguson et al. "Cell–Surface Anchoring of Proteins Via Glycosylphosphatidylinositol Structures," *Annu. Rev. Biochem.* 57:285–320 (1988).
Goke et al. "Exendin–4 Is a High Potency Agonist and Truncated Exendin–(9–39)–amide an Antagonist at the Glucagon–like Peptide 1–(7–36)–amide Receptor of Insulin–secreting β–Cells," *J. Biol. Chem.*, 268:19650–55 1993.
Halaas, J.L., et al., "Weight–Reducing Effects of the Plasma Protein Encoded by the obese Gene," *Science*, 269:543–546 1995.

(Continued)

Primary Examiner—Jon Weber
Assistant Examiner—Abdel A. Mohamed
(74) Attorney, Agent, or Firm—Arnold & Porter, LLP

(57) ABSTRACT

Methods for treating conditions or disorders which can be alleviated by reducing food intake are disclosed which comprise administration of an effective amount of an exendin or an exendin agonist, alone or in conjunction with other compounds or compositions that affect satiety. The methods are useful for treating conditions or disorders, including obesity, Type II diabetes, eating disorders, and insulin-resistance syndrome. The methods are also useful for lowering the plasma glucose level, lowering the plasma lipid level, reducing the cardiac risk, reducing the appetite, and reducing the weight of subjects. Pharmaceutical compositions for use in the methods of the invention are also disclosed.

68 Claims, 11 Drawing Sheets

OTHER PUBLICATIONS

Kodama, J., et al, "Effect of Captopril on Glucose Concentration Possible Role of Augmented Postprandial Forearm Blood Flow," *Diabetes Cares,* 13(11):1109–1111 (1990).

Kolligs, et al, "Reduction of the incretin effect in rats by the glucagon–like peptide–1 receptor antagonist exendin (9–39) amide," *Diabetes,* 44: 16–19 (1995).

Leibel, R. L., et al., "Changes in Energy Expenditure Resulting from Altered Body Weight," *New England Journal of Medicine,* 332(10):621–628 (1995).

Lithell, et al, "Insulin Sensitivity in Newly Detected Hypertensive Patients: Influence of Captopril and Other Antihypertensive Agents on Insulin Sensitivity and Related Biological Parameters," *J. Cardiovasc. Pharmacol.* 15 (Supp 5):S46–S52 (1990).

Malhotra et al. "Exendin–4, a new peptide from *Heloderma suspectum* venom, potentiates cholecystokinin–induced amylase release from rat pancreatic acini," *Regulatory Peptides,* 41:149–56 1992.

Montrose–Rafizadeh et al. "Structure–function Analysis of Exendin–4/GLP–1 Analogs," *Diabetes,* 45 (Suppl. 2):152A, 1996.

O'Halloran et al. "Glucagon–like peptide–1 (7,36)–$NH_2$: a physiological inhibitor of gastric acid secretion in man," *J. Endocrinol* 126(1):169–73 (1990).

Ørskov et al. "Biological Effects and Metabolic Rates of Glucagonlike Peptide–1 7–36 Amide and glucagonlike Peptide–1 7–37 in Healthy Subjects Are Indistinguishable," *Diabetes,* 42:658–61 (1993).

Pelleymounter, et al, "Effects of the obese Gene Product on Body Weight Regulation in ob/ob Mice," *Science,* 269:540–543 (1995).

Raufman et al. "Truncated Glucagon–like Peptide–1 Interacts with Exendin Receptors in Dispersed Acini from Guinea Pig Pancreas",*J. Biol. Chem.,* 267:21432–37 (1992).

Raufman et al. "Exendin–3, a Novel Peptide from *Heloderma horridum* Venom, Interacts with Vasoactive Intestinal Peptide Receptors and a Newly Described Receptor on dispersed Acini From Guinea Pig Pancreas," *J. Biol. Chem.,* 266:2897–902 (1991).

Schepp et al. "Exendin–4 and exendin–(9–39)$NH_2$: agonist and antagonist, respectively, at the rat parietal cell receptor for glucagon–like peptide–1–(7–36)$NH_2$," *Eur. J. Pharm.,* 269:183–91 (1994).

Schjoldager et al. "GLP–1 (Glucagon–like Peptide 1) and Truncated GLP–1, Fragments of Human Proglucagon, Inhibit Gastric Acid Secretion in Humans," *Dig Dis Sci* 34(5):703–8 (1989).

Singh et al. "Use of $^{125}$I–[$Y^{39}$]exendin–4 to characterize exendin receptors on dispersed pancreatic acini and gastric chief cells from guinea pig," *Regul. Pept.* 53:47–59 (1994).

Thorens, "Expression cloning of the pancreatic cell receptor for the gluco–incretin hormone glucagon–like peptide 1," *Proc. Natl. Acad. Sci. USA* 89:8641–45 (1992).

Thorens, et al. "Cloning and Functional Expression of the Human Islet GLP–1 Receptor." *Diabetes* 42(11):1678–82 1993.

Turton, et al, "A role for glucagon–like peptide–1 in the central regulation of feeding," *Nature* 379:69–72 1996.

Veale, P.R., et al, "The presence of islet amyloid polypeptide/calcitonin gen–related peptide/salmon calcitonin binding sites in the rat nucleus accumbens," *European Journal of Pharmacology* 262:133–141 1994.

Wang et al. "Glucagon–like Peptide–1 Is a Physiological Incretin in Rat," *J. Clin. Invest.,* 95:417–21 1995.

Watson, N., et al, "Effects of captopril on glucose tolerance in elderly patients with congestive cardiac failure," *Current Medical Research and Opinion,* 12(6):374–378 1991.

Wettergren et al. "Truncated GLP–1 (Proglucagon 78–107–Amide) Inhibits Gastric and Pancreatic Functions in Man," *Dig Dis Sci* 38(4):665–73 1993.

Willms, et al., "Gastric Emptying, Glucose Responses, and Insulin Secretion after a Liquid Test Mel: Effects of Exogenous Glucagon–Like Peptide–1 (GLP–1)–(7–36) Amide in Type 2 (Noninsulin–Dependent) Diabetic Patients," *J. Clin. Endocrinol. Metab.* 81(1):327–32 1996.

Young, et al, *Program and Abstracts, 10$^{th}$ International Congress of Endocrinology Jun. 12–15, 1996,* San Francisco, p. 419 (P2–58).

Lawler, R.L. et al., "Comparison of Effects of Amylin, Glucagon–like Peptide–1 (GLP–1) and Exendin–4 to Inhibit Pentagastrin–stimulated Gastric Acid Secretion in Rats," *Gastroenterology,* XP–002167251, 112(4 Supp):A194 (1997).

Navarro M et al., "Colocalization of Glucagon–like Peptide–1 (GLP–1) Receptors, Glucose Transporter GLUT–2, and Glucokinase mRNAs in Rat Hypothalamic Cells: Evidence for a Role of GLP–1 Receptor Agonists as an Inhibitory Signal for Food and Water Intake," *Journal of Neurochemistry,* 67:Abstract (1996).

Tang–Christensen, M. et al., "Central Administration of GLP–1–(7–36) Amide Inhibits Food and Water Intake in Rats," *American Physiological Society* 271 (4 pt 2): R848–R856 (1996).

\* cited by examiner

Xaa₁ Xaa₂ Xaa₃ Gly Thr Xaa₄ Xaa₅ Xaa₆ Xaa₇ Xaa₈ Ser Lys Gln Xaa₉ Glu Glu Glu Ala Val Arg Leu
Xaa₁₀ Xaa₁₁ Xaa₁₂ Xaa₁₃ Leu Lys Asn Gly Gly Xaa₁₄ Ser Ser Gly Ala Xaa₁₅ Xaa₁₆ Xaa₁₇ Xaa₁, Xaa₁₁-Z

| [SEQ. ID. NO.] | Xaa₁ | Xaa₂ | Xaa₃ | Xaa₄ | Xaa₅ | Xaa₄ | Xaa₇ | Xaa₈ | Xaa₉ | Xaa₁₀ | Xaa₁₁ | Xaa₁₂ | Xaa₁₃ | Xaa₁₄ | Xaa₁₅ | Xaa₁₆ | Xaa₁₇ | Xaa₁₈ | Z |
|---|---|---|---|---|---|---|---|---|---|---|---|---|---|---|---|---|---|---|---|
| 9 | His | Gly | Glu | Phe | Thr | Ser | Asp | Leu | Leu | Phe | Ile | Glu | Phe | Pro | Pro | Pro | Pro | Ser | NH₂ |
| 10 | His | Gly | Glu | Phe | Thr | Ser | Asp | Leu | Leu | Phe | Ile | Glu | Trp | Pro | Pro | Pro | Pro | Ser | NH₂ |
| 11 | His | Gly | Glu | Phe | Thr | Ser | Asp | Leu | Met | Phe | Ile | Glu | Phe | Pro | Pro | Pro | Pro | Ser | NH₂ |
| 12 | Tyr | Gly | Glu | Phe | Thr | Ser | Asp | Leu | Met | Phe | Ile | Glu | Trp | Pro | Pro | Pro | Pro | Tyr | NH₂ |
| 13 | His | Gly | Glu | Phe | Thr | Ser | Asp | Leu | Met | Phe | Ile | Glu | Trp | Pro | Pro | Pro | Pro | Ser | NH₂ |
| 14 | His | Gly | Asp | Phe | Thr | Ser | Asp | Leu | Met | Phe | Ile | Glu | Trp | Pro | Pro | Pro | Pro | Ser | NH₂ |
| 15 | His | Gly | Glu | naph | Thr | Ser | Asp | Leu | Met | Phe | Ile | Glu | Trp | Pro | Pro | Pro | Pro | Ser | NH₂ |
| 16 | His | Gly | Glu | Phe | Ser | Ser | Asp | Leu | Met | Phe | Ile | Glu | Trp | Pro | Pro | Pro | Pro | Ser | NH₂ |
| 17 | His | Gly | Glu | Phe | Ser | Thr | Asp | Leu | Met | Phe | Ile | Glu | Trp | Pro | Pro | Pro | Pro | Ser | NH₂ |
| 18 | His | Gly | Glu | Phe | Thr | Thr | Asp | Leu | Met | Phe | Ile | Glu | Trp | Pro | Pro | Pro | Pro | Ser | NH₂ |
| 19 | His | Gly | Glu | Phe | Thr | Ser | Glu | Leu | Met | Phe | Ile | Glu | Trp | Pro | Pro | Pro | Pro | Ser | NH₂ |
| 20 | His | Gly | Glu | Phe | Thr | Ser | Asp | pGly | Met | Phe | Ile | Glu | Trp | Pro | Pro | Pro | Pro | Ser | NH₂ |
| 21 | His | Gly | Glu | Phe | Thr | Ser | Asp | pGly | Leu | Phe | Ile | Glu | Phe | Pro | Pro | Pro | Pro | Ser | NH₂ |
| 22 | His | Gly | Glu | Phe | Thr | Ser | Asp. | Leu | pGly | Phe | Ile | Glu | Trp | Pro | Pro | Pro | Pro | Ser | NH₂ |

FIGURE 10A

| [SEQ. ID NO.] | Xaa1 | Xaa2 | Xaa3 | Xaa4 | Xaa5 | Xaa6 | Xaa7 | Xaa8 | Xaa9 | Xaa10 | Xaa11 | Xaa12 | Xaa13 | Xaa14 | Xaa15 | Xaa16 | Xaa17 | Xaa18 | Z |
|---|---|---|---|---|---|---|---|---|---|---|---|---|---|---|---|---|---|---|---|
| 23 | His | Gly | Glu | Phe | Thr | Ser | Asp | Leu | pGly | Phe | Ile | Glu | Phe | Pro | Pro | Pro | Pro | Ser | NH$_2$ |
| 24 | His | Gly | Glu | Phe | Thr | Ser | Asp | Leu | Met | naph | Ile | Glu | Trp | Pro | Pro | Pro | Pro | Ser | NH$_2$ |
| 25 | His | Gly | Glu | Phe | Thr | Ser | Asp | Leu | Met | Phe | Val | Glu | Trp | Pro | Pro | Pro | Pro | Ser | NH$_2$ |
| 26 | His | Gly | Glu | Phe | Thr | Ser | Asp | Leu | Leu | Phe | Val | Glu | Phe | Pro | Pro | Pro | Pro | Ser | NH$_2$ |
| 27 | His | Gly | Glu | Phe | Thr | Ser | Asp | Leu | Met | Phe | tBuG | Glu | Trp | Pro | Pro | Pro | Pro | Ser | NH$_2$ |
| 28 | His | Gly | Glu | Phe | Thr | Ser | Asp | Leu | Leu | Phe | tBuG | Asp | Phe | Pro | Pro | Pro | Pro | Ser | NH$_2$ |
| 29 | His | Gly | Glu | Phe | Thr | Ser | Asp | Leu | Met | Phe | Ile | Glu | Trp | Pro | Pro | Pro | Pro | Ser | NH$_2$ |
| 30 | His | Gly | Glu | Phe | Thr | Ser | Asp | Leu | Met | Phe | Ile | Glu | Phe | Pro | Pro | Pro | Pro | Ser | NH$_2$ |
| 31 | His | Gly | Glu | Phe | Thr | Ser | Asp | Leu | Met | Phe | Ile | Glu | Trp | tPro | tPro | tPro | tPro | Ser | NH$_2$ |
| 32 | His | Gly | Glu | Phe | Thr | Ser | Asp | Leu | Met | Phe | Ile | Glu | Trp | Pro | tPro | tPro | tPro | Ser | NH$_2$ |
| 33 | His | Gly | Glu | Phe | Thr | Ser | Asp | Leu | Met | Phe | Ile | Glu | Trp | hPro | hPro | hPro | hPro | Ser | NH$_2$ |
| 34 | His | Gly | Glu | Phe | Thr | Ser | Asp | Leu | Met | Phe | Ile | Glu | Trp | Pro | hPro | hPro | hPro | Ser | NH$_2$ |
| 35 | His | Gly | Glu | Phe | Thr | Ser | Asp | Leu | Leu | Phe | Ile | Glu | Phe | tPro | tPro | tPro | tPro | Ser | NH$_2$ |
| 36 | His | Gly | Glu | Phe | Thr | Ser | Asp | Leu | Leu | Phe | Ile | Glu | Phe | hPro | hPro | hPro | hPro | Ser | NH$_2$ |
| 37 | His | Gly | Glu | Phe | Thr | Ser | Asp | Leu | Met | Phe | Ile | Glu | Trp | MeAla | MeAla | MeAla | MeAla | Ser | NH$_2$ |
| 38 | His | Gly | Glu | Phe | Thr | Ser | Asp | Leu | Met | Phe | Ile | Glu | Trp | Pro | MeAla | MeAla | MeAla | Ser | NH$_2$ |
| 39 | His | Gly | Glu | Phe | Thr | Ser | Asp | Leu | Leu | Phe | Ile | Glu | Phe | MeAla | MeAla | MeAla | MeAla | Ser | NH$_2$ |

FIGURE 10.B

```
                          SEQUENCE LISTING

<160> NUMBER OF SEQ ID NOS: 188

<210> SEQ ID NO 1
<211> LENGTH: 39
<212> TYPE: PRT
<213> ORGANISM: Heloderma horridum
<220> FEATURE:
<221> NAME/KEY: AMIDATION
<222> LOCATION: (39)...(39)
<223> OTHER INFORMATION: amidated Ser (Serinamide)

<400> SEQUENCE: 1

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma suspectum
<220> FEATURE:
<221> NAME/KEY: AMIDATION
<222> LOCATION: (39)...(39)
<223> OTHER INFORMATION: amidated Ser (Serinamide)

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
```

```
<221> NAME/KEY: VARIANT
<222> LOCATION: (1)...(8)
<223> OTHER INFORMATION: Xaa in position 1 is His, Arg or Tyr; Xaa in
      position 2 is Ser, Gly, Ala or Thr; Xaa in position 3 is Asp or
      Glu; Xaa in position 6 is Phe, Tyr or naphthylalanine; Xaa in
      position 7 is Thr or Ser; Xaa in position 8 is Ser or Thr;
<220> FEATURE:
<221> NAME/KEY: VARIANT
<222> LOCATION: (9)...(22)
<223> OTHER INFORMATION: Xaa in position 9 is Asp or Glu; Xaa in
      position 10 is Leu, Ile, Val, pentylglycine or Met; Xaa in
      position 14 is Leu, Ile, pentylglycine, Val or Met; Xaa in
      position 22 is Phe, Tyr or naphthylalanine;
<220> FEATURE:
<221> NAME/KEY: VARIANT
<222> LOCATION: (23)...(25)
<223> OTHER INFORMATION: Xaa in position 23 is Ile, Val, Leu,
      pentylglycine, tert-butylglycine or Met; Xaa in position 24 is
      Glu or Asp; Xaa in position 25 is Trp, Phe, Tyr, or
      naphthylalanine;
<220> FEATURE:
<221> NAME/KEY: VARIANT
<222> LOCATION: (31)...(39)
<223> OTHER INFORMATION: Xaa in positions 31, 36, 37 and 38 are
      independently Pro, homoproline, 3-hydroxyproline,
      4-hydroxyproline, thioproline, N-alkylglycine,
      N-alkylpentylglycine or N-alkylalanine; Xaa in position 39 is
      Ser, Thr or Tyr;
<220> FEATURE:
<221> NAME/KEY: VARIANT
<222> LOCATION: (1)...(39)
<223> OTHER INFORMATION: with the proviso that the compound is not
      exendin-3 or exendin-4.
<220> FEATURE:
<221> NAME/KEY: AMIDATION
<222> LOCATION: (39)...(39)
<223> OTHER INFORMATION: The terminal amino acid may or may not be
      amidated.
<400> SEQUENCE: 3

Xaa Xaa Xaa Gly Thr Xaa Xaa Xaa Xaa Ser Lys Gln Xaa Glu Glu
 1               5                  10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
            35

<210> SEQ ID NO 4
<211> LENGTH: 38
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: VARIANT
<222> LOCATION: (1)...(7)
<223> OTHER INFORMATION: Xaa in position 1 is His, Arg or Tyr; Xaa in
      position 2 is Ser, Gly, Ala or Thr; Xaa in position 3 is Asp or
      Glu; Xaa in position 5 is Ala or Thr; Xaa in position 6 is Ala,
      Phe, Tyr or naphthylalanine; Xaa in position 7 is Thr or Ser;
<220> FEATURE:
<221> NAME/KEY: VARIANT
<222> LOCATION: (8)...(13)
<223> OTHER INFORMATION: Xaa in position 8 is Ala, Ser or Thr; Xaa in
      position 9 is Asp or Glu; Xaa in position 10 is Ala, Leu, Ile,
      Val, pentyl-glycine or Met; Xaa in position 11 is Ala or Ser; Xaa
      in position 12 is Ala or Lys; Xaa in position 13 is Ala or Gln;
<220> FEATURE:
<221> NAME/KEY: VARIANT
<222> LOCATION: (14)...(20)
<223> OTHER INFORMATION: Xaa in position 14 is Ala, Leu, Ile,
      pentylglycine, Val or Met; Xaa in position 15 is Ala or Glu; Xaa
      in position 16 is Ala or Glu; Xaa in position 17 is Ala or Glu;
      Xaa in position 19 is Ala or Val; Xaa in position 20 is Ala or
      Arg;
```

```
<220> FEATURE:
<221> NAME/KEY: VARIANT
<222> LOCATION: (21)...(24)
<223> OTHER INFORMATION: Xaa in position 21 is Ala or Leu; Xaa in
      position 22 is Ala, Phe, Tyr or naphthylalanine; Xaa in position
      23 is Ile, Val, Leu, pentylglycine, tert-butylglycine or Met; Xaa
      in position 24 is Ala, Glu or Asp;
<220> FEATURE:
<221> NAME/KEY: VARIANT
<222> LOCATION: (25)...(27)
<223> OTHER INFORMATION: Xaa in position 25 is Ala, Trp, Phe, Tyr or
      naphthylalanine; Xaa in position 26 is Ala or Leu; Xaa in
      position 27 is Ala or Lys;
<220> FEATURE:
<221> NAME/KEY: VARIANT
<222> LOCATION: (28)...(28)
<223> OTHER INFORMATION: Xaa in position 28 is Ala or Asn;
<220> FEATURE:
<221> NAME/KEY: VARIANT
<222> LOCATION: (29)...(30)
<223> OTHER INFORMATION: Xaa in position 29 is Gly or amino acid is
      missing; Xaa in position 30 is Gly or amino acid is missing;
<220> FEATURE:
<221> NAME/KEY: VARIANT
<222> LOCATION: (31)...(32)
<223> OTHER INFORMATION: Xaa in position 31 is Pro, homoproline, 3Hyp,
      4Hyp, thioproline, N-alkylglycine, N-alkylpentylglycine,
      N-alkylalanine, or amino acid is missing; Xaa in position 32 is
      Ser or amino acid is missing;
<220> FEATURE:
<221> NAME/KEY: VARIANT
<222> LOCATION: (33)...(35)
<223> OTHER INFORMATION: Xaa in position 33 is Ser or amino acid is
      missing; Xaa in position 34 is Gly or amino acid is missing;
      Xaa in position 35 is Ala or amino acid is missing;
<220> FEATURE:
<221> NAME/KEY: VARIANT
<222> LOCATION: (36)...(36)
<223> OTHER INFORMATION: Xaa in position 36 is Pro, homoproline, 3Hyp,
      4Hyp, thioproline, N-alkylglycine, N-alkylpentylglycine,
      N-alkylalanine, or amino acid is missing;
<220> FEATURE:
<221> NAME/KEY: VARIANT
<222> LOCATION: (37)...(37)
<223> OTHER INFORMATION: Xaa in position 37 is Pro, homoproline, 3Hyp,
      4Hyp, thioproline, N-alkylglycine, N-alkylpentylglycine,
      N-alkylalanine, or amino acid is missing;
<220> FEATURE:
<221> NAME/KEY: VARIANT
<222> LOCATION: (38)...(38)
<223> OTHER INFORMATION: Xaa in position 38 is Pro, homoproline, 3Hyp,
      4Hyp, thioproline, N-alkylglycine, N-alkylpentylglycine,
      N-alkylalanine, or amino acid is missing;
<220> FEATURE:
<221> NAME/KEY: AMIDATION
<222> LOCATION: (28)...(28)
<223> OTHER INFORMATION: When Xaa in position 28 is terminal amino acid
      in sequence, terminal amino acid may or may not be amidated;
<220> FEATURE:
<221> NAME/KEY: AMIDATION
<222> LOCATION: (29)...(29)
<223> OTHER INFORMATION: When Gly in position 29 is terminal amino acid
      in sequence, terminal amino acid may or may not be amidated;
<220> FEATURE:
<221> NAME/KEY: AMIDATION
<222> LOCATION: (30)...(30)
<223> OTHER INFORMATION: When Gly in position 30 is terminal amino acid
      in sequence, terminal amino acid may or may not be amidated;
<220> FEATURE:
<221> NAME/KEY: AMIDATION
<222> LOCATION: (31)...(31)
<223> OTHER INFORMATION: When Xaa in position 31 is terminal amino acid
      in sequence, terminal amino acid may or may not be amidated;
<220> FEATURE:
<221> NAME/KEY: AMIDATION
<222> LOCATION: (32)...(32)
<223> OTHER INFORMATION: When Ser in position 32 is terminal amino acid
      in sequence, terminal amino acid may or may not be amidated;
<220> FEATURE:
```

-continued

```
<221> NAME/KEY: AMIDATION
<222> LOCATION: (33)...(33)
<223> OTHER INFORMATION: When Ser in position 33 is terminal amino acid
      in sequence, terminal amino acid may or may not be amidated;
<220> FEATURE:
<221> NAME/KEY: AMIDATION
<222> LOCATION: (34)...(34)
<223> OTHER INFORMATION: When Gly in position 34 is terminal amino acid
      in sequence, terminal amino acid may or may not be amidated;
<220> FEATURE:
<221> NAME/KEY: AMIDATION
<222> LOCATION: (35)...(35)
<223> OTHER INFORMATION: When Ala in position 35 is terminal amino acid
      in sequence, terminal amino acid may or may not be amidated;
<220> FEATURE:
<221> NAME/KEY: AMIDATION
<222> LOCATION: (36)...(36)
<223> OTHER INFORMATION: When Xaa in position 36 is terminal amino acid
      in sequence, terminal amino acid may or may not be amidated;
<220> FEATURE:
<221> NAME/KEY: AMIDATION
<222> LOCATION: (37)...(37)
<223> OTHER INFORMATION: When Xaa in position 37 is terminal amino acid
      in sequence, terminal amino acid may or may not be amidated;
<220> FEATURE:
<221> NAME/KEY: AMIDATION
<222> LOCATION: (38)...(38)
<223> OTHER INFORMATION: When Xaa in position 38 is terminal amino acid
      in sequence, terminal amino acid may or may not be amidated;
<220> FEATURE:
<221> NAME/KEY: VARIANT
<222> LOCATION: (5)...(28)
<223> OTHER INFORMATION: provided that no more than three of Xaa in
      positions 5, 6, 8, 10, 11, 12, 13, 14, 15, 16, 17, 19, 20, 21,
      24, 25, 26, 27 and 28 are Ala.

<400> SEQUENCE: 4

Xaa Xaa Xaa Gly Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa Xaa Xaa
            20                  25                  30

Xaa Xaa Xaa Xaa Xaa Xaa
        35

<210> SEQ ID NO 5
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: VARIANT
<222> LOCATION: (1)...(5)
<223> OTHER INFORMATION: Xaa in position 1 is His, Arg, Tyr, Ala,
      Norval, Val or Norleu; Xaa in position 2 is Ser, Gly, Ala or Thr;
      Xaa in position 3 is Ala, Asp or Glu; Xaa in position 4 is Ala,
      Norval, Val, Norleu or Gly; Xaa in position 5 is Ala or Thr;
<220> FEATURE:
<221> NAME/KEY: VARIANT
<222> LOCATION: (6)...(10)
<223> OTHER INFORMATION: Xaa in position 6 is Phe, Tyr or naphthyl-
      alanine; Xaa in position 7 is Thr or Ser; Xaa in position 8 is
      Ala, Ser or Thr; Xaa in position 9 is Ala, Norval, Val, Norleu,
      Asp or Glu; Xaa in position 10 is Ala, Leu, Ile, Val, pentyl-
      glycine or Met;
<220> FEATURE:
<221> NAME/KEY: VARIANT
<222> LOCATION: (11)...(16)
<223> OTHER INFORMATION: Xaa in position 11 is Ala or Ser; Xaa in
      position 12 is Ala or Lys; Xaa in position 13 is Ala or Gln; Xaa
      in position 14 is Ala, Leu, Ile, pentylglycine, Val or Met; Xaa
      in position 15 is Ala or Glu; Xaa in position 16 is Ala or Glu;
<220> FEATURE:
<221> NAME/KEY: VARIANT
```

-continued

```
<222> LOCATION: (17)...(22)
<223> OTHER INFORMATION: Xaa in position 17 is Ala or Glu; Xaa in
      position 19 is Ala or Val; Xaa in position 20 is Ala or Arg; Xaa
      in position 21 is Ala or Leu; Xaa in position 22 is Phe, Tyr or
      naphthylalanine;
<220> FEATURE:
<221> NAME/KEY: VARIANT
<222> LOCATION: (23)...(26)
<223> OTHER INFORMATION: Xaa in position 23 is Ile, Val, Leu, pentyl-
      glycine, tert-butylglycine or Met; Xaa in position 24 is is Ala,
      Glu or Asp; Xaa in position 25 is Ala, Trp, Phe, Tyr or naphthyl-
      alanine; Xaa in position 26 is Ala or Leu;
<220> FEATURE:
<221> NAME/KEY: VARIANT
<222> LOCATION: (27)...(28)
<223> OTHER INFORMATION: Xaa in position 27 is Ala or Lys; Xaa in
      position 28 is Ala or Asn;
<220> FEATURE:
<221> NAME/KEY: VARIANT
<222> LOCATION: (29)...(30)
<223> OTHER INFORMATION: Xaa in position 29 is Gly or amino acid is
      missing; Xaa in position 30 is Gly or amino acid is missing;
<220> FEATURE:
<221> NAME/KEY: VARIANT
<222> LOCATION: (31)...(32)
<223> OTHER INFORMATION: Xaa in position 31 is Pro, homoproline, 3Hyp,
      4Hyp, thioproline, N-alkylglycine, N-alkylpentylglycine, N-alkyl-
      alanine, or amino acid is missing; Xaa in position 32 is Ser or
      amino acid is missing;
<220> FEATURE:
<221> NAME/KEY: VARIANT
<222> LOCATION: (33)...(35)
<223> OTHER INFORMATION: Xaa in position 33 is Ser or amino acid is
      missing; Xaa in position 34 is Gly or amino acid is missing;
      Xaa in position 35 is Ala or amino acid is missing;
<220> FEATURE:
<221> NAME/KEY: VARIANT
<222> LOCATION: (36)...(36)
<223> OTHER INFORMATION: Xaa in position 36 is Pro, homoproline, 3Hyp,
      4Hyp, thioproline, N-alkylglycine, N-alkylpentylglycine, N-alkyl-
      alanine, or amino acid is missing;
<220> FEATURE:
<221> NAME/KEY: VARIANT
<222> LOCATION: (37)...(37)
<223> OTHER INFORMATION: Xaa in position 37 is Pro, homoproline, 3Hyp,
      4Hyp, thioproline, N-alkylglycine, N-alkylpentylglycine, N-alkyl-
      alanine, or amino acid is missing;
<220> FEATURE:
<221> NAME/KEY: VARIANT
<222> LOCATION: (38)...(38)
<223> OTHER INFORMATION: Xaa in position 38 is Pro, homoproline, 3Hyp,
      4Hyp, thioproline, N-alkylglycine, N-alkylpentylglycine, N-alkyl-
      alanine, or amino acid is missing;
<220> FEATURE:
<221> NAME/KEY: VARIANT
<222> LOCATION: (39)...(39)
<223> OTHER INFORMATION: Xaa in position 39 is Pro, homoproline, 3Hyp,
      4Hyp, thioproline, N-alkylglycine, N-alkylpentylglycine, N-alkyl-
      alanine, or amino acid is missing;
<220> FEATURE:
<221> NAME/KEY: AMIDATION
<222> LOCATION: (28)...(28)
<223> OTHER INFORMATION: When Xaa in position 28 is terminal amino acid
      in sequence, terminal amino acid may or may not be amidated;
<220> FEATURE:
<221> NAME/KEY: AMIDATION
<222> LOCATION: (29)...(29)
<223> OTHER INFORMATION: When Gly in position 29 is terminal amino acid
      in sequence, terminal amino acid may or may not be amidated;
<220> FEATURE:
<221> NAME/KEY: AMIDATION
<222> LOCATION: (30)...(30)
<223> OTHER INFORMATION: When Gly in position 30 is terminal amino acid
      in sequence, terminal amino acid may or may not be amidated;
<220> FEATURE:
<221> NAME/KEY: AMIDATION
<222> LOCATION: (31)...(31)
<223> OTHER INFORMATION: When Xaa in position 31 is terminal amino acid
      in sequence, terminal amino acid may or may not be amidated;
```

```
<220> FEATURE:
<221> NAME/KEY: AMIDATION
<222> LOCATION: (32)...(32)
<223> OTHER INFORMATION: When Ser in position 32 is terminal amino acid
      in sequence, terminal amino acid may or may not be amidated;
<220> FEATURE:
<221> NAME/KEY: AMIDATION
<222> LOCATION: (33)...(33)
<223> OTHER INFORMATION: When Ser in position 33 is terminal amino acid
      in sequence, terminal amino acid may or may not be amidated;
<220> FEATURE:
<221> NAME/KEY: AMIDATION
<222> LOCATION: (34)...(34)
<223> OTHER INFORMATION: When Gly in position 34 is terminal amino acid
      in sequence, terminal amino acid may or may not be amidated;
<220> FEATURE:
<221> NAME/KEY: AMIDATION
<222> LOCATION: (35)...(35)
<223> OTHER INFORMATION: When Ala in position 35 is terminal amino acid
      in sequence, terminal amino acid may or may not be amidated;
<220> FEATURE:
<221> NAME/KEY: AMIDATION
<222> LOCATION: (36)...(36)
<223> OTHER INFORMATION: When Xaa in position 36 is terminal amino acid
      in sequence, terminal amino acid may or may not be amidated;
<220> FEATURE:
<221> NAME/KEY: AMIDATION
<222> LOCATION: (37)...(37)
<223> OTHER INFORMATION: When Xaa in position 37 is terminal amino acid
      in sequence, terminal amino acid may or may not be amidated;
<220> FEATURE:
<221> NAME/KEY: AMIDATION
<222> LOCATION: (38)...(38)
<223> OTHER INFORMATION: When Xaa in position 38 is terminal amino acid
      in sequence, terminal amino acid may or may not be amidated;
<220> FEATURE:
<221> NAME/KEY: AMIDATION
<222> LOCATION: (39)...(39)
<223> OTHER INFORMATION: When Xaa in position 39 is terminal amino acid
      in sequence, terminal amino acid may or may not be amidated;
<220> FEATURE:
<221> NAME/KEY: VARIANT
<222> LOCATION: (3)...(28)
<223> OTHER INFORMATION: provided that no more than three of Xaa in
      positions 3, 4, 5, 8, 9, 10, 11, 12, 13, 14, 15, 16, 17, 19, 20,
      21, 24, 25, 26 27 and 28 are Ala;
<220> FEATURE:
<221> NAME/KEY: VARIANT
<222> LOCATION: (1)...(9)
<223> OTHER INFORMATION: and provided also that, if Xaa in position 1
      is His, Arg or Tyr, then at least one of Xaa in positions 3, 4
      and 9 is Ala.

<400> SEQUENCE: 5

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa
         35

<210> SEQ ID NO 6
<211> LENGTH: 30
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (30)...(30)
<223> OTHER INFORMATION: amidated Gly (Glycinamide)

<400> SEQUENCE: 6
```

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30
```

<210> SEQ ID NO 7
<211> LENGTH: 30
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (30)...(30)
<223> OTHER INFORMATION: amidated Gly (Glycinamide)

<400> SEQUENCE: 7

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30
```

<210> SEQ ID NO 8
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 8

```
His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25
```

<210> SEQ ID NO 9
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 9

```
His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35
```

<210> SEQ ID NO 10
<211> LENGTH: 39
<212> TYPE: PRT
<213> ORGANISM: Artificial Sequence
<220> FEATURE:

```
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 10

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 11

His Gly Glu Gly Thr Phe Thr Ser Asp Leu Ser Lys Gln Met Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 12

Tyr Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Tyr (Tyrosinamide)
```

-continued

```
<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Tyr
        35

<210> SEQ ID NO 14
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 14

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 6 stands for naphthylalanine.
<220> FEATURE:
<221> NAME/KEY: AMIDATION
<222> LOCATION: (39)...(39)
<223> OTHER INFORMATION: amidated Ser (Serinamide)

<400> SEQUENCE: 15

His Gly Glu Gly Thr Xaa Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 16

His Gly Glu Gly Thr Phe Ser Ser Asp Leu Ser Lys Gln Met Glu Glu
1               5                   10                  15
```

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 17
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 17

His Gly Glu Gly Thr Phe Ser Thr Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 18
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 18

His Gly Glu Gly Thr Phe Thr Thr Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 19
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 19

His Gly Glu Gly Thr Phe Thr Ser Glu Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser
            35

```
<210> SEQ ID NO 20
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 10 stands for pentylglycine.
<220> FEATURE:
<221> NAME/KEY: AMIDATION
<222> LOCATION: (39)...(39)
<223> OTHER INFORMATION: amidated Ser (Serinamide)

<400> SEQUENCE: 20

His Gly Glu Gly Thr Phe Thr Ser Asp Xaa Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 21
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 10 stands for pentylglycine.
<220> FEATURE:
<221> NAME/KEY: AMIDATION
<222> LOCATION: (39)...(39)
<223> OTHER INFORMATION: amidated Ser (Serinamide)

<400> SEQUENCE: 21

His Gly Glu Gly Thr Phe Thr Ser Asp Xaa Ser Lys Gln Leu Glu Glu
  1               5                  10                  15

Glu Ala Val Arg Leu Phe Ile Glu Phe Leu Lys Asn Gly Gly Pro Ser
             20                  25                  30

Ser Gly Ala Pro Pro Pro Ser
         35

<210> SEQ ID NO 22
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 14 stands for pentylglycine.
<220> FEATURE:
<221> NAME/KEY: AMIDATION
<222> LOCATION: (39)...(39)
<223> OTHER INFORMATION: amidated Ser (Serinamide)

<400> SEQUENCE: 22

His Gly Glu Gly Thr Phe Thr Ser Asp Leu Ser Lys Gln Xaa Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 23
```

```
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 14 stands for pentylglycine.
<220> FEATURE:
<221> NAME/KEY: AMIDATION
<222> LOCATION: (39)...(39)
<223> OTHER INFORMATION: amidated Ser (Serinamide)

<400> SEQUENCE: 23
```

His Gly Glu Gly Thr Phe Thr Ser Asp Leu Ser Lys Gln Xaa Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

```
<210> SEQ ID NO 24
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 22 stands for naphthylalanine.
<220> FEATURE:
<221> NAME/KEY: AMIDATION
<222> LOCATION: (39)...(39)
<223> OTHER INFORMATION: amidated Ser (Serinamide)

<400> SEQUENCE: 24
```

His Gly Glu Gly Thr Phe Thr Ser Asp Leu Ser Lys Gln Met Glu Glu
1               5                   10                  15

Glu Ala Val Arg Leu Xaa Ile Glu Trp Leu Lys Asn Gly Gly Pro Ser
            20                  25                  30

Ser Gly Ala Pro Pro Pro Ser
        35

```
<210> SEQ ID NO 25
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 25
```

His Gly Glu Gly Thr Phe Thr Ser Asp Leu Ser Lys Gln Met Glu Glu
1               5                   10                  15

Glu Ala Val Arg Leu Phe Val Glu Trp Leu Lys Asn Gly Gly Pro Ser
            20                  25                  30

Ser Gly Ala Pro Pro Pro Ser
        35

```
<210> SEQ ID NO 26
<211> LENGTH: 39
<212> TYPE: PRT
<213> ORGANISM: Artificial Sequence
```

```
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 26

His Gly Glu Gly Thr Phe Thr Ser Asp Leu Ser Lys Gln Leu Glu Glu
 1               5                  10                  15

Glu Ala Val Arg Leu Phe Val Glu Phe Leu Lys Asn Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 23 stands for tertiary-
      butylglycine.
<220> FEATURE:
<221> NAME/KEY: AMIDATION
<222> LOCATION: (39)...(39)
<223> OTHER INFORMATION: amidated Ser (Serinamide)

<400> SEQUENCE: 27

His Gly Glu Gly Thr Phe Thr Ser Asp Leu Ser Lys Gln Met Glu Glu
 1               5                  10                  15

Glu Ala Val Arg Leu Phe Xaa Glu Trp Leu Lys Asn Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 23 stands for tertiary-
      butylglycine.
<220> FEATURE:
<221> NAME/KEY: AMIDATION
<222> LOCATION: (39)...(39)
<223> OTHER INFORMATION: amidated Ser (Serinamide)

<400> SEQUENCE: 28

His Gly Glu Gly Thr Phe Thr Ser Asp Leu Ser Lys Gln Leu Glu Glu
 1               5                  10                  15

Glu Ala Val Arg Leu Phe Xaa Glu Phe Leu Lys Asn Gly Gly Pro Ser
            20                  25                  30

Ser Gly Ala Pro Pro Pro Ser
        35

<210> SEQ ID NO 29
<211> LENGTH: 39
<212> TYPE: PRT
<213> ORGANISM: Artificial Sequence
<220> FEATURE:
```

```
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 29
```

His Gly Glu Gly Thr Phe Thr Ser Asp Leu Ser Lys Gln Met Glu Glu
 1               5                  10                  15

Glu Ala Val Arg Leu Phe Ile Asp Trp Leu Lys Asn Gly Gly Pro Ser
            20                  25                  30

Ser Gly Ala Pro Pro Pro Ser
        35

```
<210> SEQ ID NO 30
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 30
```

His Gly Glu Gly Thr Phe Thr Ser Asp Leu Ser Lys Gln Met Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

```
<210> SEQ ID NO 31
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 31, 36, 37 and 38 stands for
      thioproline.
<220> FEATURE:
<221> NAME/KEY: AMIDATION
<222> LOCATION: (39)...(39)
<223> OTHER INFORMATION: amidated Ser (Serinamide)

<400> SEQUENCE: 31
```

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35

```
<210> SEQ ID NO 32
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 36, 37 and 38 stands for
``` thioproline.
<220> FEATURE:
<221> NAME/KEY: AMIDATION
<222> LOCATION: (39)...(39)
<223> OTHER INFORMATION: amidated Ser (Serinamide)

<400> SEQUENCE: 32

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa Ser
        35

<210> SEQ ID NO 33
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 31, 36, 37 and 38 stands for
      homoproline.
<220> FEATURE:
<221> NAME/KEY: AMIDATION
<222> LOCATION: (39)...(39)
<223> OTHER INFORMATION: amidated Ser (Serinamide)

<400> SEQUENCE: 33

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35

<210> SEQ ID NO 34
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 36, 37 and 38 stands for
      homoproline.
<220> FEATURE:
<221> NAME/KEY: AMIDATION
<222> LOCATION: (39)...(39)
<223> OTHER INFORMATION: amidated Ser (Serinamide)

<400> SEQUENCE: 34

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa Ser
        35

<210> SEQ ID NO 35
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound

```
<220> FEATURE:
<223> OTHER INFORMATION: Xaa in positions 31, 36, 37 and 38 stands for
      thioproline.
<220> FEATURE:
<221> NAME/KEY: AMIDATION
<222> LOCATION: (39)...(39)
<223> OTHER INFORMATION: amidated Ser (Serinamide)

<400> SEQUENCE: 35

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Xaa Ser
             20                  25                  30

Ser Gly Ala Xaa Xaa Xaa Ser
         35

<210> SEQ ID NO 36
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 31, 36, 37 and 38 stands for
      homoproline.
<220> FEATURE:
<221> NAME/KEY: AMIDATION
<222> LOCATION: (39)...(39)
<223> OTHER INFORMATION: amidated Ser (Serinamide)

<400> SEQUENCE: 36

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Xaa Ser
             20                  25                  30

Ser Gly Ala Xaa Xaa Xaa Ser
         35

<210> SEQ ID NO 37
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 31, 36, 37 and 38 stands for
      n-methylalanine.
<220> FEATURE:
<221> NAME/KEY: AMIDATION
<222> LOCATION: (39)...(39)
<223> OTHER INFORMATION: amidated Ser (Serinamide)

<400> SEQUENCE: 37

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Xaa Ser
             20                  25                  30

Ser Gly Ala Xaa Xaa Xaa Ser
         35

<210> SEQ ID NO 38
<211> LENGTH: 39
<212> TYPE: PRT
<213> ORGANISM: Artificial Sequence
<220> FEATURE:
```

```
<223> OTHER INFORMATION: artificially synthesized sequence of novel
      exendin agonist compound
<220> FEATURE:
<223> OTHER INFORMATION: Xaa in positions 36, 37 and 38 stands for
      n-methylalanine.
<220> FEATURE:
<221> NAME/KEY: AMIDATION
<222> LOCATION: (39)...(39)
<223> OTHER INFORMATION: amidated Ser (Serinamide)

<400> SEQUENCE: 38

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Xaa Xaa Xaa Ser
         35

<210> SEQ ID NO 39
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 31, 36, 37 and 38 stands for
      n-methylalanine.
<220> FEATURE:
<221> NAME/KEY: AMIDATION
<222> LOCATION: (39)...(39)
<223> OTHER INFORMATION: amidated Ser (Serinamide)

<400> SEQUENCE: 39

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Xaa Ser
             20                  25                  30

Ser Gly Ala Xaa Xaa Xaa Ser
         35

<210> SEQ ID NO 40
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 40

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
             20                  25

<210> SEQ ID NO 41
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
```

```
<222> LOCATION: (28)...(28)
<223> OTHER INFORMATION: amidated Asn (Asparaginamide)

<400> SEQUENCE: 41

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 42
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 42

His Ala Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 43
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 43

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 44
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 44

His Gly Glu Gly Thr Ala Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 45
<211> LENGTH: 28
<212> TYPE: PRT
<213> ORGANISM: Artificial Sequence
```

```
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 45

His Gly Glu Gly Thr Phe Thr Ala Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 46
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 46

His Gly Glu Gly Thr Phe Thr Ser Asp Ala Ser Lys Gln Leu Glu Glu
 1               5                  10                  15

Glu Ala Val Arg Leu Phe Ile Glu Phe Leu Lys Asn
            20                  25

<210> SEQ ID NO 47
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 47

His Gly Glu Gly Thr Phe Thr Ser Asp Leu Ala Lys Gln Leu Glu Glu
 1               5                  10                  15

Glu Ala Val Arg Leu Phe Ile Glu Phe Leu Lys Asn
            20                  25

<210> SEQ ID NO 48
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 48

His Gly Glu Gly Thr Phe Thr Ser Asp Leu Ser Ala Gln Leu Glu Glu
 1               5                  10                  15

Glu Ala Val Arg Leu Phe Ile Glu Phe Leu Lys Asn
            20                  25
```

```
<210> SEQ ID NO 49
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 49

His Gly Glu Gly Thr Phe Thr Ser Asp Leu Ser Lys Ala Leu Glu Glu
  1               5                  10                  15

Glu Ala Val Arg Leu Phe Ile Glu Phe Leu Lys Asn
             20                  25

<210> SEQ ID NO 50
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 50

His Gly Glu Gly Thr Phe Thr Ser Asp Leu Ser Lys Gln Ala Glu Glu
  1               5                  10                  15

Glu Ala Val Arg Leu Phe Ile Glu Phe Leu Lys Asn
             20                  25

<210> SEQ ID NO 51
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 51

His Gly Glu Gly Thr Phe Thr Ser Asp Leu Ser Lys Gln Leu Ala Glu
  1               5                  10                  15

Glu Ala Val Arg Leu Phe Ile Glu Phe Leu Lys Asn
             20                  25

<210> SEQ ID NO 52
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 52

His Gly Glu Gly Thr Phe Thr Ser Asp Leu Ser Lys Gln Leu Glu Ala
```

```
                 1               5                  10                 15
Glu Ala Val Arg Leu Phe Ile Glu Phe Leu Lys Asn
                20                 25

<210> SEQ ID NO 53
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 53

His Gly Glu Gly Thr Phe Thr Ser Asp Leu Ser Lys Gln Leu Glu Glu
 1               5                  10                 15

Ala Ala Val Arg Leu Phe Ile Glu Phe Leu Lys Asn
                20                 25

<210> SEQ ID NO 54
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 54

His Gly Glu Gly Thr Phe Thr Ser Asp Leu Ser Lys Gln Leu Glu Glu
 1               5                  10                 15

Glu Ala Ala Arg Leu Phe Ile Glu Phe Leu Lys Asn
                20                 25

<210> SEQ ID NO 55
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 55

His Gly Glu Gly Thr Phe Thr Ser Asp Leu Ser Lys Gln Leu Glu Glu
 1               5                  10                 15

Glu Ala Val Ala Leu Phe Ile Glu Phe Leu Lys Asn
                20                 25

<210> SEQ ID NO 56
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
```

<223> OTHER INFORMATION: amidated Asn (Asparaginamide)

<400> SEQUENCE: 56

His Gly Glu Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 57
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 57

His Gly Glu Gly Thr Phe Thr Ser Asp Leu Ser Lys Gln Leu Glu Glu
1               5                   10                  15

Glu Ala Val Arg Leu Phe Ile Ala Phe Leu Lys Asn
            20                  25

<210> SEQ ID NO 58
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 58

His Gly Glu Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 59
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 59

His Gly Glu Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 60
<211> LENGTH: 28
<212> TYPE: PRT
<213> ORGANISM: Artificial Sequence
<220> FEATURE:

```
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 60

His Gly Glu Gly Thr Phe Thr Ser Asp Leu Ser Lys Gln Leu Glu Glu
 1               5                  10                  15

Glu Ala Val Arg Leu Phe Ile Glu Phe Leu Ala Asn
             20                  25

<210> SEQ ID NO 61
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Ala (Alaninamide)

<400> SEQUENCE: 61

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Ala
             20                  25

<210> SEQ ID NO 62
<211> LENGTH: 38
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (38)...(38)
<223> OTHER INFORMATION: amidated Pro (Prolinamide)

<400> SEQUENCE: 62

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Pro
                 35

<210> SEQ ID NO 63
<211> LENGTH: 38
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (38)...(38)
<223> OTHER INFORMATION: amidated Pro (Prolinamide)

<400> SEQUENCE: 63

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
```

```
                    20                  25                  30

Ser Gly Ala Pro Pro Pro
        35

<210> SEQ ID NO 64
<211> LENGTH: 37
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (37)...(37)
<223> OTHER INFORMATION: amidated Pro (Prolinamide)

<400> SEQUENCE: 64

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro
        35

<210> SEQ ID NO 65
<211> LENGTH: 37
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (37)...(37)
<223> OTHER INFORMATION: amidated Pro (Prolinamide)

<400> SEQUENCE: 65

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
                20                  25                  30

Ser Gly Ala Pro Pro
        35

<210> SEQ ID NO 66
<211> LENGTH: 36
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (36)...(36)
<223> OTHER INFORMATION: amidated Pro (Prolinamide)

<400> SEQUENCE: 66

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro
        35

<210> SEQ ID NO 67
```

```
<211> LENGTH: 36
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (36)...(36)
<223> OTHER INFORMATION: amidated Pro (Prolinamide)

<400> SEQUENCE: 67

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
             20                  25                  30

Ser Gly Ala Pro
        35

<210> SEQ ID NO 68
<211> LENGTH: 35
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (35)...(35)
<223> OTHER INFORMATION: amidated Ala (Alaninamide)

<400> SEQUENCE: 68

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala
        35

<210> SEQ ID NO 69
<211> LENGTH: 35
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (35)...(35)
<223> OTHER INFORMATION: amidated Ala (Alaninamide)

<400> SEQUENCE: 69

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
             20                  25                  30

Ser Gly Ala
        35

<210> SEQ ID NO 70
<211> LENGTH: 34
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
```

```
<221> NAME/KEY: AMIDATION
<222> LOCATION: (34)...(34)
<223> OTHER INFORMATION: amidated Gly (Glycinamide)

<400> SEQUENCE: 70

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly

<210> SEQ ID NO 71
<211> LENGTH: 34
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (34)...(34)
<223> OTHER INFORMATION: amidated Gly (Glycinamide)

<400> SEQUENCE: 71

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly

<210> SEQ ID NO 72
<211> LENGTH: 33
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (33)...(33)
<223> OTHER INFORMATION: amidated Ser (Serinamide)

<400> SEQUENCE: 72

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser

<210> SEQ ID NO 73
<211> LENGTH: 33
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (33)...(33)
<223> OTHER INFORMATION: amidated Ser (Serinamide)

<400> SEQUENCE: 73

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
```

Ser

```
<210> SEQ ID NO 74
<211> LENGTH: 32
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (32)...(32)
<223> OTHER INFORMATION: amidated Ser (Serinamide)

<400> SEQUENCE: 74
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

```
<210> SEQ ID NO 75
<211> LENGTH: 32
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (32)...(32)
<223> OTHER INFORMATION: amidated Ser (Serinamide)

<400> SEQUENCE: 75
```

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

```
<210> SEQ ID NO 76
<211> LENGTH: 31
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (31)...(31)
<223> OTHER INFORMATION: amidated Pro (Prolinamide)

<400> SEQUENCE: 76
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

```
<210> SEQ ID NO 77
<211> LENGTH: 31
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (31)...(31)
<223> OTHER INFORMATION: amidated Pro (Prolinamide)
```

<400> SEQUENCE: 77

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (30)...(30)
<223> OTHER INFORMATION: amidated Gly (Glycinamide)

<400> SEQUENCE: 78

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 79
<211> LENGTH: 29
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (29)...(29)
<223> OTHER INFORMATION: amidated Gly (Glycinamide)

<400> SEQUENCE: 79

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly
            20                  25

<210> SEQ ID NO 80
<211> LENGTH: 29
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (29)...(29)
<223> OTHER INFORMATION: amidated Gly (Glycinamide)

<400> SEQUENCE: 80

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly
            20                  25

<210> SEQ ID NO 81
<211> LENGTH: 38
<212> TYPE: PRT
<213> ORGANISM: Artificial Sequence
<220> FEATURE:
<223> OTHER INFORMATION: artificially synthesized sequence of novel

```
      exendin agonist compound
<220> FEATURE:
<223> OTHER INFORMATION: Xaa in positions 31, 36, 37 and 38 stand for
      thioproline.
<220> FEATURE:
<221> NAME/KEY: AMIDATION
<222> LOCATION: (38)...(38)
<223> OTHER INFORMATION: amidated tPro (thioprolinamide)

<400> SEQUENCE: 81

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa
            35

<210> SEQ ID NO 82
<211> LENGTH: 38
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 36, 37 and 38 stand for
      thioproline.
<220> FEATURE:
<221> NAME/KEY: AMIDATION
<222> LOCATION: (38)...(38)
<223> OTHER INFORMATION: amidated tPro (thioprolinamide)

<400> SEQUENCE: 82

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa
            35

<210> SEQ ID NO 83
<211> LENGTH: 37
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 31 stands for n-methylalanine.
<220> FEATURE:
<221> NAME/KEY: AMIDATION
<222> LOCATION: (37)...(37)
<223> OTHER INFORMATION: amidated Pro (Prolinamide)

<400> SEQUENCE: 83

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Pro Pro
            35

<210> SEQ ID NO 84
<211> LENGTH: 37
<212> TYPE: PRT
<213> ORGANISM: Artificial Sequence
<220> FEATURE:
```

```
<223> OTHER INFORMATION: artificially synthesized sequence of novel
      exendin agonist compound
<220> FEATURE:
<223> OTHER INFORMATION: X

```
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (35)...(35)
<223> OTHER INFORMATION: amidated Ala (Alaninamide)

<400> SEQUENCE: 87

Arg Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
        35

<210> SEQ ID NO 88
<211> LENGTH: 30
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (30)...(30)
<223> OTHER INFORMATION: amidated Gly (Glycinamide)

<400> SEQUENCE: 88

His Gly Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 89
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 6 stands for naphthylalanine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 89

His Gly Glu Gly Thr Xaa Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 90
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 90
```

```
His Gly Glu Gly Thr Phe Ser Ser Asp Leu Ser Lys Gln Met Glu Glu
1               5                   10                  15

Glu Ala Val Arg Leu Phe Ile Glu Trp Leu Lys Asn
                20                  25

<210> SEQ ID NO 91
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 91

His Gly Glu Gly Thr Phe Ser Thr Asp Leu Ser Lys Gln Met Glu Glu
1               5                   10                  15

Glu Ala Val Arg Leu Phe Ile Glu Trp Leu Lys Asn
                20                  25

<210> SEQ ID NO 92
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 92

His Gly Glu Gly Thr Phe Thr Ser Glu Leu Ser Lys Gln Met Ala Glu
1               5                   10                  15

Glu Ala Val Arg Leu Phe Ile Glu Trp Leu Lys Asn
                20                  25

<210> SEQ ID NO 93
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 10 stands for pentylglycine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 93

His Gly Glu Gly Thr Phe Thr Ser Asp Xaa Ser Lys Gln Leu Glu Glu
1               5                   10                  15

Glu Ala Val Arg Leu Phe Ile Glu Phe Leu Lys Asn
                20                  25

<210> SEQ ID NO 94
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
```

```
<220> FEATURE:
<223> OTHER INFORMATION: Xaa in position 22 stands for naphthylalanine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 94

His Gly Glu Gly Thr Phe Thr Ser Asp Leu Ser Lys Gln Leu Glu Glu
 1               5                  10                  15

Glu Ala Val Arg Leu Xaa Ile Glu Phe Leu Lys Asn
            20                  25

<210> SEQ ID NO 95
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 23 stands for tertiary-
      butylglycine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 95

His Gly Glu Gly Thr Phe Thr Ser Asp Leu Ser Lys Gln Met Glu Glu
 1               5                  10                  15

Glu Ala Val Arg Leu Phe Xaa Glu Trp Leu Lys Asn
            20                  25

<210> SEQ ID NO 96
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 96

His Gly Glu Gly Thr Phe Thr Ser Asp Leu Ser Lys Gln Leu Glu Glu
 1               5                  10                  15

Glu Ala Val Arg Leu Phe Ile Asp Phe Leu Lys Asn
            20                  25

<210> SEQ ID NO 97
<211> LENGTH: 33
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (33)...(33)
<223> OTHER INFORMATION: amidated Ser (Serinamide)

<400> SEQUENCE: 97

His Gly Glu Gly Thr Phe Thr Ser Asp Ala Ser Lys Gln Leu Glu Glu
 1               5                  10                  15

Glu Ala Val Arg Leu Phe Ile Glu Phe Leu Lys Asn Gly Gly Pro Ser
```

```
                20                  25                  30
Ser

<210> SEQ ID NO 98
<211> LENGTH: 29
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (29)...(29)
<223> OTHER INFORMATION: amidated Gly (Glycinamide)

<400> SEQUENCE: 98

His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn Gly
            20                  25

<210> SEQ ID NO 99
<211> LENGTH: 37
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 31, 36 and 37 stands for
      homoproline.
<220> FEATURE:
<221> NAME/KEY: AMIDATION
<222> LOCATION: (37)...(37)
<223> OTHER INFORMATION: amidated hPro (homoprolinamide)

<400> SEQUENCE: 99

His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 100
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 100

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 101
<211> LENGTH: 28
<212> TYPE: PRT
<213> ORGANISM: Artificial Sequence
<220> FEATURE:
```

```
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 101

His Gly Ala Gly Thr Phe Thr Ser Asp Leu Ser Lys Gln Leu Glu Glu
  1               5                  10                  15

Glu Ala Val Arg Leu Phe Ile Glu Phe Leu Lys Asn
             20                  25

<210> SEQ ID NO 102
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 102

His Gly Glu Ala Thr Phe Thr Ser Asp Leu Ser Lys Gln Leu Glu Glu
  1               5                  10                  15

Glu Ala Val Arg Leu Phe Ile Glu Phe Leu Lys Asn
             20                  25

<210> SEQ ID NO 103
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 103

His Gly Glu Gly Thr Phe Thr Ser Ala Leu Ser Lys Gln Leu Glu Glu
  1               5                  10                  15

Glu Ala Val Arg Leu Phe Ile Glu Phe Leu Lys Asn
             20                  25

<210> SEQ ID NO 104
<211> LENGTH: 28
<212> TYPE: PRT
<213> ORGANISM: Artificial Sequence
<220> FEATURE:
<221> NAME/KEY: AMIDATION
<222> LOCATION: (28)...(28)
<223> OTHER INFORMATION: amidated Asn (Asparaginamide)

<400> SEQUENCE: 104

Ala Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn
             20                  25

<210> SEQ ID NO 105
<211> LENGTH: 28
<212> TYPE: PRT
```

```
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 105

His Gly Ala Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 106
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 106

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 107
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 107

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn
            20                  25

<210> SEQ ID NO 108
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 108

His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn
            20                  25
```

```
<210> SEQ ID NO 109
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 109

Ala Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 110
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 110

Ala Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 111
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 111

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 112
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 112
```

```
Ala Gly Asp Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25
```

<210> SEQ ID NO 113
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 113

```
Ala Gly Asp Gly Ala Phe Thr Ser Asp Leu Ser Lys Gln Met Glu Glu
 1               5                  10                  15

Glu Ala Val Arg Leu Phe Ile Glu Trp Leu Lys Asn
            20                  25
```

<210> SEQ ID NO 114
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 114

```
Ala Gly Asp Gly Ala Phe Thr Ser Asp Leu Ser Lys Gln Leu Glu Glu
 1               5                  10                  15

Glu Ala Val Arg Leu Phe Ile Glu Phe Leu Lys Asn
            20                  25
```

<210> SEQ ID NO 115
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 6 stands for naphthylalanine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 115

```
Ala Gly Asp Gly Thr Xaa Thr Ser Asp Leu Ser Lys Gln Met Glu Glu
 1               5                  10                  15

Glu Ala Val Arg Leu Phe Ile Glu Trp Leu Lys Asn
            20                  25
```

<210> SEQ ID NO 116
<211> LENGTH: 28
<212> TYPE: PRT
<213> ORGANISM: Artificial Sequence
<220> FEATURE:
<223> OTHER INFORMATION: Xaa in position 6 stands for naphthylalanine.
<220> FEATURE:

```
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 116

Ala Gly Asp Gly Thr Xaa Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 117
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 117

Ala Gly Asp Gly Thr Phe Ser Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 118
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 118

Ala Gly Asp Gly Thr Phe Ser Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 119
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 119

Ala Gly Asp Gly Thr Phe Thr Ala Asp Leu Ser Lys Gln Met Glu Glu
1               5                   10                  15

Glu Ala Val Arg Leu Phe Ile Glu Trp Leu Lys Asn
            20                  25
```

```
<210> SEQ ID NO 120
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 120

Ala Gly Asp Gly Thr Phe Thr Ala Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 121
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 121

Ala Gly Asp Gly Thr Phe Thr Ser Ala Leu Ser Lys Gln Met Glu Glu
 1               5                  10                  15

Glu Ala Val Arg Leu Phe Ile Glu Trp Leu Lys Asn
            20                  25

<210> SEQ ID NO 122
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 122

Ala Gly Asp Gly Thr Phe Thr Ser Ala Leu Ser Lys Gln Leu Glu Glu
 1               5                  10                  15

Glu Ala Val Arg Leu Phe Ile Glu Phe Leu Lys Asn
            20                  25

<210> SEQ ID NO 123
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 123

Ala Gly Asp Gly Thr Phe Thr Ser Glu Leu Ser Lys Gln Met Glu Glu
 1               5                  10                  15
```

Glu Ala Val Arg Leu Phe Ile Glu Trp Leu Lys Asn
            20                  25

<210> SEQ ID NO 124
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 124

Ala Gly Asp Gly Thr Phe Thr Ser Glu Leu Ser Lys Gln Leu Glu Glu
1               5                   10                  15

Glu Ala Val Arg Leu Phe Ile Glu Phe Leu Lys Asn
            20                  25

<210> SEQ ID NO 125
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 125

Ala Gly Asp Gly Thr Phe Thr Ser Asp Ala Ser Lys Gln Met Glu Glu
1               5                   10                  15

Glu Ala Val Arg Leu Phe Ile Glu Trp Leu Lys Asn
            20                  25

<210> SEQ ID NO 126
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 126

Ala Gly Asp Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 127
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 10 stands for pentylglycine.
<220> FEATURE:
<221> NAME/KEY: AMIDATION -continued
<222> LOCATION: (28)...(28)
<223> OTHER INFORMATION: amidated Asn (Asparaginamide)

<400> SEQUENCE: 127

Ala Gly Asp Gly Thr Phe Thr Ser Asp Xaa Ser Lys Gln Met Glu Glu
1               5                   10                  15

Glu Ala Val Arg Leu Phe Ile Glu Trp Leu Lys Asn
            20                  25

<210> SEQ ID NO 128
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 10 stands for pentylglycine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 128

Ala Gly Asp Gly Thr Phe Thr Ser Asp Xaa Ser Lys Gln Leu Glu Glu
1               5                   10                  15

Glu Ala Val Arg Leu Phe Ile Glu Phe Leu Lys Asn
            20                  25

<210> SEQ ID NO 129
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 129

Ala Gly Asp Gly Thr Phe Thr Ser Asp Leu Ala Lys Gln Met Glu Glu
1               5                   10                  15

Glu Ala Val Arg Leu Phe Ile Glu Trp Leu Lys Asn
            20                  25

<210> SEQ ID NO 130
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 130

Ala Gly Asp Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 131
<211> LENGTH: 28

```
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 131

Ala Gly Asp Gly Thr Phe Thr Ser Asp Leu Ser Ala Gln Met Glu Glu
 1               5                  10                  15

Glu Ala Val Arg Leu Phe Ile Glu Trp Leu Lys Asn
            20                  25

<210> SEQ ID NO 132
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 132

Ala Gly Asp Gly Thr Phe Thr Ser Asp Leu Ser Ala Gln Leu Glu Glu
 1               5                  10                  15

Glu Ala Val Arg Leu Phe Ile Glu Phe Leu Lys Asn
            20                  25

<210> SEQ ID NO 133
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 133

Ala Gly Asp Gly Thr Phe Thr Ser Asp Leu Ser Lys Ala Met Glu Glu
 1               5                  10                  15

Glu Ala Val Arg Leu Phe Ile Glu Trp Leu Lys Asn
            20                  25

<210> SEQ ID NO 134
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 134

Ala Gly Asp Gly Thr Phe Thr Ser Asp Leu Ser Lys Ala Leu Glu Glu
 1               5                  10                  15

Glu Ala Val Arg Leu Phe Ile Glu Phe Leu Lys Asn
```

20                  25

<210> SEQ ID NO 135
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 135

Ala Gly Asp Gly Thr Phe Thr Ser Asp Leu Ser Lys Gln Ala Glu Glu
 1               5                  10                  15

Glu Ala Val Arg Leu Phe Ile Glu Trp Leu Lys Asn
            20                  25

<210> SEQ ID NO 136
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 136

Ala Gly Asp Gly Thr Phe Thr Ser Asp Leu Ser Lys Gln Ala Glu Glu
 1               5                  10                  15

Glu Ala Val Arg Leu Phe Ile Glu Phe Leu Lys Asn
            20                  25

<210> SEQ ID NO 137
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 14 stands for pentylglycine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 137

Ala Gly Asp Gly Thr Phe Thr Ser Asp Leu Ser Lys Gln Xaa Glu Glu
 1               5                  10                  15

Glu Ala Val Arg Leu Phe Ile Glu Trp Leu Lys Asn
            20                  25

<210> SEQ ID NO 138
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 14 stands for pentylglycine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 138

Ala Gly Asp Gly Thr Phe Thr Ser Asp Leu Ser Lys Gln Xaa Glu Glu
1               5                   10                  15

Glu Ala Val Arg Leu Phe Ile Glu Phe Leu Lys Asn
            20                  25

<210> SEQ ID NO 139
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 139

Ala Gly Asp Gly Thr Phe Thr Ser Asp Leu Ser Lys Gln Met Ala Glu
1               5                   10                  15

Glu Ala Val Arg Leu Phe Ile Glu Trp Leu Lys Asn
            20                  25

<210> SEQ ID NO 140
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 140

Ala Gly Asp Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 141
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 141

Ala Gly Asp Gly Thr Phe Thr Ser Asp Leu Ser Lys Gln Met Glu Ala
1               5                   10                  15

Glu Ala Val Arg Leu Phe Ile Glu Trp Leu Lys Asn
            20                  25

<210> SEQ ID NO 142
<211> LENGTH: 28
<212> TYPE: PRT
<213> ORGANISM: Artificial Sequence

```
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 142

Ala Gly Asp Gly Thr Phe Thr Ser Asp Leu Ser Lys Gln Leu Glu Ala
  1               5                  10                  15

Glu Ala Val Arg Leu Phe Ile Glu Phe Leu Lys Asn
             20                  25

<210> SEQ ID NO 143
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 143

Ala Gly Asp Gly Thr Phe Thr Ser Asp Leu Ser Lys Gln Met Glu Glu
  1               5                  10                  15

Ala Ala Val Arg Leu Phe Ile Glu Trp Leu Lys Asn
             20                  25

<210> SEQ ID NO 144
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 144

Ala Gly Asp Gly Thr Phe Thr Ser Asp Leu Ser Lys Gln Leu Glu Glu
  1               5                  10                  15

Ala Ala Val Arg Leu Phe Ile Glu Phe Leu Lys Asn
             20                  25

<210> SEQ ID NO 145
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 145

Ala Gly Asp Gly Thr Phe Thr Ser Asp Leu Ser Lys Gln Met Glu Glu
  1               5                  10                  15

Glu Ala Ala Arg Leu Phe Ile Glu Trp Leu Lys Asn
             20                  25
```

```
<210> SEQ ID NO 146
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 146

Ala Gly Asp Gly Thr Phe Thr Ser Asp Leu Ser Lys Gln Leu Glu Glu
 1               5                  10                  15

Glu Ala Ala Arg Leu Phe Ile Glu Phe Leu Lys Asn
            20                  25

<210> SEQ ID NO 147
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 147

Ala Gly Asp Gly Thr Phe Thr Ser Asp Leu Ser Lys Gln Met Glu Glu
 1               5                  10                  15

Glu Ala Val Ala Leu Phe Ile Glu Trp Leu Lys Asn
            20                  25

<210> SEQ ID NO 148
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 148

Ala Gly Asp Gly Thr Phe Thr Ser Asp Leu Ser Lys Gln Leu Glu Glu
 1               5                  10                  15

Glu Ala Val Ala Leu Phe Ile Glu Phe Leu Lys Asn
            20                  25

<210> SEQ ID NO 149
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 149

Ala Gly Asp Gly Thr Phe Thr Ser Asp Leu Ser Lys Gln Met Glu Glu
```

```
          1               5                  10                 15
Glu Ala Val Arg Ala Phe Ile Glu Trp Leu Lys Asn
            20                  25

<210> SEQ ID NO 150
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 150

Ala Gly Asp Gly Thr Phe Thr Ser Asp Leu Ser Lys Gln Leu Glu Glu
1               5                  10                 15

Glu Ala Val Arg Ala Phe Ile Glu Phe Leu Lys Asn
            20                  25

<210> SEQ ID NO 151
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 22 stands for naphthylalanine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 151

Ala Gly Asp Gly Thr Phe Thr Ser Asp Leu Ser Lys Gln Met Glu Glu
1               5                  10                 15

Glu Ala Val Arg Leu Xaa Ile Glu Trp Leu Lys Asn
            20                  25

<210> SEQ ID NO 152
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 22 stands for naphthylalanine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 152

Ala Gly Asp Gly Thr Phe Thr Ser Asp Leu Ser Lys Gln Leu Glu Glu
1               5                  10                 15

Glu Ala Val Arg Leu Xaa Ile Glu Phe Leu Lys Asn
            20                  25

<210> SEQ ID NO 153
<211> LENGTH: 28
<212> TYPE: PRT
<213> ORGANISM: Artificial Sequence
<220> FEATURE:
<223> OTHER INFORMATION: artificially synthesized sequence of novel
``` exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 153

Ala Gly Asp Gly Thr Phe Thr Ser Asp Leu Ser Lys Gln Met Glu Glu
1               5                   10                  15

Glu Ala Val Arg Leu Phe Val Glu Trp Leu Lys Asn
            20                  25

<210> SEQ ID NO 154
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 154

Ala Gly Asp Gly Thr Phe Thr Ser Asp Leu Ser Lys Gln Leu Glu Glu
1               5                   10                  15

Glu Ala Val Arg Leu Phe Val Glu Phe Leu Lys Asn
            20                  25

<210> SEQ ID NO 155
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 23 stands for tertiary-
      butylglycine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 155

Ala Gly Asp Gly Thr Phe Thr Ser Asp Leu Ser Lys Gln Met Glu Glu
1               5                   10                  15

Glu Ala Val Arg Leu Phe Xaa Glu Trp Leu Lys Asn
            20                  25

<210> SEQ ID NO 156
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in position 23 stands for tertiary-
      butylglycine.
<220> FEATURE:
<221> NAME/KEY: AMIDATION
<222> LOCATION: (28)...(28)
<223> OTHER INFORMATION: amidated Asn (Asparaginamide)

<400> SEQUENCE: 156

Ala Gly Asp Gly Thr Phe Thr Ser Asp Leu Ser Lys Gln Leu Glu Glu
1               5                   10                  15

```
Glu Ala Val Arg Leu Phe Xaa Glu Phe Leu Lys Asn
            20                  25

<210> SEQ ID NO 157
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 157

Ala Gly Asp Gly Thr Phe Thr Ser Asp Leu Ser Lys Gln Met Glu Glu
 1               5                  10                  15

Glu Ala Val Arg Leu Phe Ile Asp Trp Leu Lys Asn
            20                  25

<210> SEQ ID NO 158
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 158

Ala Gly Asp Gly Thr Phe Thr Ser Asp Leu Ser Lys Gln Leu Glu Glu
 1               5                  10                  15

Glu Ala Val Arg Leu Phe Ile Asp Phe Leu Lys Asn
            20                  25

<210> SEQ ID NO 159
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 159

Ala Gly Asp Gly Thr Phe Thr Ser Asp Leu Ser Lys Gln Met Glu Glu
 1               5                  10                  15

Glu Ala Val Arg Leu Phe Ile Glu Ala Leu Lys Asn
            20                  25

<210> SEQ ID NO 160
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)
```

```
<400> SEQUENCE: 160

Ala Gly Asp Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 161
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 161

Ala Gly Asp Gly Thr Phe Thr Ser Asp Leu Ser Lys Gln Met Glu Glu
1               5                   10                  15

Glu Ala Val Arg Leu Phe Ile Glu Trp Ala Lys Asn
            20                  25

<210> SEQ ID NO 162
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 162

Ala Gly Asp Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 163
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 163

Ala Gly Asp Gly Thr Phe Thr Ser Asp Leu Ser Lys Gln Met Glu Glu
1               5                   10                  15

Glu Ala Val Arg Leu Phe Ile Glu Trp Leu Ala Asn
            20                  25

<210> SEQ ID NO 164
<211> LENGTH: 28
<212> TYPE: PRT
<213> ORGANISM: Artificial Sequence
<220> FEATURE:
<223> OTHER INFORMATION: artificially synthesized sequence of novel
``` exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 164

Ala Gly Asp Gly Thr Phe Thr Ser Asp Leu Ser Lys Gln Leu Glu Glu
 1               5                  10                  15

Glu Ala Val Arg Leu Phe Ile Glu Phe Leu Ala Asn
            20                  25

<210> SEQ ID NO 165
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Ala (Alaninamide)

<400> SEQUENCE: 165

Ala Gly Asp Gly Thr Phe Thr Ser Asp Leu Ser Lys Gln Met Glu Glu
 1               5                  10                  15

Glu Ala Val Arg Leu Phe Ile Glu Trp Leu Lys Ala
            20                  25

<210> SEQ ID NO 166
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Ala (Alaninamide)

<400> SEQUENCE: 166

Ala Gly Asp Gly Thr Phe Thr Ser Asp Leu Ser Lys Gln Leu Glu Glu
 1               5                  10                  15

Glu Ala Val Arg Leu Phe Ile Glu Phe Leu Lys Ala
            20                  25

<210> SEQ ID NO 167
<211> LENGTH: 38
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (38)...(38)
<223> OTHER INFORMATION: amidated Pro (Prolinamide)

<400> SEQUENCE: 167

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 168
<211> LENGTH: 38
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (38)...(38)
<223> OTHER INFORMATION: amidated Pro (Prolinamide)

<400> SEQUENCE: 168

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro
         35

<210> SEQ ID NO 169
<211> LENGTH: 37
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (37)...(37)
<223> OTHER INFORMATION: amidated Pro (Prolinamide)

<400> SEQUENCE: 169

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro
         35

<210> SEQ ID NO 170
<211> LENGTH: 36
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (36)...(36)
<223> OTHER INFORMATION: amidated Pro (Prolinamide)

<400> SEQUENCE: 170

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro
         35

<210> SEQ ID NO 171
<211> LENGTH: 36
<212> TYPE: PRT
<213> ORGANISM: Artificial Sequence
<220> FEATURE:

```
<223> OTHER INFORMATION: artificially synthesized sequence of novel
      exendin agonist compound
<220> FEATURE:
<221> NAME/KEY: AMIDATION
<222> LOCATION: (36)...(36)
<223> OTHER INFORMATION: amidated Pro (Prolinamide)

<400> SEQUENCE: 171

Ala Gly Glu Gly Thr Phe Thr Ser Asp Ala Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 172
<211> LENGTH: 35
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (35)...(35)
<223> OTHER INFORMATION: amidated Ala (Alaninamide)

<400> SEQUENCE: 172

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
        35

<210> SEQ ID NO 173
<211> LENGTH: 35
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (35)...(35)
<223> OTHER INFORMATION: amidated Ala (Alaninamide)

<400> SEQUENCE: 173

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala
        35

<210> SEQ ID NO 174
<211> LENGTH: 34
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (34)...(34)
<223> OTHER INFORMATION: amidated Gly (Glycinamide)
```

-continued

```
<400> SEQUENCE: 174

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly

<210> SEQ ID NO 175
<211> LENGTH: 33
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (33)...(33)
<223> OTHER INFORMATION: amidated Ser (Serinamide)

<400> SEQUENCE: 175

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser

<210> SEQ ID NO 176
<211> LENGTH: 32
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (32)...(32)
<223> OTHER INFORMATION: amidated Ser (Serinamide)

<400> SEQUENCE: 176

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

<210> SEQ ID NO 177
<211> LENGTH: 32
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (32)...(32)
<223> OTHER INFORMATION: amidated Ser (Serinamide)

<400> SEQUENCE: 177

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

<210> SEQ ID NO 178
<211> LENGTH: 31
<212> TYPE: PRT
```

```
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (31)...(31)
<223> OTHER INFORMATION: amidated Pro (Prolinamide)

<400> SEQUENCE: 178

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (30)...(30)
<223> OTHER INFORMATION: amidated Gly (Glycinamide)

<400> SEQUENCE: 179

His Gly Glu Gly Thr Phe Thr Ser Ala Leu Ser Lys Gln Leu Glu Glu
 1               5                  10                  15

Glu Ala Val Arg Leu Phe Ile Glu Phe Leu Lys Asn Gly Gly
            20                  25                  30

<210> SEQ ID NO 180
<211> LENGTH: 29
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (29)...(29)
<223> OTHER INFORMATION: amidated Gly (Glycinamide)

<400> SEQUENCE: 180

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly
            20                  25

<210> SEQ ID NO 181
<211> LENGTH: 38
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 31, 36, 37 and 38 stand for
      thioproline.
<220> FEATURE:
<221> NAME/KEY: AMIDATION
<222> LOCATION: (38)...(38)
<223> OTHER INFORMATION: amidated tPro (thioprolinamide)

<400> SEQUENCE: 181

His Gly Ala Gly Thr Phe Thr Ser Asp Leu Ser Lys Gln Met Glu Glu
 1               5                  10                  15
```

-continued

```
Glu Ala Val Arg Leu Phe Ile Glu Trp Leu Lys Asn Gly Gly Xaa Ser
            20                  25                  30

Ser Gly Ala Xaa Xaa Xaa
            35

<210> SEQ ID NO 182
<211> LENGTH: 38
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 36, 37 and 38 stand for
      thioproline.
<220> FEATURE:
<221> NAME/KEY: AMIDATION
<222> LOCATION: (38)...(38)
<223> OTHER INFORMATION: amidated tPro (thioprolinamide)

<400> SEQUENCE: 182

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa
            35

<210> SEQ ID NO 183
<211> LENGTH: 37
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 31, 36 and 37 stands for
      n-methylalanine.
<220> FEATURE:
<221> NAME/KEY: AMIDATION
<222> LOCATION: (37)...(37)
<223> OTHER INFORMATION: amidated Nmeala (n-methylalaninamide)

<400> SEQUENCE: 183

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
            35

<210> SEQ ID NO 184
<211> LENGTH: 36
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<223> OTHER INFORMATION: Xaa in positions 31 and 36 stands for
      homoproline.
<220> FEATURE:
<221> NAME/KEY: AMIDATION
<222> LOCATION: (36)...(36)
<223> OTHER INFORMATION: amidated hPro (homoprolinamide)

<400> SEQUENCE: 184
```

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa
        35

<210> SEQ ID NO 185
<211> LENGTH: 35
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (35)...(35)
<223> OTHER INFORMATION: amidated Ala (Alaninamide)

<400> SEQUENCE: 185

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 186
<211> LENGTH: 30
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (30)...(30)
<223> OTHER INFORMATION: amidated Gly (Glycinamide)

<400> SEQUENCE: 186

His Gly Asp Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 187
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 187

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

-continued

```
<210> SEQ ID NO 188
<211> LENGTH: 39
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (39)...(39)
<223> OTHER INFORMATION: amidated Ser (Serinamide)

<400> SEQUENCE: 188

Ala Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
                20                  25                  30

Ser Gly Ala Pro Pro Pro Ser
            35
```

USE OF EXENDINS FOR THE REDUCTION OF FOOD INTAKE

This application claims the benefit of U.S. Provisional Application No. 60/034,905, filed Jan. 7, 1997, U.S. Provisional Application No. 60/055,404, filed Aug. 8, 1997, U.S. Provisional Application No. 60/066,029 filed Nov. 14, 1997, and U.S. Provisional Application No. 60/065,442, Nov. 14, 1997.

FIELD OF THE INVENTION

The present invention relates to methods for treating conditions or disorders which can be alleviated by reducing food intake comprising administration of an effective amount of an exendin or an exendin agonist alone or in conjunction with other compounds or compositions that affect satiety such as a leptin or an amylin agonist. The methods are useful for treating conditions or disorders, in which the reduction of food intake is of value, including obesity, Type II diabetes, eating disorders, and insulin-resistance syndrome. The methods are also useful for lowering the plasma lipid level, reducing the cardiac risk, reducing the appetite, and reducing the weight of subjects. Pharmaceutical compositions for use in the methods of the invention are also disclosed.

BACKGROUND

The following description summarizes information relevant to the present invention. It is not an admission that any of the information provided herein is prior art to the presently claimed invention, nor that any of the publications specifically or implicitly referenced are prior art to that invention.

Exendin

Exendins are peptides that are found in the venom of the Gila-monster, a lizard found in Arizona, and the Mexican Beaded Lizard. Exendin-3 is present in the venom of *Heloderma horridum*, and exendin-4 is present in the venom of *Heloderma suspectum* (Eng, J., et al., *J. Biol. Chem.*, 265:20259–62, 1990; Eng., J., et al., *J. Biol. Chem.*, 267:7402–05, 1992). The exendins have some sequence similarity to several members of the glucagon-like peptide family, with the highest homology, 53%, being to GLP-1 [7–36]NH$_2$ (Goke, et al., *J. Biol. Chem.*, 268:19650–55, 1993). GLP-1[7–36]NH$_2$, also known as proglucagon [78–107], has an insulinotropic effect, stimulating insulin secretion from pancreatic β-cells; GLP also inhibits glucagon secretion from pancreatic α-cells (Orskov, et al., *Diabetes*, 42:658–61, 1993; D'Alessio, et al., *J. Clin. Invest.*, 97:133–38, 1996). GLP-1 is reported to inhibit gastric emptying (Williams B. et al., *J Clin Endocrinol Metab* 81 (1): 327–32, 1996; Wettergren A, et al., *Dig Dis Sci* 38 (4): 665–73, 1993), and gastric acid secretion. (Schjoldager B T, et al., *Dig Dis Sci* 34 (5): 703–8, 1989; O'Halloran D J, et al., *J Endocrinol* 126 (1): 169–73, 1990; Wettergren A, et al., *Dig Dis Sci* 38 (4): 665–73, 1993). GLP-1[7–37], which has an additional glycine residue at its carboxy terminus, also stimulates insulin secretion in humans (Orskov, et al., *Diabetes*, 42:658–61, 1993). A transmembrane G-protein adenylate-cyclase-coupled receptor believed to be responsible for the insulinotropic effect of GLP-1 is reported to have been cloned from a β-cell line (Thorens, Proc. Natl. Acad. Sci. USA 89:8641–45 (1992)).

Exendin-4 potently binds at GLP-1 receptors on insulin-secreting βTC1 cells, at dispersed acinar cells from guinea pig pancreas, and at parietal cells from stomach; the peptide is also said to stimulate somatostatin release and inhibit gastrin release in isolated stomachs (Goke, et al., *J. Biol. Chem.* 268:19650–55, 1993; Schepp, et al., *Eur. J. Pharmacol.*, 69:183–91, 1994; Eissele, et al., *Life Sci.*, 55:629–34, 1994). Exendin-3 and exendin-4 were reported to stimulate cAMP production in, and amylase release from, pancreatic acinar cells (Malhotra, R., et al., *Regulatory Peptides*, 41:149–56, 1992; Raufman, et al., *J. Biol. Chem.* 267:21432–37, 1992; Singh, et al., *Regul. Pept.* 53:47–59, 1994). The use of exendin-3 and exendin-4 as insulinotrophic agents for the treatment of diabetes mellitus and the prevention of hyperglycemia has been proposed (Eng, U.S. Pat. No. 5,424,286).

C-terminally truncated exendin peptides such as exendin [9–39], a carboxyamidated molecule, and fragments 3–39 through 9–39 have been reported to be potent and selective antagonists of GLP-1 (Goke, et al., *J. Biol. Chem.*, 268:19650–55, 1993; Raufman, J. P., et al., *J. Biol. Chem.* 266:2897–902, 1991; Schepp, W., et al., *Eur. J. Pharm.* 269:183–91, 1994; Montrose-Rafizadeh, et al., *Diabetes*, 45(Suppl. 2):152A, 1996). Exendin[9–39] is said to block endogenous GLP-1 in vivo, resulting in reduced insulin secretion. Wang, et al., *J. Clin. Invest.*, 95:417–21, 1995; D'Alessio, et al., *J. Clin. Invest.*, 97:133–38, 1996). The receptor apparently responsible for the insulinotropic effect of GLP-1 has reportedly been cloned from rat pancreatic islet cell (Thorens, B., *Proc. Natl. Acad. Sci. USA* 89:8641–8645, 1992). Exendins and exendin[9–39] are said to bind to the cloned GLP-1 receptor (rat pancreatic β-cell GLP-1 receptor (Fehmann H C, et al., *Peptides* 15 (3): 453–6, 1994) and human GLP-1 receptor (Thorens B, et al., *Diabetes* 42 (11): 1678–82, 1993). In cells transfected with the cloned GLP-1 receptor, exendin-4 is reportedly an agonist, i.e., it increases cAMP, while exendin[9–39] is identified as an antagonist, i.e., it blocks the stimulatory actions of exendin-4 and GLP-1. Id.

Exendin[9–39] is also reported to act as an antagonist of the full length exendins, inhibiting stimulation of pancreatic acinar cells by exendin-3 and exendin-4 (Raufman, et al., *J. Biol. Chem.* 266:2897–902, 1991; Raufman, et al., *J. Biol. Chem.*, 266:21432–37, 1992). It is also reported that exendin [9–39] inhibits the stimulation of plasma insulin levels by exendin-4, and inhibits the somatostatin release-stimulating and gastrin release-inhibiting activities of exendin-4 and GLP-1 (Kolligs, F., et al., *Diabetes*, 44:16–19, 1995; Eissele, et al., *Life Sciences*, 55:629–34, 1994).

Exendins have recently been found to inhibit gastric emptying (U.S. Ser. No. 08/694,954, filed Aug. 8, 1996, which enjoys common ownership with the present invention and is hereby incorporated by reference).

Exendin [9–39] has been used to investigate the physiological relevance of central GLP-1 in control of food intake (Turton, M. D. et al. *Nature* 379:69–72, 1996). GLP-1 administered by intracerebroventricular injection inhibits food intake in rats. This satiety-inducing effect of GLP-1 delivered ICV is reported to be inhibited by ICV injection of exendin [9–39] (Turton, supra). However, it has been reported that GLP-1 does not inhibit food intake in mice when administered by peripheral injection (Turton, M. D., *Nature* 379:69–72, 1996; Bhavsar, S. P., *Soc. Neurosci. Abstr.* 21:460 (188.8), 1995).

Obesity and Hypernutrition

Obesity, excess adipose tissue, is becoming increasingly prevalent in developed societies. For example, approximately 30% of adults in the U.S. were estimated to be 20 percent above desirable body weight—an accepted measure of obesity sufficient to impact a health risk (*Harrison's Principles of Internal Medicine* 12th Edition, McGraw Hill, Inc. (1991) p. 411). The pathogenesis of obesity is believed to be multifactorial but the basic problem is that in obese subjects food intake and energy expenditure do not come into balance until there is excess adipose tissue. Attempts to reduce food intake, or hypernutrition, are usually fruitless in the medium term because the weight loss induced by dieting results in both increased appetite and decreased energy expenditure (Leibel et al., (1995) *New England Journal of Medicine* 322: 621–628). The intensity of physical exercise required to expend enough energy to materially lose adipose mass is too great for most people to undertake on a sufficiently frequent basis. Thus, obesity is currently a poorly treatable, chronic, essentially intractable metabolic disorder. Not only is obesity itself believed by some to be undesirable for cosmetic reasons, but obesity also carries serious risk of co-morbidities including, Type 2 diabetes, increased cardiac risk, hypertension, atherosclerosis, degenerative arthritis, and increased incidence of complications of surgery involving general anesthesia. Obesity due to hypernutrition is also a risk factor for the group of conditions called insulin resistance syndrome, or "syndrome X." In syndrome X, it has been reported that there is a linkage between insulin resistance and hypertension. (Watson N. and Sandler M., *Curr. Med. Res. Opin.*, 12(6):374–378 (1991); Kodama J. et al., *Diabetes Care*, 13(11):1109–1111 (1990); Lithell et al., *J. Cardiovasc. Pharmacol.*, 15 Suppl. 5:S46–S52 (1990)).

In those few subjects who do succeed in losing weight, by about 10 percent of body weight, there can be striking improvements in co-morbid conditions, most especially Type 2 diabetes in which dieting and weight loss are the primary therapeutic modality, albeit relatively ineffective in many patients for the reasons stated above. Reducing food intake in obese subjects would decrease the plasma glucose level, the plasma lipid level, and the cardiac risk in these subjects. Hypernutrition is also the result of, and the psychological cause of, many eating disorders. Reducing food intake would also be beneficial in the treatment of such disorders.

Thus, it can be appreciated that an effective means to reduce food intake is a major challenge and a superior method of treatment would be of great utility. Such a method, and compounds and compositions which are useful therefor, have been invented and are described and claimed herein.

SUMMARY OF THE INVENTION

The present invention concerns the surprising discovery that exendins and exendin agonists have a profound and prolonged effect on inhibiting food intake.

The present invention is directed to novel methods for treating conditions or disorders associated with hypernutrition, comprising the administration of an exendin, for example, exendin-3 [SEQ ID NO. 1: His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser], or exendin-4 [SEQ ID NO. 2: His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser], or other compounds which effectively bind to the receptor at which exendin exerts its action on reducing food intake. These methods will be useful in the treatment of, for example, obesity, diabetes, including Type II or non-insulin dependent diabetes, eating disorders, and insulin-resistance syndrome.

In a first aspect, the invention features a method of treating conditions or disorders which can be alleviated by reducing food intake in a subject comprising administering to the subject a therapeutically effective amount of an exendin or an exendin agonist. By an "exendin agonist" is meant a compound that mimics the effects of exendin on the reduction of food intake by binding to the receptor or receptors where exendin causes this effect. Preferred exendin agonist compounds include those described in U.S. Provisional Patent Application Serial No. 60/055,404, entitled, "Novel Exendin Agonist Compounds," filed Aug. 8, 1997; U.S. Provisional Patent Application Serial No. 60/065,442, entitled, "Novel Exendin Agonist Compounds," filed Nov. 14, 1997; and U.S. Provisional Patent Application Serial No. 60/066,029, entitled, "Novel Exendin Agonist Compounds," filed Nov. 14, 1997; all of which enjoy common ownership with the present application and all of which are incorporated by this reference into the present application as though fully set forth herein. By "condition or disorder which can be alleviated by reducing food intake" is meant any condition or disorder in a subject that is either caused by, complicated by, or aggravated by a relatively high food intake, or that can be alleviated by reducing food intake. Such conditions or disorders include, but are not limited to, obesity, diabetes, including Type II diabetes, eating disorders, and insulin-resistance syndrome.

Thus, in a first embodiment, the present invention provides a method for treating conditions or disorders which can be alleviated by reducing food intake in a subject comprising administering to said subject a therapeutically effective amount of an exendin or an exendin agonist. Preferred exendin agonist compounds include those described in U.S. Provisional Patent Application Serial Nos. 60/055,404; 60/065,442; and 60/066,029, which have been incorporated by reference in the present application. Preferably, the subject is a vertebrate, more preferably a mammal, and most preferably a human. In preferred aspects, the exendin or exendin agonist is administered parenterally, more preferably by injection. In a most preferred aspect, the injection is a peripheral injection. Preferably, about 10 $\mu$g–30 $\mu$g to about 5 mg of the exendin or exendin agonist is administered per day. More preferably, about 10–30 $\mu$g to about 2 mg, or about 10–30 $\mu$g to about 1 mg of the exendin or exendin agonist is administered per day. Most preferably, about 30 $\mu$g to about 500 $\mu$g of the exendin or exendin agonist is administered per day.

In various preferred embodiments of the invention, the condition or disorder is obesity, diabetes, preferably Type II diabetes, an eating disorder, or insulin-resistance syndrome.

In other preferred aspects of the invention, a method is provided for reducing the appetite of a subject comprising administering to said subject an appetite-lowering amount of an exendin or an exendin agonist.

In yet other preferred aspects, a method is provided for lowering plasma lipids comprising administering to said subject a therapeutically effective amount of an exendin or an exendin agonist.

The methods of the present invention may also be used to reduce the cardiac risk of a subject comprising administering to said subject a therapeutically effective amount of an exendin or an exendin agonist. In one preferred aspect, the exendin or exendin agonist used in the methods of the present invention is exendin-3. In another preferred aspect, said exendin is exendin-4. Other preferred exendin agonists include exendin-4 (1–30) [SEQ ID NO 6: His Gly Glu Gly Thr Phe Thr Ser Asp Leu Ser Lys Gln Met Glu Glu Glu Ala Val Arg Leu Phe Ile Glu Trp Leu Lys Asn Gly Gly], exendin-4 (1–30) amide [SEQ ID NO 7: His Gly Glu Gly Thr Phe Thr Ser Asp Leu Ser Lys Gln Met Glu Glu Glu Ala Val Arg Leu Phe Ile Glu Trp Leu Lys Asn Gly Gly-NH$_2$], exendin-4 (1–28) amide [SEQ ID NO 40: His Gly Glu Gly Thr Phe Thr Ser Asp Leu Ser Lys Gln Met Glu Glu Glu Ala Val Arg Leu Phe Ile Glu Trp Leu Lys Asn-NH$_2$], [14]Leu, [25]Phe exendin-4 amide [SEQ ID NO 9: His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-NH$_2$], [14]Leu, [25]Phe exendin-4 (1–28) amide [SEQ ID NO 41: His Gly Glu Gly Thr Phe Thr Ser Asp Leu Ser Lys Gln Leu Glu Glu Glu Ala Val Arg Leu Phe Ile Glu Phe Leu Lys Asn-NH$_2$], and [14]Leu, [22]Ala, [25]Phe exendin-4 (1–28) amide [SEQ ID NO 8: His Gly Glu Gly Thr Phe Thr Ser Asp Leu Ser Lys Gln Leu Glu Glu Glu Ala Val Arg Leu Ala Ile Glu Phe Leu Lys Asn-NH$_2$].

In the methods of the present invention, the exendins and exendin agonists may be administered separately or together with one or more other compounds and compositions that exhibit a long term or short-term satiety action, including, but not limited to other compounds and compositions that comprise an amylin agonist, cholecystokinin (CCK), or a leptin (ob protein). Suitable amylin agonists include, for example, [[25,28,29]Pro-]-human amylin (also known as "pramlintide," and previously referred to as "AC-137") as described in "Amylin Agonist Peptides and Uses Therefor," U.S. Pat. No. 5,686,511, issued Nov. 11, 1997, and salmon calcitonin. The CCK used is preferably CCK octopeptide (CCK-8). Leptin is discussed in, for example, Pelleymounter, M. A., et al. *Science* 269:540–43 (1995); Halaas, J. L., et al. *Science* 269:543–46 (1995); and Campfield, L. A., et al. *Eur. J. Pharmac.* 262:133–41 (1994).

In other embodiments of the invention is provided a pharmaceutical composition for use in the treatment of conditions or disorders which can be alleviated by reducing food intake comprising a therapeutically effective amount of an exendin or exendin agonist in association with a pharmaceutically acceptable carrier. Preferably, the pharmaceutical composition comprises a therapeutically effective amount for a human subject.

The pharmaceutical composition may preferably be used for reducing the appetite of a subject, reducing the weight of a subject, lowering the plasma lipid level of a subject, or reducing the cardiac risk of a subject. Those of skill in the art will recognize that the pharmaceutical composition will preferably comprise a therapeutically effective amount of an exendin or exendin agonist to accomplish the desired effect in the subject.

The pharmaceutical compositions may further comprise one or more other compounds and compositions that exhibit a long-term or short-term satiety action, including, but not limited to other compounds and compositions that comprise an amylin agonist, CCK, preferably CCK-8, or leptin. Suitable amylin agonists include, for example, [[25,28,29]Pro]-human amylin and salmon calcitonin.

In one preferred aspect, the pharmaceutical composition comprises exendin-3. In another preferred aspect, the pharmaceutical composition comprises exendin-4. In other preferred aspects, the pharmaceutical compositions comprises a peptide selected from: exendin-4 (1–30), exendin-4 (1–30) amide, exendin-4 (1–28) amide, [14]Leu, [25]Phe exendin-4 amide, [14]Leu, [25]Phe exendin-4 (1–28) amide, and [14]Leu, [22]Ala, [25]Phe exendin-4 (1–28) amide.

BRIEF DESCRIPTION OF THE DRAWINGS

FIGS. 10A–10B depict the amino acid sequences for certain exendin agonist compounds useful in the present invention [SEQ ID NOS 3–39].

DETAILED DESCRIPTION OF THE INVENTION

Figure 1:
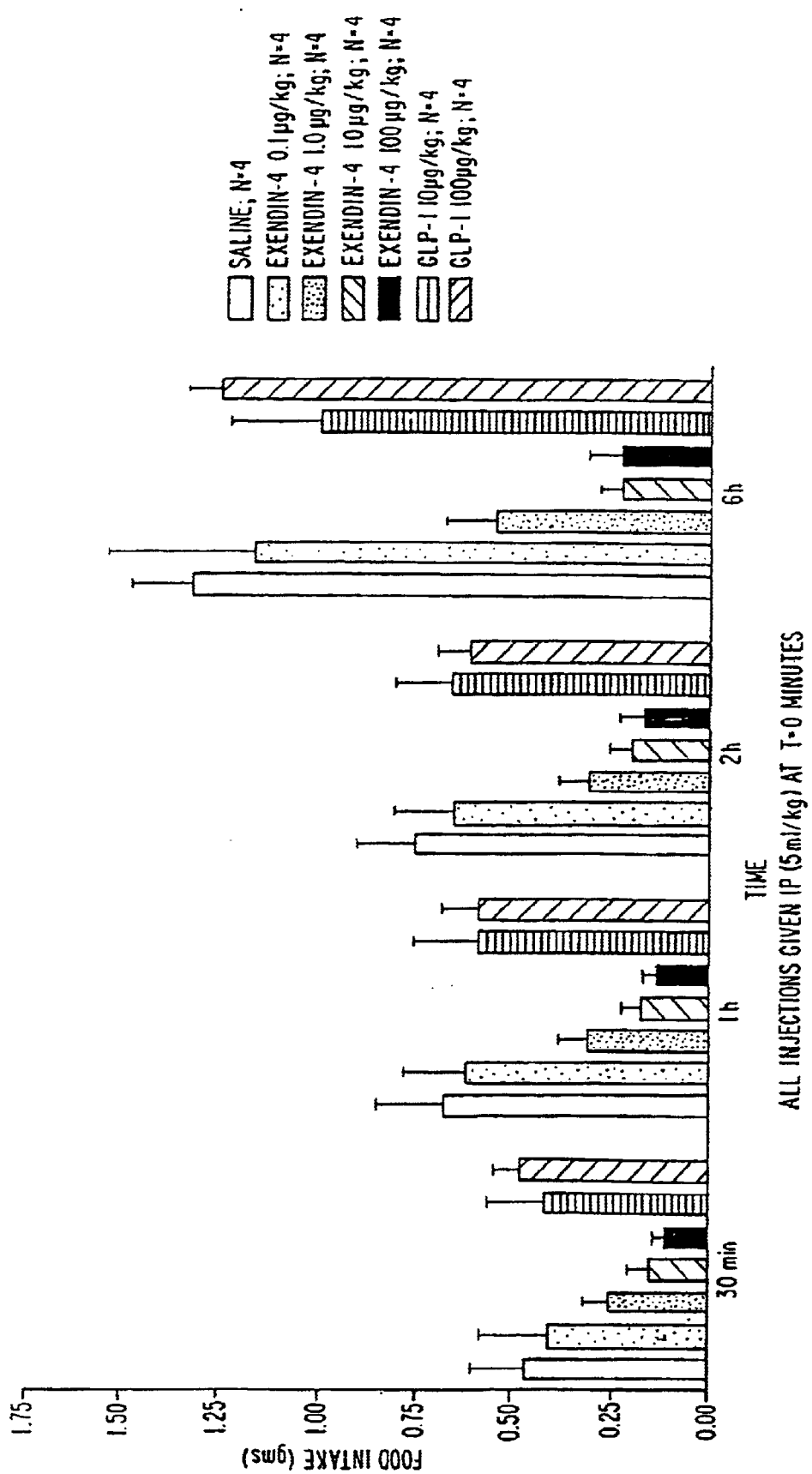
FIG. 1 is a graphical depiction of the change of food intake in normal mice after intraperitoneal injection of exendin-4 and GLP-1.

Exendins and exendin agonists are useful as described herein in view of their pharmacological properties. Activity as exendin agonists can be indicated by activity in the assays described below. Effects of exendins or exendin agonists on reducing food intake can be identified, evaluated, or screened for, using the methods described in the Examples below, or other methods known in the art for determining effects on food intake or appetite.

Exendin Agonist Compounds

Exendin agonist compounds are those described in U.S. Provisional Application No. 60/055,404, including compounds of the formula (I) [SEQ ID NO. 3]:

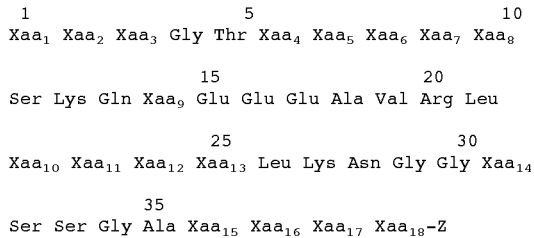

wherein Xaa$_1$ is His, Arg or Tyr; Xaa$_2$ is Ser, Gly, Ala or Thr; Xaa$_3$ is Asp or Glu; Xaa$_4$ is Phe, Tyr or naphthylalanine; Xaa$_5$ is Thr or Ser; Xaa$_6$ is Ser or Thr; Xaa$_7$ is Asp or Glu; Xaa$_8$ is Leu, Ile, Val, pentylglycine or Met; Xaa$_9$ is Leu, Ile, pentylglycine, Val or Met; Xaa$_{10}$ is Phe, Tyr or naphthylalanine; Xaa$_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —NH$_2$; with the proviso that the compound is not exendin-3 or exindin-4.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds include those listed in FIG. 10 having amino acid sequences of SEQ. ID. NOS. 9 to 39.

Preferred exendin agonist compounds include those wherein $Xaa_1$ is His or Tyr. More preferably $Xaa_1$ is His.

Preferred are those compounds wherein $Xaa_2$ is Gly.

Preferred are those compounds wherein $Xaa_9$ is Leu, pentylglycine or Met.

Preferred compounds include those wherein $Xaa_{13}$ is Trp or Phe.

Also preferred are compounds where $Xaa_4$ is Phe or naphthylalanine; $Xaa_{11}$ is Ile or Val and $Xaa_{14}$, $Xaa_{15}$, $Xaa_{16}$ and $Xaa_{17}$ are independently selected from Pro, homoproline, thioproline or N-alkylalanine. Preferably N-alkylalanine has a N-alkyl group of 1 to about 6 carbon atoms.

According to an especially preferred aspect, $Xaa_{15}$, $Xaa_{16}$ and $Xaa_{17}$ are the same amino acid reside.

Preferred are compounds wherein $Xaa_{18}$ is Ser or Tyr, more preferably Ser.

Preferably Z is —NH$_2$.

According to one aspect, preferred are compounds of formula (I) wherein $Xaa_1$ is His or Tyr, more preferably His; $Xaa_2$ is Gly; $Xaa_4$ is Phe or naphthylalanine; $Xaa_9$ is Leu, pentylglycine or Met; $Xaa_{10}$ is Phe or naphthylalanine; $Xaa_{11}$ is Ile or Val; $Xaa_{14}$, $Xaa_{15}$, $Xaa_{16}$ and $Xaa_{17}$ are independently selected from Pro, homoproline, thioproline or N-alkylalanine; and $Xaa_{18}$ is Ser or Tyr, more preferably Ser. More preferably Z is —NH$_2$.

According to an especially preferred aspect, especially preferred compounds include those of formula (I) wherein: $Xaa_1$ is His or Arg; $Xaa_2$ is Gly; $Xaa_3$ is Asp or Glu; $Xaa_4$ is Phe or napthylalanine; $Xaa_5$ is Thr or Ser; $Xaa_6$ is Ser or Thr; $Xaa_7$ is Asp or Glu; $Xaa_8$ is Leu or pentylglycine; $Xaa_9$ is Leu or pentylglycine; $Xaa_{10}$ is Phe or naphthylalanine; $Xaa_{11}$ is Ile, Val or t-butyltylglycine; $Xaa_{12}$ is Glu or Asp; $Xaa_{13}$ is Trp or Phe; $Xaa_{14}$, $Xaa_{15}$, $Xaa_{16}$, and $Xaa_{17}$ are independently Pro, homoproline, thioproline, or N-methylalanine; $Xaa_{18}$ is Ser or Tyr: and Z is —OH or —NH$_2$; with the proviso that the compound does not have the formula of either SEQ. ID. NOS. 1 or 2. More preferably Z is —NH$_2$. Especially preferred compounds include those having the amino acid sequence of SEQ. ID. NOS. 9, 10, 21, 22, 23, 26, 28, 34, 35 and 39.

According to an especially preferred aspect, provided are compounds where $Xaa_9$ is Leu, Ile, Val or pentylglycine, more preferably Leu or pentylglycine, and $Xaa_{13}$ is Phe, Tyr or naphthylalanine, more preferably Phe or naphthylalanine. These compounds will exhibit advantageous duration of action and be less subject to oxidative degration, both in vitro and in vivo, as well as during synthesis of the compound.

Exendin agonist compounds also include those described in U.S. Provisional Application No. 60/065,442, including compounds of the formula (II) [SEQ ID NO. 4]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$$Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg or Tyr;

$Xaa_2$ is Ser, Gly, Ala or Thr;

$Xaa_3$ is Asp or Glu;

$Xaa_5$ is Ala or Thr;

$Xaa_6$ is Ala, Phe, Tyr or naphthylalanine;

$Xaa_7$ is Thr or Ser;

$Xaa_8$ is Ala, Ser or Thr;

$Xaa_9$ is Asp or Glu;

$Xaa_{10}$ is Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{14}$ is Ala, Leu, Ile, pentylglycine, Val or Met;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala or Leu;

$Xaa_{22}$ is Phe, Tyr or naphthylalanine;

$Xaa_{23}$ is Ile, Val, Leu, pentylglycine, tert-butylglycine or Met;

$Xaa_{24}$ is Ala, Glu or Asp;

$Xaa_{25}$ is Ala, Trp, Phe, Tyr or naphthylalanine;

$Xaa_{26}$ is Ala or Leu;

$Xaa_{27}$ is Ala or Lys;

$Xaa_{28}$ is Ala or Asn;

$Z_1$ is —OH,
—NH$_2$
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{36}$-$Z_2$,
Gly Gly $Xaa_{31}$ Ser Ser Gly Ala $Xaa_{36}$ $Xaa_{37}$-$Z_2$ or
Gly Gly $Xaa_{31}$ Ser Ser Gly Ala $Xaa_{36}$ $Xaa_{37}$ $Xaa_{38}$-$Z_2$;
$Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and
$Z_2$ is —OH or —NH$_2$;
provided that no more than three of $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Preferred N-alkyl groups for N-alkylglycine, N-alkylpentylglycine and N-alkylalanine include lower alkyl groups preferably of 1 to about 6 carbon atoms, more preferably of 1 to 4 carbon atoms.

Preferred exendin agonist compounds include those wherein $Xaa_1$ is His or Tyr. More preferably $Xaa_1$ is His.

Preferred are those compounds wherein $Xaa_2$ is Gly.

Preferred are those compounds wherein $Xaa_{14}$ is Leu, pentylglycine or Met.

Preferred compounds are those wherein $Xaa_{25}$ is Trp or Phe.

Preferred compounds are those where $Xaa_6$ is Phe or naphthylalanine; $Xaa_{22}$ is Phe or naphthylalanine and $Xaa_{23}$ is Ile or Val.

Preferred are compounds wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —$NH_2$.

Preferable $Z_2$ is —$NH_2$.

According to one aspect, preferred are compounds of formula (I) wherein $Xaa_1$ is His or Tyr, more preferably His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. More preferably $Z_1$ is —$NH_2$.

According to an especially preferred aspect, especially preferred compounds include those of formula (I) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or nephthylalaine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Especially preferred compounds include those having the amino acid sequence of SEQ. ID. NOS. 40–61.

According to an especially preferred aspect, provided are compounds where $Xaa_{14}$ is Leu, Ile, Val or pentylglycine, more preferably Leu or pentylglycine, and $Xaa_{25}$ is Phe, Tyr or naphthylalanine, more preferably Phe or naphthylalanine. These compounds will be less susceptive to oxidative degration, both in vitro and in vivo, as well as during synthesis of the compound.

Exendin agonist compounds also include those described in U.S. Provisional Application No. 60/066,029, including compounds of the formula (III)[SEQ ID NO. 5]:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg, Tyr, Ala, Norval, Val or Norleu;

$Xaa_2$ is Ser, Gly, Ala or Thr;

$Xaa_3$ is Ala, Asp or Glu;

$Xaa_4$ is Ala, Norval, Val, Norleu or Gly;

$Xaa_5$ is Ala or Thr;

$Xaa_6$ is Phe, Tyr or naphthylalanine;

$Xaa_7$ is Thr or Ser;

$Xaa_8$ is Ala, Ser or Thr;

$Xaa_9$ is Ala, Norval, Val, Norleu, Asp or Glu;

$Xaa_{10}$ is Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{14}$ is Ala, Leu, Ile, pentylglycine, Val or Met;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala or Leu;

$Xaa_{22}$ is Phe, Tyr or naphthylalanine;

$Xaa_{23}$ is Ile, Val, Leu, pentylglycine, tert-butylglycine or Met;

$Xaa_{24}$ is Ala, Glu or Asp;

$Xaa_{25}$ is Ala, Trp, Phe, Tyr or naphthylalanine;

$Xaa_{26}$ is Ala or Leu;

$Xaa_{27}$ is Ala or Lys;

$Xaa_{28}$ is Ala or Asn;

$Z_1$ is —OH,
—$NH_2$,
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{13}$-$Z_2$,
Gly Gly $Xaa_{31}$ Ser Ser Gly Ala $Xaa_{36}$ $Xaa_{37}$-$Z_2$,
Gly Gly $Xaa_{31}$ Ser Ser Gly Ala $Xaa_{36}$ $Xaa_{37}$ $Xaa_{31}$-$Z_2$
or Gly Gly $Xaa_{31}$ Ser Ser Gly Ala $Xaa_{36}$ $Xaa_{37}$ $Xaa_{38}$ $Xaa_{39}$-$Z_2$; wherein $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and $Z_2$ is —OH or —$NH_2$;

provided that no more than three of $Xaa_3$, $Xaa_4$, $Xaa_5$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala.

Definitions

In accordance with the present invention and as used herein, the following terms are defined to have the following meanings, unless explicitly stated otherwise.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is an amino acid side chain, typically H or a carbon containing substitutent; or (2),

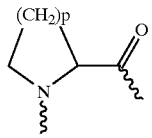

wherein p is 1, 2 or 3 representing the azetidinecarboxylic acid, proline or pipecolic acid residues, respectively.

The term "lower" referred to herein in connection with organic radicals such as alkyl groups defines such groups with up to and including about 6, preferably up to and including 4 and advantageously one or two carbon atoms. Such groups may be straight chain or branched chain.

"Pharmaceutically acceptable salt" includes salts of the compounds described herein derived from the combination of such compounds and an organic or inorganic acid. In practice the use of the salt form amounts to use of the base form. The compounds are useful in both free base and salt form.

In addition, the following abbreviations stand for the following:

"ACN" or "CH$_3$CN" refers to acetonitrile.

"Boc", "tBoc" or "Tboc" refers to t-butoxy carbonyl.

"DCC" refers to N,N'-dicyclohexylcarbodiimide.

"Fmoc" refers to fluorenylmethoxycarbonyl.

"HBTU" refers to 2-(1H-benzotriazol-1-yl)-1,1,3,3,-tetramethyluronium hexaflurophosphate.

"HOBt" refers to 1-hydroxybenzotriazole monohydrate.

"homoP" or "hPro" refers to homoproline.

"MeAla" or "Nme" refers to N-methylalanine.

"naph" refers to naphthylalanine.

"pG" or "pGly" refers to pentylglycine.

"tBuG" refers to tertiary-butylglycine.

"ThioP" or "tPro" refers to thioproline.

3Hyp" refers to 3-hydroxyproline

4Hyp" refers to 4-hydroxyproline

NAG" refers to N-alkylglycine

NAPG" refers to N-alkylpentylglycine

"Norval" refers to norvaline

"Norleu" refers to norleucine

Preparation of Compounds

The exendins and exendin agonists described herein may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu (Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20–24 h). Hydrolysates may be derivatized and analyzed by standard methods (Cohen, et al., *The Pico Tag Method: A Manual of Advanced Techniques for Amino Acid Analysis*, pp. 11–52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried out on a VG-Trio machine.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989). Non-peptide compounds useful in the present invention may be prepared by art-known methods. For example, phosphate-containing amino acids and peptides containing such amino acids, may be prepared using methods known in the art. See, e.g., Bartlett and Landen, *Biorg. Chem.* 14:356–377 (1986).

The compounds described above are useful in view of their pharmacological properties. In particular, the compounds of the invention possess activity as agents to reduce food intake. They can be used to treat conditions or diseases which can be alleviated by reducing food intake.

Compositions useful in the invention may conveniently be provided in the form of formulations suitable for parenteral (including intravenous, intramuscular and subcutaneous) or nasal or oral administration. In some cases, it will be convenient to provide an exendin or exendin agonist and another food-intake-reducing, plasma glucose-lowering or plasma lipid-lowering agent, such as amylin, an amylin agonist, a CCK, or a leptin, in a single composition or solution for administration together. In other cases, it may be more advantageous to administer the additional agent separately from said exendin or exendin agonist. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 3.0 to 8.0, preferably at a pH of about 3.5 to 5.0. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The claimed compositions can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, transmucosally, or by pulmonary inhalation.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an exendin or exendin agonist, for example, exendin-3, and/or exendin-4, with or without another food intake-reducing, plasma glucose-lowering or plasma lipid-lowering agent. Therapeutically effective amounts of an exendin or exendin agonist for use in reducing food intake are those that suppress appetite at a desired level. As will be recognized by those in the field, an effective amount of therapeutic agent will vary with many factors including the age and weight of the patient, the patient's physical condition, the blood sugar level and other factors.

The effective daily appetite-suppressing dose of the compounds will typically be in the range of about 10 to 30 µg to about 5 mg/day, preferably about 10 to 30 µg to about 2 mg/day and more preferably about 10 to 100 µg to about 1 mg/day, most preferably about 30 µg to about 500 µg/day, for a 70 kg patient, administered in a single or divided doses. The exact dose to be administered is determined by the attending clinician and is dependent upon where the particular compound lies within the above quoted range, as well as upon the age, weight and condition of the individual. Administration should begin whenever the suppression of food intake, or weight lowering is desired, for example, at the first sign of symptoms or shortly after diagnosis of obesity, diabetes mellitus, or insulin-resistance syndrome. Administration may be by injection, preferably subcutaneous or intramuscular. Orally active compounds may be taken orally, however dosages should be increased 5–10 fold.

The optimal formulation and mode of administration of compounds of the present application to a patient depend on factors known in the art such as the particular disease or disorder, the desired effect, and the type of patient. While the compounds will typically be used to treat human subjects they may also be used to treat similar or identical diseases in other vertebrates such as other primates, farm animals such as swine, cattle and poultry, and sports animals and pets such as horses, dogs and cats.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Exendin Injections Reduced the Food Intake of Normal Mice

All mice (NIH:Swiss mice) were housed in a stable environment of 22 (±2)° C., 60 (±10)% humidity and a 12:12 light:dark cycle; with lights on at 0600. Mice were housed in groups of four in standard cages with ad libitum access to food (Teklad: LM 485; Madison, Wis.) and water except as noted, for at least two weeks before the experiments.

All experiments were conducted between the hours of 0700 and 0900. The mice were food deprived (food removed at 1600 hr from all animals on day prior to experiment) and individually housed. All mice received an intraperitoneal injection (5 µl/kg) of either saline or exendin-4 at doses of 0.1, 1.0, 10 and 100 µg/kg and were immediately presented with a pre-weighed food pellet (Teklad LM 485). The food pellet was weighed at 30-minute, 1-hr, 2-hr and 6-hr intervals to determine the amount of food eaten.

FIG. 1 depicts cumulative food intake over periods of 0.5, 1, 2 and 6 hr in overnight-fasted normal NIH:Swiss mice following ip injection of saline, 2 doses of GLP-1, or 4 doses of exendin-4. At doses up to 100 µg/kg, GLP-1 had no effect on food intake measured over any period, a result consistent with that previously reported (Bhavsar, S. P., et al., *Soc. Neurosci. Abstr.* 21:460 (188.8) (1995); and Turton, M. D., *Nature*, 379:69–72, (1996)).

In contrast, exendin-4 injections potently and dose-dependently inhibited food intake. The $ED_{50}$ for inhibition of food intake over 30 min was 1 µg/kg, which is a level about as potent as amylin ($ED_{50}$ 3.6 µg/kg) or the proto-typical peripheral satiety agent, CCK ($ED_{50}$ 0.97 µg/kg) as measured in this preparation. However, in contrast to the effects of amylin or CCK, which abate after 1–2 hours, the inhibition of food intake with exendin-4 was still present after at least 6 hours after injection.

EXAMPLE 2

Exendin Reduced the Food Intake of Obese Mice

All mice (female ob/ob mice) were housed in a stable environment of 22 (±2)° C., 60 (±10)% humidity and a 12:12 light:dark cycle; with lights on at 0600. Mice were housed in groups of four in standard cages with ad libitum access to food (Teklad: LM 485) and water except as noted, for at least two weeks before the experiments.

All experiments were conducted between the hours of 0700 and 0900. The mice were food deprived (food removed at 1600 hr from all animals on day prior to experiment) and individually housed. All mice received an intraperitoneal injection (5 µl/kg) of either saline or exendin-4 at doses of 0.1, 1.0 and 10 µg/kg (female ob/ob mice) and were immediately presented with a pre-weighed food pellet (Teklad LM 485). The food pellet was weighed at 30-minute, 1-hr, 2-hr and 6-hr intervals to determine the amount of food eaten.

Figure 2:
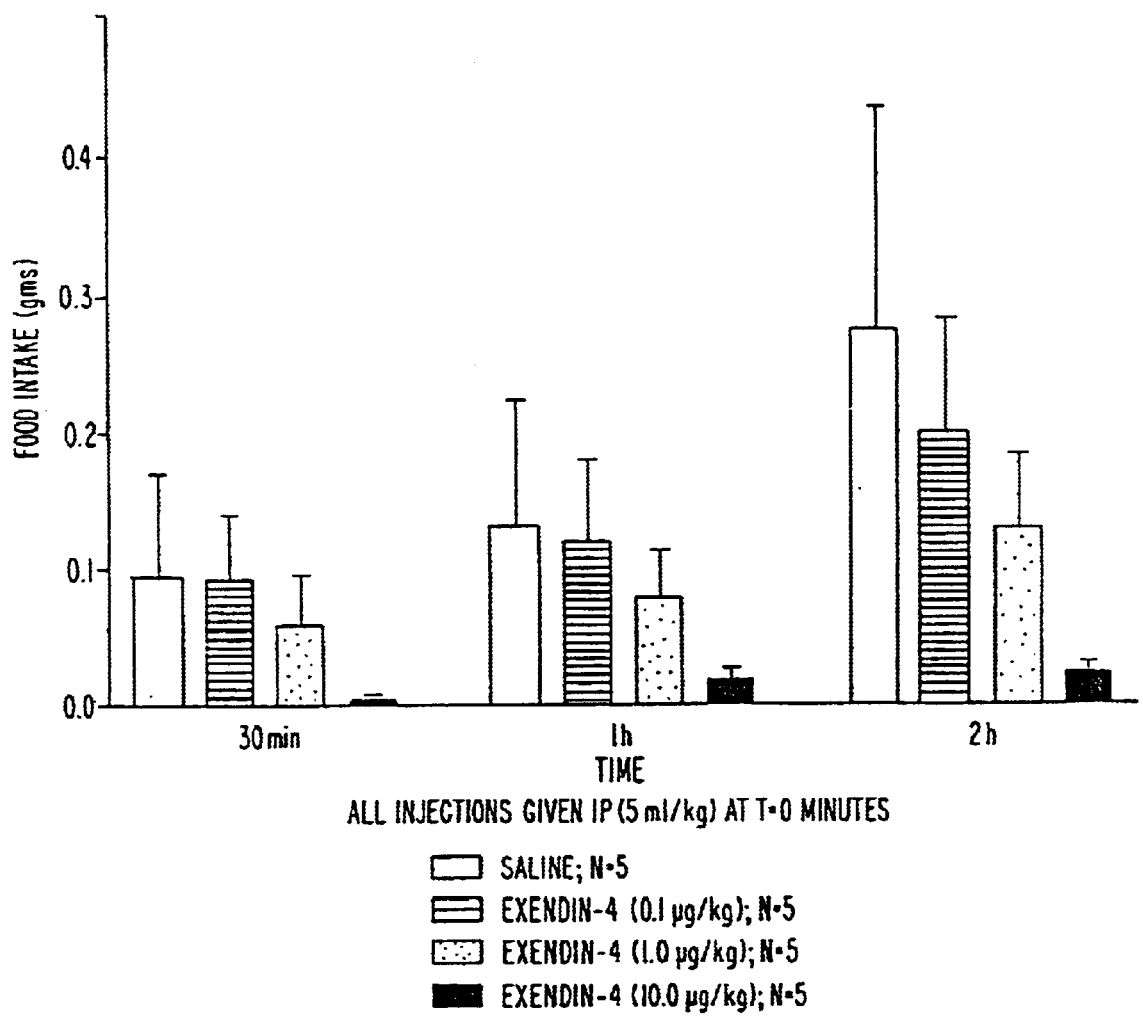
FIG. 2 is a graphical depiction of the change of food intake in obese mice after intraperitoneal injection of exendin-4.

FIG. 2 depicts the effect of exendin-4 in the ob/ob mouse model of obesity. The obese mice had a similar food intake-related response to exendin as the normal mice. Moreover, the obese mice were not hypersensitive to exendin, as has been observed with amylin and leptin (Young, A. A., et al., *Program and Abstracts*, 10th International Congress of Endocrinology, Jun. 12–15, 1996 San Francisco, pg 419 (P2–58)).

EXAMPLE 3

Intracerebroventricular Injections of Exendin Inhibited Food Intake in Rats

All rats (Harlan Sprague-Dawley) were housed in a stable environment of 22 (±2)° C., 60 (±10)% humidity and a 12:12 light:dark cycle; with lights on at 0600. Rats were obtained from Zivic Miller with an intracerebroventricular cannula (ICV cannula) implanted (coordinates determined by actual weight of animals and referenced to Paxinos, G. and Watson, C. "The Rat Brain in stereotaxic coordinates," second edition. Academic Press) and were individually housed in standard cages with ad libitum access to food (Teklad: LM 485) and water for at least one week before the experiments.

All injections were given between the hours of 1700 and 1800. The rats were habituated to the ICV injection procedure at least once before the ICV administration of compound. All rats received an ICV injection (2 µl/30 seconds) of either saline or exendin-4 at doses of 0.01, 0.03, 0.1, 0.3, and 1.0 µg. All animals were then presented with pre-weighed food (Teklad LM 485) at 1800, when the lights were turned off. The amount of food left was weighed at 2-hr, 12-hr and 24-hr intervals to determine the amount of food eaten by each animal.

Figure 3:
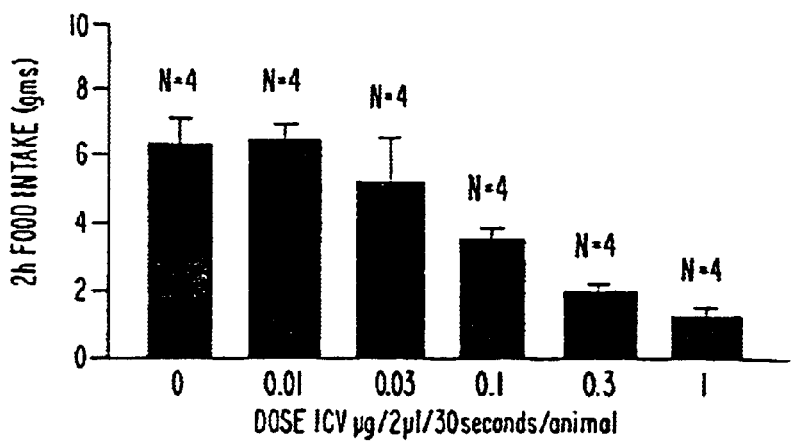
FIG. 3 is a graphical depiction of the change of food intake in rats after intracerebroventricular injection of exendin-4
Figure 3:
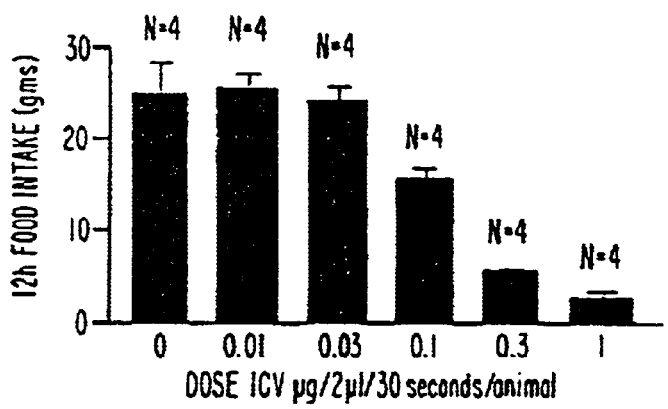
Figure 3:
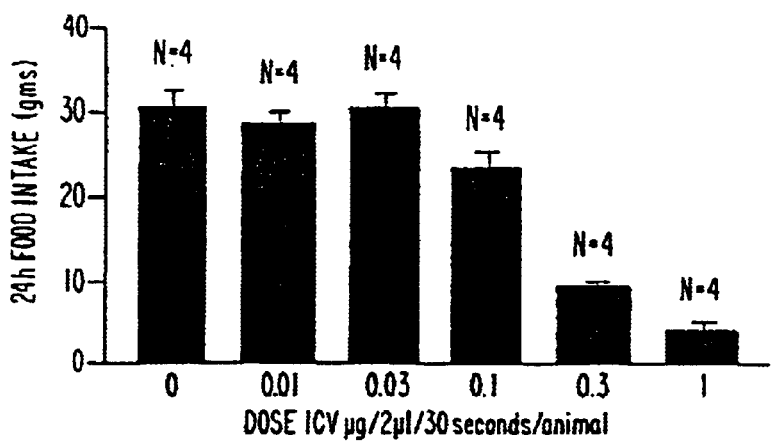

FIG. 3 depicts a dose-dependent inhibition of food intake in rats that received doses greater than 0.1 µg/rat. The $ED_{50}$ was ≈0.1 µg, exendin-4 is thus ≈100-fold more potent than intracerebroventricular injections of GLP-1 as reported by Turton, M. D., et al. (*Nature* 379:69–72 (1996)).

EXAMPLE 4

Exendin Agonists Reduced the Food Intake in Mice

All mice (NIH:Swiss mice) were housed in a stable environment of 22 (±2)° C., 60 (±10)% humidity and a 12:12 light:dark cycle; with lights on at 0600. Mice were housed in groups of four in standard cages with ad libitum access to food (Teklad: LM 485; Madison, Wis.) and water except as noted, for at least two weeks before the experiments.

All experiments were conducted between the hours of 0700 and 0900. The mice were food deprived (food removed at 1600 hr from all animals on day prior to experiment) and individually housed. All mice received an intraperitoneal injection (5 μl/kg) of either saline or test compound at doses of 1, 10, and 100 μg/kg and immediately presented with a food pellet (Teklad LM 485). The food pellet was weighed at 30-minute, 1-hr, 2-hr and 6-hr intervals to determine the amount of food eaten.

Figure 4:
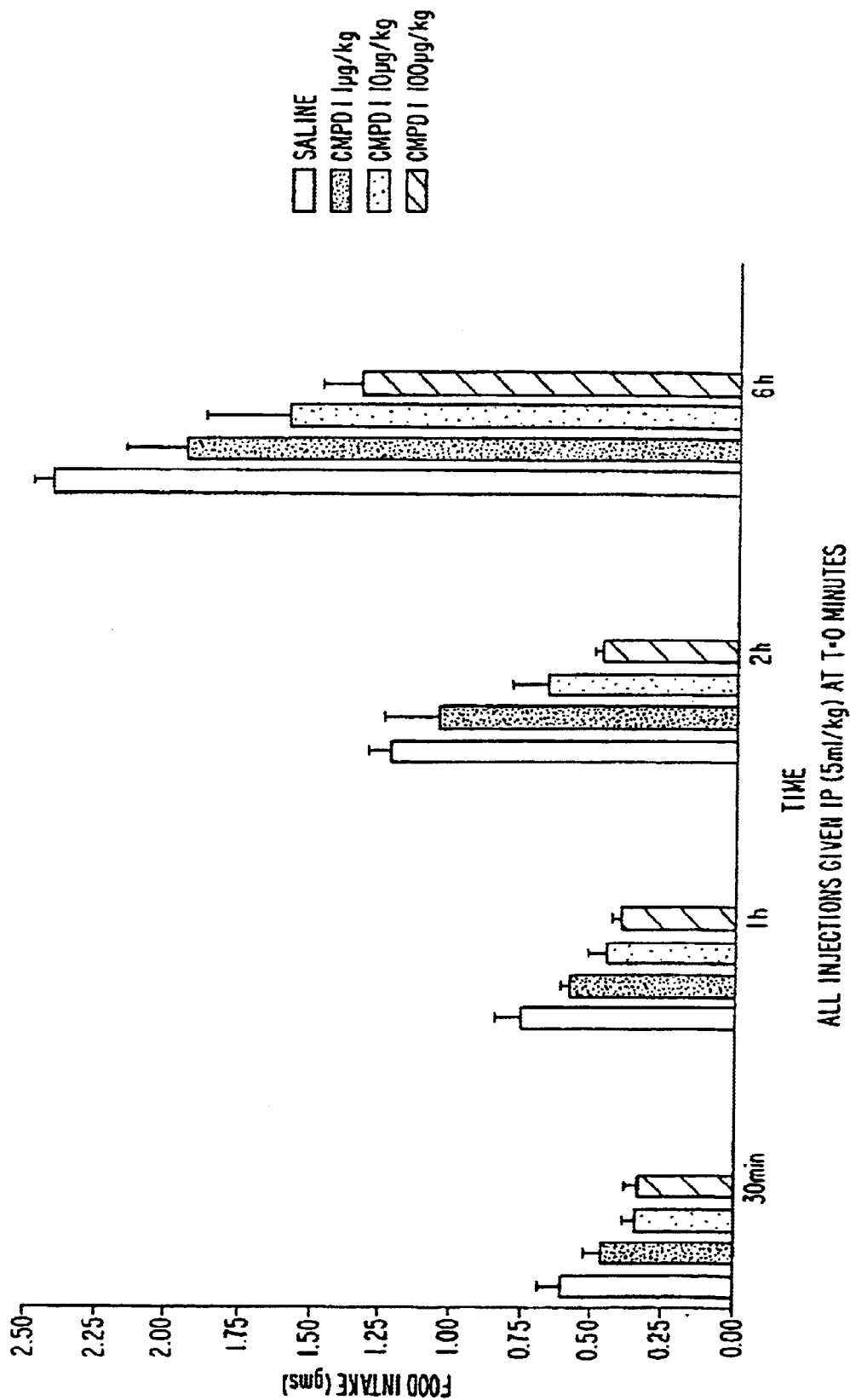
FIG. 4 is a graphical depiction of the change of food intake in normal mice after intraperitoneal injection of exendin-4 (1–30) ("Compound 1").

FIG. 4 depicts the cumulative food intake over periods of 0.5, 1, 2 and 6 hr in overnight-fasted normal NIH:Swiss mice following ip injection of saline or exendin-4 (1–30) ("Compound 1") in doses of 1, 10 and 100 μg/kg.

Figure 5:
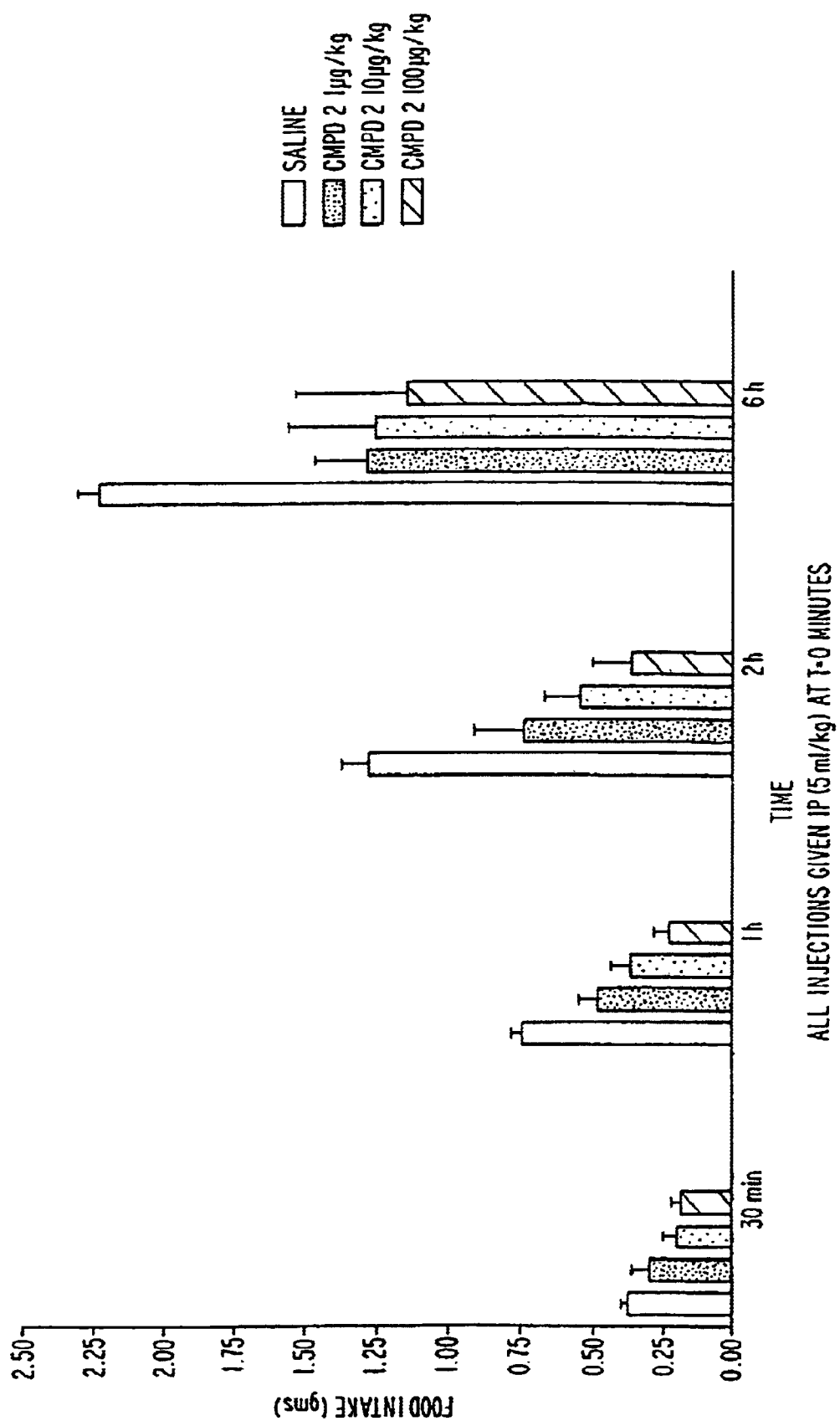
FIG. 5 is a graphical depiction of the change of food intake in normal mice after intraperitoneal injection of exendin-4 (1–30) amide ("Compound 2").

FIG. 5 depicts the cumulative food intake over periods of 0.5, 1, 2 and 6 hr in overnight-fasted normal NIH:Swiss mice following ip injection of saline or exendin-4 (1–30) amide ("Compound 2") in doses of 1, 10 and 100 μg/kg.

Figure 6:
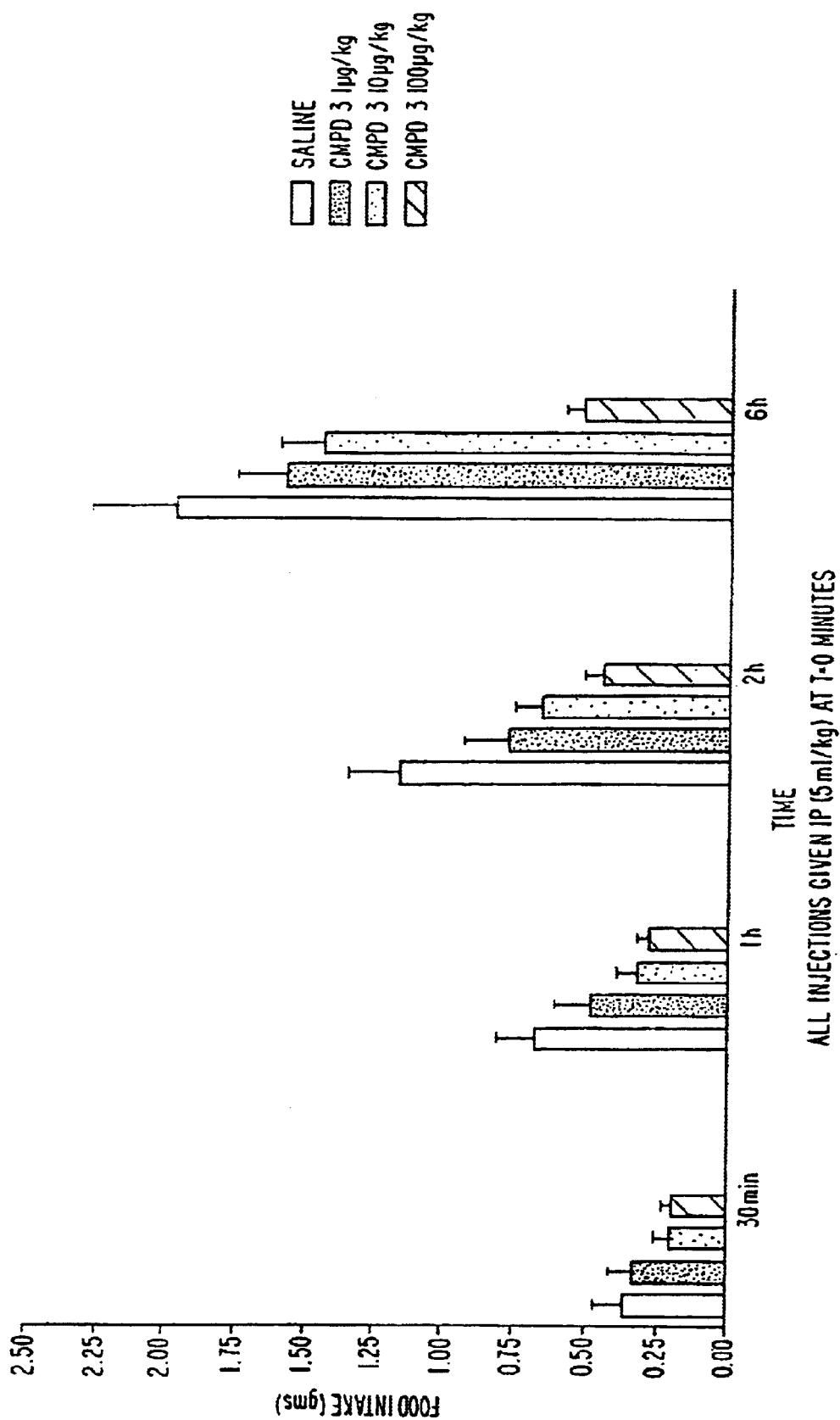
FIG. 6 is a graphical depiction of the change of food intake in normal mice after intraperitoneal injection of exendin-4 (1–28) amide ("Compound 3").

FIG. 6 depicts the cumulative food intake over periods of 0.5, 1, 2 and 6 hr in overnight-fasted normal NIH:Swiss mice following ip injection of saline or exendin-4 (1–28) amide ("Compound 3") in doses of 1, 10 and 100 μg/kg.

Figure 7:
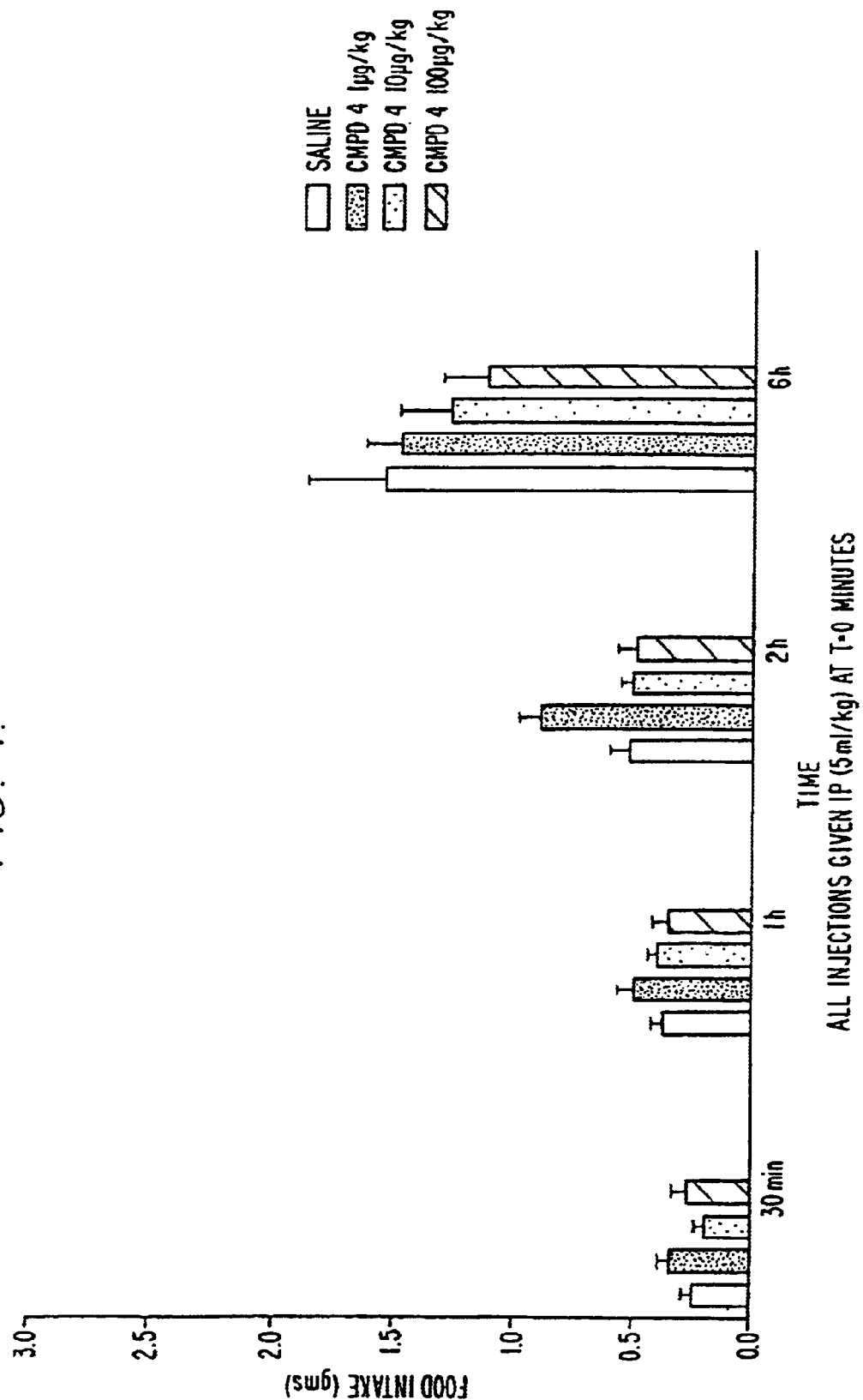
FIG. 7 is a graphical depiction of the change of food intake in normal mice after intraperitoneal injection of [4]Leu, [25]Phe exendin-4 amide ("Compound 41").

FIG. 7 depicts the cumulative food intake over periods of 0.5, 1, 2 and 6 hr in overnight-fasted normal NIH:Swiss mice following ip injection of saline or $^{14}$Leu, $^{25}$Phe exendin-4 amide ("Compound 41") in doses of 1, 10 and 100 μg/kg.

Figure 8:
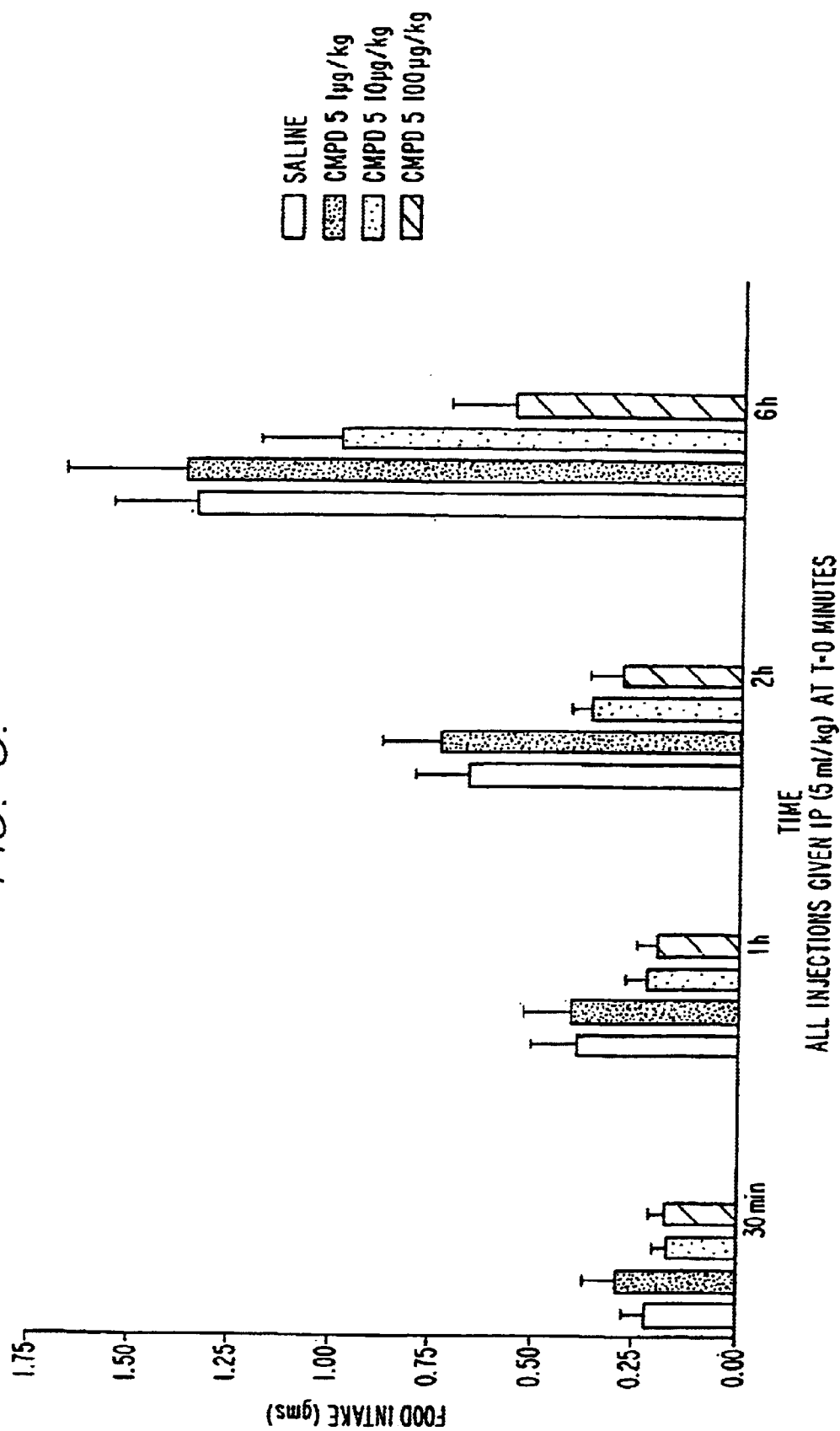
FIG. 8 is a graphical depiction of the change of food intake in normal mice after intraperitoneal injection of [4]Leu, [25]Phe exendin-4 (1–28) amide ("Compound 5").

FIG. 8 depicts the cumulative food intake over periods of 0.5, 1, 2 and 6 hr in overnight-fasted normal NIH:Swiss mice following ip injection of saline or $^{14}$Leu, $^{25}$Phe exendin-4 (1–28) amide ("Compound 5") in doses of 1, 10 and 100 μg/kg.

Figure 9:
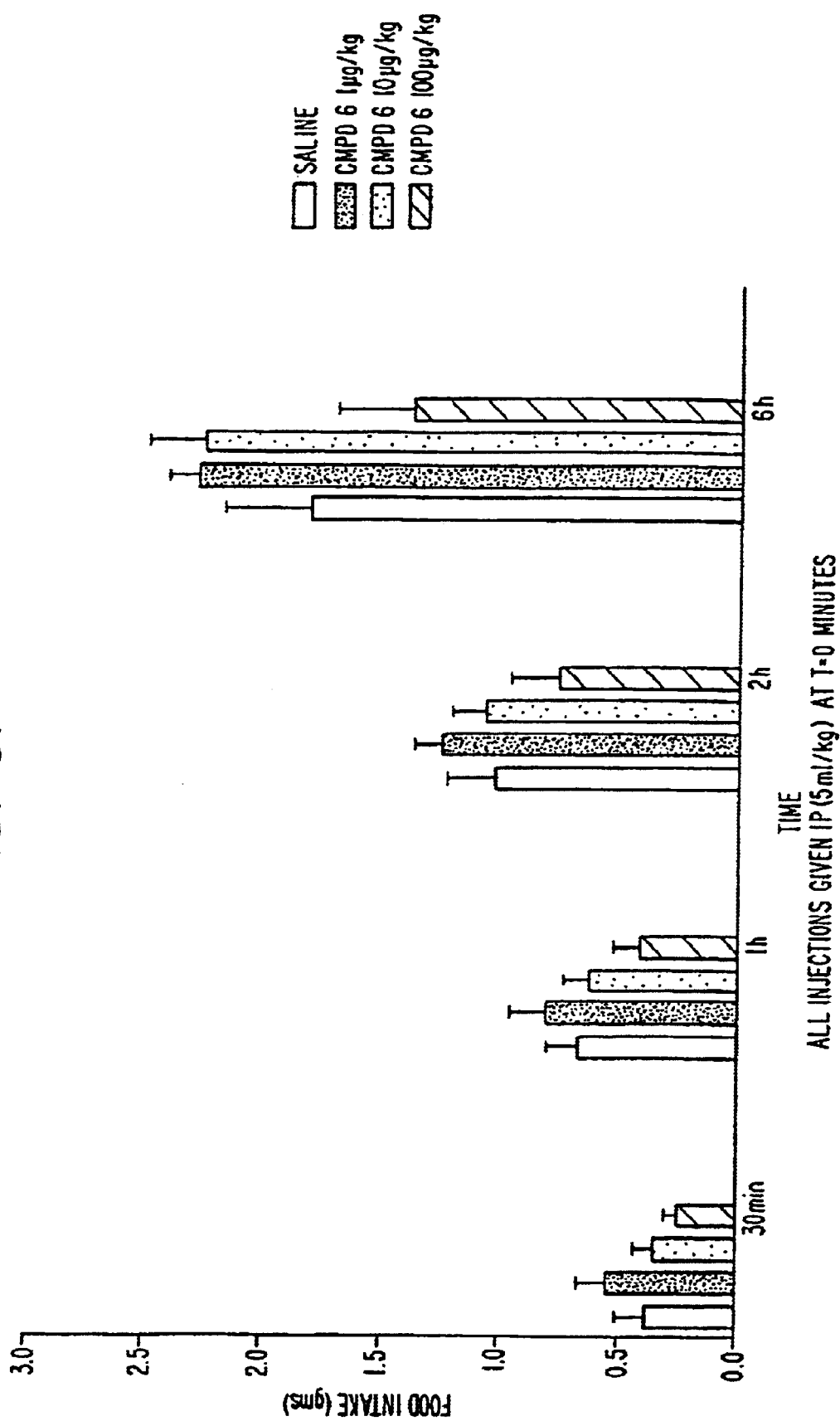
FIG. 9 is a graphical depiction of the change of food intake in normal mice after intraperitoneal injection of [14]Leu, [22]Ala, [25]Phe exendin-4 (1–28) amide ("Compound 6").

FIG. 9 depicts the cumulative food intake over periods of 0.5, 1, 2 and 6 hr in overnight-fasted normal NIH:Swiss mice following ip injection of saline or $^{14}$Leu, $^{22}$Ala, $^{25}$Phe exendin-4 (1–28) amide ("Compound 6") in doses of 1, 10 and 100 μg/kg.

EXAMPLE 5

Preparation of Amidated Peptide having SEQ. ID. NO. 9

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. However, at some positions coupling was less efficient than expected and double couplings were required. In particular, residues $Asp_9$, $Thr_7$ and $Phe_6$ all required double coupling. Deprotection (Fmoc group removal) of the growing peptide chain using piperidine was not always efficient. Double deprotection was required at positions $Arg_{20}$, $Val_{19}$ and $Leu_{14}$. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 55%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 60% Solvent B in Solvent A over 30 minutes) of the lyophilized peptide gave product peptide having an observed retention time of 14.5 minutes. Electrospray Mass Spectrometry (M): calculated 4131.7; found 4129.3.

EXAMPLE 6

Preparation of Peptide having SEQ. ID. NO. 10

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis were Solvent A (0.1% TFA in water) and Solvent B (0.1% TFA in ACN). Analytical RP-HPLC (gradient 25% to 75% Solvent B in Solvent A over 30 minutes) of the lyophilized peptide gave product peptide having an observed retention time of 21.5 minutes. Electrospray Mass Spectrometry (M): calculated 4168.6; found 4171.2.

EXAMPLE 7

Preparation of Peptide having SEQ. ID. NO. 11

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis were Solvent A (0.1% TFA in water) and Solvent B (0.1% TFA in ACN). Analytical RP-HPLC (gradient 30% to 60% Solvent B in Solvent A over 30 minutes) of the lyophilized peptide gave product peptide having an observed retention time of 17.9 minutes. Electrospray Mass Spectrometry (M): calculated 4147.6; found 4150.2.

EXAMPLE 8

Preparation of Peptide having SEQ. ID. NO. 12

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis were Solvent A (0.1% TFA in water) and Solvent B (0.1% TFA in ACN). Analytical RP-HPLC (gradient 35% to 65% Solvent B in Solvent A over 30 minutes) of the lyophilized peptide gave product peptide having an observed retention time of 19.7 minutes. Electrospray Mass Spectrometry (M): calculated 4212.6; found 4213.2.

EXAMPLE 9

Preparation of Peptide having SEQ. ID. NO. 13

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis were Solvent A (0.1% TFA in water) and Solvent B (0.1% TFA in ACN). Analytical RP-HPLC (gradient 30% to 50% Solvent B in Solvent A over 30 minutes) of the lyophilized peptide gave product peptide having an observed retention time of 16.3 minutes. Electrospray Mass Spectrometry (M): calculated 4262.7; found 4262.4.

EXAMPLE 10

Preparation of Peptide having SEQ. ID. NO. 14

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6

EXAMPLE 11

Preparation of Peptide having SEQ. ID. NO. 15

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4224.7.

EXAMPLE 12

Preparation of Peptide having SEQ. ID. NO. 16

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 13

Preparation of Peptide having SEQ. ID. NO. 17

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4186.6.

EXAMPLE 14

Preparation of Peptide having SEQ. ID. NO. 18

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4200.7.

EXAMPLE 15

Preparation of Peptide having SEQ. ID. NO. 19

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4200.7.

EXAMPLE 16

Preparation of Peptide having SEQ. ID. NO. 20

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4202.7.

EXAMPLE 17

Preparation of Peptide having SEQ. ID. NO. 21

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 18

Preparation of Peptide having SEQ. ID. NO. 22

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4184.6.

EXAMPLE 19

Preparation of Peptide having SEQ. ID. NO. 23

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 20

Preparation of Peptide having SEQ. ID. NO. 24

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4224.7.

EXAMPLE 21

Preparation of Peptide having SEQ. ID. NO. 25

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 22

Preparation of Peptide having SEQ. ID. NO. 26

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4115.5.

EXAMPLE 23

Preparation of Peptide having SEQ. ID. NO. 27

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4188.6.

EXAMPLE 24

Preparation of Peptide having SEQ. ID. NO. 28

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4131.6.

EXAMPLE 25

Preparation of Peptide having SEQ. ID. NO. 29

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 26

Preparation of Peptide having SEQ. ID. NO. 30

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 27

Preparation of Peptide having SEQ. ID. NO. 31

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Additional double couplings are required at the thioproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4266.8.

EXAMPLE 28

Preparation of Peptide having SEQ. ID. NO. 32

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Additional double couplings are required at the thioproline positions 38, 37 and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4246.8.

EXAMPLE 29

Preparation of Peptide having SEQ. ID. NO. 33

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Additional double couplings are required at the homoproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4250.8.

EXAMPLE 30

Preparation of Peptide having SEQ. ID. NO. 34

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Additional double couplings are required at the homoproline positions 38, 37, and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4234.8.

EXAMPLE 31

Preparation of Peptide having SEQ. ID. NO. 35

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Additional double couplings are required at the thioproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4209.8.

EXAMPLE 32

Preparation of Peptide having SEQ. ID. NO. 36

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Additional double couplings are required at the homoproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4193.7.

EXAMPLE 33

Preparation of Peptide having SEQ. ID. NO. 37

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Additional double couplings are required at the N-methylalanine positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3858.2.

EXAMPLE 34

Preparation of Peptide having SEQ. ID. NO. 38

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Additional double couplings are required at the N-methylalanine positions 38, 37 and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3940.3.

EXAMPLE 35

Preparation of Peptide having SEQ. ID. NO. 39

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 5. Additional double couplings are required at the N-methylalanine positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3801.1.

EXAMPLE 36

Preparation of C-Terminal Carboxylic Acid Peptides Corresponding to the Above C-Terminal Amide Sequences The above peptides of Examples 5 to 35 are assembled on the so called Wang resin (p-alkoxybenzylalacohol resin (Bachem, 0.54 mmole/g)) using Fmoc-protected amino acids (Applied Biosystems, Inc.), cleaved from the resin, deprotected and purified in a similar way to Example 5. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLE 37

Preparation of Peptide having SEQ ID NO. 7
His Gly Glu Gly Thr Phe Thr Ser Asp Leu Ser Lys Gln Met Glu Glu Glu Ala Val Arg Leu Phe Ile Glu Trp Leu Lys Asn Gly Gly-NH$_2$ [SEQ. ID. NO. 7]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN). The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 50% Solvent B in Solvent A over 30 minutes) of the lyophilized peptide gave product peptide having an observed retention time of 18.9 minutes. Electrospray Mass Spectrometry (M): calculated 3408.0; found 3408.9.

EXAMPLE 38

Preparation of Peptide having SEQ ID NO. 40
His Gly Glu Gly Thr Phe Thr Ser Asp Leu Ser Lys Gln Met Glu Glu Glu Ala Val Arg Leu Phe Ile Glu Trp Leu Lys Asn-NH$_2$ [SEQ. ID. NO. 40]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 30% to 40% Solvent B in Solvent A over 30 minutes) of the lyophilized peptide gave product peptide having an observed retention time of 17.9 minutes. Electrospray Mass Spectrometry (M): calculated 3294.7; found 3294.8.

EXAMPLE 39

Preparation of Peptide having SEQ ID NO. 41
His Gly Glu Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 41]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 29% to 36% Solvent B in Solvent A over 30 minutes) of the lyophilized peptide gave product peptide having an observed retention time of 20.7 minutes. Electrospray Mass Spectrometry (M) calculated 3237.6; found 3240.

EXAMPLE 40

Preparation of Peptide having SEQ ID NO. 42
His Ala Glu Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 42]

The above amidated peptide was assembled on 4-(2'-4'-dimethoxyphenyl)-Fmoc aminomethyl phenoxy acetamide

27 norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 15.2 minutes. Electrospray Mass Spectrometry (M): calculated 3251.6; found 3251.5.

EXAMPLE 41

Preparation of Peptide having SEQ ID NO. 43
His Gly Glu Gly Ala Phe Thr Ser Asp Leu Ser Lys Gln Leu Glu Glu Glu Ala Val Arg Leu Phe Ile Glu Phe Leu Lys Asn-NH$_2$ [SEQ. ID. NO. 43]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 13.1 minutes. Electrospray Mass Spectrometry (M): calculated 3207.6; found 3208.3.

EXAMPLE 42

Preparation of Peptide having SEQ ID NO. 44
His Gly Glu Gly Thr Ala Thr Ser Asp Leu Ser Lys Gln Leu Glu Glu Glu Ala Val Arg Leu Phe Ile Glu Phe Leu Lys Asn-NH$_2$ [SEQ. ID. NO. 44]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 12.8 minutes. Electrospray Mass Spectrometry (M): calculated 3161.5; found 3163.

EXAMPLE 43

Preparation of Peptide having SEQ ID NO. 45
His Gly Glu Gly Thr Phe Thr Ala Asp Leu Ser Lys Gln Leu Glu Glu Glu Ala Val Arg Leu Phe Ile Glu Phe Leu Lys Asn-NH$_2$ [SEQ. ID. NO. 45]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 15.2 minutes. Electrospray Mass Spectrometry (M): calculated 3221.6; found 3222.7.

28

EXAMPLE 44

Preparation of Peptide having SEQ ID NO. 46
His Gly Glu Gly Thr Phe Thr Ser Asp Ala Ser Lys Gln Leu Glu Glu Glu Ala Val Arg Leu Phe Ile Glu Phe Leu Lys Asn-NH$_2$ [SEQ. ID. NO. 46]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 34% to 44% Solvent B in Solvent A over 30 minutes) of the lyophilized peptide gave product peptide having an observed retention time of 14.3 minutes. Electrospray Mass Spectrometry (M): calculated 3195.5; found 3199.4.

EXAMPLE 45

Preparation of Peptide having SEQ ID NO. 47
His Gly Glu Gly Thr Phe Thr Ser Asp Leu Ala Lys Gln Leu Glu Glu Glu Ala Val Arg Leu Phe Ile Glu Phe Leu Lys Asn-NH$_2$ [SEQ. ID. NO. 47]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 15.7 minutes. Electrospray Mass Spectrometry (M): calculated 3221.6; found 3221.6.

EXAMPLE 46

Preparation of Peptide having SEQ ID NO. 48
His Gly Glu Gly Thr Phe Thr Ser Asp Leu Ser Ala Gln Leu Glu Glu Glu Ala Val Arg Leu Phe Ile Glu Phe Leu Lys Asn-NH$_2$ [SEQ. ID. NO. 48]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 18.1 minutes. Electrospray Mass Spectrometry (M): calculated 3180.5; found 3180.9.

EXAMPLE 47

Preparation of Peptide having SEQ ID NO. 49
His Gly Glu Gly Thr Phe Thr Ser Asp Leu Ser Lys Ala Leu Glu Glu Glu Ala Val Arg Leu Phe Ile Glu Phe Leu Lys Asn-NH$_2$ [SEQ. ID. NO. 49]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 17.0 minutes. Electrospray Mass Spectrometry (M): calculated 3180.6; found 3182.8.

EXAMPLE 48

Preparation of Peptide having SEQ ID NO. 50
His Gly Glu Gly Thr Phe Thr Ser Asp Leu Ser Lys Gln Ala Glu Glu Glu Ala Val Arg Leu Phe Ile Glu Phe Leu Lys Asn-$NH_2$ [SEQ. ID. NO. 50]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 14.9 minutes. Electrospray Mass Spectrometry (M): calculated 3195.5; found 3195.9.

EXAMPLE 49

Preparation of Peptide having SEQ ID NO. 51
His Gly Glu Gly Thr Phe Thr Ser Asp Leu Ser Lys Gln Leu Ala Glu Glu Ala Val Arg Leu Phe Ile Glu Phe Leu Lys Asn-$NH_2$ [SEQ. ID. NO. 51]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 17.9 minutes. Electrospray Mass Spectrometry (M): calculated 3179.6; found 3179.0.

EXAMPLE 50

Preparation of Peptide having SEQ ID NO. 52
His Gly Glu Gly Thr Phe Thr Ser Asp Leu Ser Lys Gln Leu Glu Ala Glu Ala Val Arg Leu Phe Ile Glu Phe Leu Lys Asn-$NH_2$ [SEQ. ID. NO. 52]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 14.3 minutes. Electrospray Mass Spectrometry (M): calculated 3179.6; found 3180.0.

EXAMPLE 51

Preparation of Peptide having SEQ ID NO. 53
His Gly Glu Gly Thr Phe Thr Ser Asp Leu Ser Lys Gln Leu Glu Glu Ala Ala Val Arg Leu Phe Ile Glu Phe Leu Lys Asn-$NH_2$ [SEQ. ID. NO. 53]

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 13.7 minutes. Electrospray Mass Spectrometry (M): calculated 3179.6; found 3179.0.

EXAMPLE 52

Preparation of Peptide having SEQ ID NO. 54
His Gly Glu Gly Thr Phe Thr Ser Asp Leu Ser Lys Gln Leu Glu Glu Ala Ala Arg Leu Phe Ile Glu Phe Leu Lys Asn-$NH_2$ [SEQ. ID. NO. 54]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 14.0 minutes. Electrospray Mass Spectrometry (M): calculated 3209.6; found 3212.8.

EXAMPLE 53

Preparation of Peptide having SEQ ID NO. 55
His Gly Glu Gly Thr Phe Thr Ser Asp Leu Ser Lys Gln Leu Glu Glu Glu Ala Val Ala Leu Phe Ile Glu Phe Leu Lys Asn-$NH_2$ [SEQ. ID. NO. 55]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 14.3 minutes. Electrospray Mass Spectrometry (M): calculated 3152.5; found 3153.5.

EXAMPLE 54

Preparation of Peptide having SEQ ID NO. 56
His Gly Glu Gly Thr Phe Thr Ser Asp Leu Ser Lys Gln Leu Glu Glu Glu Ala Val Arg Ala Phe Ile Glu Phe Leu Lys Asn-$NH_2$ [SEQ. ID. NO. 56]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 12.1 minutes. Electrospray Mass Spectrometry (M): calculated 3195.5; found 3197.7.

EXAMPLE 55

Preparation of Peptide having SEQ ID NO. 57
His Gly Glu Gly Thr Phe Thr Ser Asp Leu Ser Lys Gln Leu Glu Glu Glu Ala Val Arg Leu Phe Ile Ala Phe Leu Lys Asn-NH$_2$ [SEQ. ID. NO. 57]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 10.9 minutes. Electrospray Mass Spectrometry (M): calculated 3179.6; found 3180.5.

EXAMPLE 56

Preparation of Peptide having SEQ ID NO. 58
His Gly Glu Gly Thr Phe Thr Ser Asp Leu Ser Lys Gln Leu Glu Glu Glu Ala Val Arg Leu Phe Ile Glu Ala Leu Lys Asn-NH$_2$ [SEQ. ID. NO. 58]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 17.5 minutes. Electrospray Mass Spectrometry (M): calculated 3161.5; found 3163.0.

EXAMPLE 57

Preparation of Peptide having SEQ ID NO. 59
His Gly Glu Gly Thr Phe Thr Ser Asp Leu Ser Lys Gln Leu Glu Glu Glu Ala Val Arg Leu Phe Ile Glu Phe Ala Lys Asn-NH$_2$ [SEQ. ID. NO. 59]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 19.5 minutes. Electrospray Mass Spectrometry (M): calculated 3195.5; found 3199.

EXAMPLE 58

Preparation of Peptide having SEQ ID NO. 60
His Gly Glu Gly Thr Phe Thr Ser Asp Leu Ser Lys Gln Leu Glu Glu Glu Ala Val Arg Leu Phe Ile Glu Phe Leu Ala Asn-NH$_2$ [SEQ. ID. NO. 60]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 14.5 minutes. Electrospray Mass Spectrometry (M): calculated 3180.5; found 3183.7.

EXAMPLE 59

Preparation of Peptide having SEQ ID NO. 61
His Gly Glu Gly Thr Phe Thr Ser Asp Leu Ser Lys Gln Leu Glu Glu Glu Ala Val Arg Leu Phe Ile Glu Phe Leu Lys Ala-NH$_2$ [SEQ. ID. NO. 61]

The above-identified amidated peptide was assembled on 4-(2'-4-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis were Solvent A (0.1% TFA in water) and Solvent B (0.1% TFA in ACN). Analytical RP-HPLC (gradient 34% to 44% Solvent B in Solvent A over 30 minutes) of the lyophilized peptide gave product peptide having an observed retention time of 22.8 minutes. Electrospray Mass Spectrometry (M): calculated 3194.6; found 3197.6.

EXAMPLE 60

Preparation of Peptide having SEQ ID NO. 62
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro-NH$_2$ [SEQ. ID. NO. 62]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4099.6.

EXAMPLE 61

Preparation of Peptide having SEQ ID NO. 63
His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro-NH$_2$ [SEQ. ID. NO. 63]

The above-identified amidated peptide is assembled on 4-(2'-4'-dimethoxyphenyl)-Fmoc aminomethyl phenoxy acetamide norleucine MBHA resin (Novabiochem, 0.55

EXAMPLE 62

Preparation of Peptide having SEQ ID NO. 64
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro-NH$_2$ [SEQ. ID. NO. 64]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4002.4

EXAMPLE 63

Preparation of Peptide having SEQ ID NO. 65
His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro-NH$_2$ [SEQ. ID. NO. 65]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3945.4.

EXAMPLE 64

Preparation of Peptide having SEQ ID NO. 66
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro-NH$_2$ [SEQ. ID. NO. 66]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3905.3.

EXAMPLE 65

Preparation of Peptide having SEQ ID NO. 67
His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro-NH$_2$ [SEQ. ID. NO. 67]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3848.2.

EXAMPLE 66

Preparation of Peptide having SEQ ID NO. 68
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ. ID. NO. 68]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3808.2.

EXAMPLE 67

Preparation of Peptide having SEQ ID NO. 69
His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala-NH$_2$ [SEQ. ID. NO. 69]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3751.1.

EXAMPLE 68

Preparation of Peptide having SEQ ID NO. 70
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly-NH$_2$ [SEQ. ID. NO. 70]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and

EXAMPLE 69

Preparation of Peptide having SEQ ID NO. 71

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly-NH$_2$ [SEQ. ID. NO. 71]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3680.1.

EXAMPLE 70

Preparation of Peptide having SEQ ID NO. 72

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser-NH$_2$ [SEQ. ID. NO. 72]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3680.1

EXAMPLE 71

Preparation of Peptide having SEQ ID NO. 73

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser-NH$_2$ [SEQ. ID. NO. 73]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3623.0.

EXAMPLE 72

Preparation of Peptide having SEQ ID NO. 74

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser-NH$_2$ [SEQ. ID. NO. 74]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3593.0

EXAMPLE 73

Preparation of Peptide having SEQ ID NO. 75

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser-NH$_2$ [SEQ. ID. NO. 75]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN) Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3535.9

EXAMPLE 74

Preparation of Peptide having SEQ ID NO. 76

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro-NH$_2$ [SEQ. ID. NO. 76]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3505.9.

EXAMPLE 75

Preparation of Peptide having SEQ ID NO. 77

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro-NH$_2$ [SEQ. ID. NO. 77]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3448.8.

EXAMPLE 76

Preparation of Peptide having SEQ ID NO. 78
His Gly Glu Gly Thr Phe Thr Ser Asp Leu Ser Lys Gln Leu Glu Glu Glu Ala Val Arg Leu Phe Ile Glu Phe Leu Lys Asn Gly Gly-NH$_2$ [SEQ. ID. NO. 78]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3351.7.

EXAMPLE 77

Preparation of Peptide having SEQ ID NO. 79
His Gly Glu Gly Thr Phe Thr Ser Asp Leu Ser Lys Gln Met Glu Glu Glu Ala Val Arg Leu Phe Ile Glu Trp Leu Lys Asn Gly-NH$_2$ [SEQ. ID. NO. 79]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3351.8.

EXAMPLE 78

Preparation of Peptide having SEQ ID NO. 80
His Gly Glu Gly Thr Phe Thr Ser Asp Leu Ser Lys Gln Leu Glu Glu Glu Ala Val Arg Leu Phe Ile Glu Phe Leu Lys Asn Gly-NH$_2$ [SEQ. ID. NO. 80]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3294.7.

EXAMPLE 79

Preparation of Peptide having SEQ ID NO. 81
His Gly Glu Gly Thr Phe Thr Ser Asp Leu Ser Lys Gln Met Glu Glu Glu Ala Val Arg Leu Phe Ile Glu Trp Leu Lys Asn Gly Gly tPro Ser Ser Gly Ala tPro tPro tPro-NH$_2$ [SEQ. ID. NO. 81]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Double couplings are required at residues 37,36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4197.1.

EXAMPLE 80

Preparation of Peptide having SEQ ID NO. 82
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala tPro tPro tPro-NH$_2$ [SEQ. ID. NO. 82]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4179.1.

EXAMPLE 81

Preparation of Peptide having SEQ ID NO. 83
His Gly Glu Gly Thr Phe Thr Ser Asp Leu Ser Lys Gln Met Glu Glu Glu Ala Val Arg Leu Phe Ile Glu Trp Leu Lys Asn Gly Gly NMeala Ser Ser Gly Ala Pro Pro-NH$_2$ [SEQ. ID. NO. 83]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3948.3.

EXAMPLE 82

Preparation of Peptide having SEQ ID NO. 84
His Gly Glu Gly Thr Phe Thr Ser Asp Leu Ser Lys Gln Met Glu Glu Glu Ala Val Arg Leu Phe Ile Glu Trp Leu Lys Asn Gly Gly NMeala Ser Ser Gly Ala NMeala Nmeala-NH$_2$ [SEQ. ID. NO. 84]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3840.1.

EXAMPLE 83

Preparation of Peptide having SEQ ID NO. 85
His Gly Glu Gly Thr Phe Thr Ser Asp Leu Ser Lys Gln Met Glu Glu Glu Ala Val Arg Leu Phe Ile Glu Trp Leu Lys Asn Gly Gly hPro Ser Ser Gly Ala hPro hPro-NH$_2$[SEQ. ID. NO. 85]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4050.1.

EXAMPLE 84

Preparation of Peptide having SEQ ID NO. 86
His Gly Glu Gly Thr Phe Thr Ser Asp Leu Ser Lys Gln Met Glu Glu Glu Ala Val Arg Leu Phe Ile Glu Trp Leu Lys Asn Gly Gly hPro Ser Ser Gly Ala hPro-NH$_2$ [SEQ. ID. NO. 86]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. A double coupling is required at residue 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3937.1

EXAMPLE 85

Preparation of Peptide having SEQ ID NO. 87
Arg Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ. ID. NO. 87]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3827.2.

EXAMPLE 86

Preparation of Peptide having SEQ ID NO. 88
His Gly Asp Gly Thr Phe Thr Ser Asp Leu Ser Lys Gln Met Glu Glu Glu Ala Val Arg Leu Phe Ile Glu Trp Leu Lys Asn Gly Gly-NH$_2$ [SEQ. ID. NO. 88]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3394.8.

EXAMPLE 87

Preparation of Peptide having SEQ ID NO. 89
His Gly Glu Gly Thr Naphthylala Thr Ser Asp Leu Ser Lys Gln Leu Glu Glu Glu Ala Val Arg Leu Phe Ile Glu Phe Leu Lys Asn-NH$_2$ [SEQ. ID. NO. 89]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3289.5.

EXAMPLE 88

Preparation of Peptide having SEQ ID NO. 90
His Gly Glu Gly Thr Phe Ser Ser Asp Leu Ser Lys Gln Met Glu Glu Glu Ala Val Arg Leu Phe Ile Glu Trp Leu Lys Asn-NH$_2$ [SEQ. ID. NO. 90]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3280.7.

EXAMPLE 89

Preparation of Peptide having SEQ ID NO. 91
His Gly Glu Gly Thr Phe Ser Thr Asp Leu Ser Lys Gln Met Glu Glu Glu Ala Val Arg Leu Phe Ile Glu Trp Leu Lys Asn-NH$_2$ [SEQ. ID. NO. 91]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and

41 purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3294.7.

EXAMPLE 90

Preparation of Peptide having SEQ ID NO. 92
His Gly Glu Gly Thr Phe Thr Ser Glu Leu Ser Lys Gln Met Ala Glu Glu Ala Val Arg Leu Phe Ile Glu Trp Leu Lys Asn-NH$_2$ [SEQ. ID. NO. 92]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3250.7.

EXAMPLE 91

Preparation of Peptide having SEQ ID NO. 93
His Gly Glu Gly Thr Phe Thr Ser Asp pentylgly Ser Lys Gln Leu Glu Glu Glu Ala Val Arg Leu Phe Ile Glu Phe Leu Lys Asn-NH$_2$ [SEQ. ID. NO. 93]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3253.5.

EXAMPLE 92

Preparation of Peptide having SEQ ID NO. 94
His Gly Glu Gly Thr Phe Thr Ser Asp Leu Ser Lys Gln Leu Glu Glu Glu Ala Val Arg Leu Naphthylala Ile Glu Phe Leu Lys Asn-NH$_2$ [SEQ. ID. NO. 94]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3289.5.

EXAMPLE 93

Preparation of Peptide having SEQ ID NO. 95
His Gly Glu Gly Thr Phe Thr Ser Asp Leu Ser Lys Gln Met Glu Glu Glu Ala Val Arg Leu Phe tButylgly Glu Trp Leu Lys Asn-NH$_2$ [SEQ. ID. NO. 95]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3183.4.

EXAMPLE 94

Preparation of Peptide having SEQ ID NO. 96
His Gly Glu Gly Thr Phe Thr Ser Asp Leu Ser Lys Gln Leu Glu Glu Glu Ala Val Arg Leu Phe Ile Asp Phe Leu Lys Asn-NH$_2$ [SEQ. ID. NO. 96]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3237.6.

EXAMPLE 95

Preparation of Peptide having SEQ ID NO. 97
His Gly Glu Gly Thr Phe Thr Ser Asp Ala Ser Lys Gln Leu Glu Glu Glu Ala Val Arg Leu Phe Ile Glu Phe Leu Lys Asn Gly Gly Pro Ser Ser-NH$_2$ [SEQ. ID. NO. 97]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3637.9.

EXAMPLE 96

Preparation of Peptide having SEQ ID NO. 98
His Gly Glu Gly Thr Phe Thr Ser Asp Ala Ser Lys Gln Met Glu Glu Glu Ala Val Arg Leu Phe Ile Glu Trp Leu Lys Asn Gly-NH$_2$ [SEQ. ID. NO. 98]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3309.7.

EXAMPLE 97

Preparation of Peptide having SEQ ID NO. 99
His Gly Glu Gly Thr Phe Thr Ser Asp Ala Ser Lys Gln Met Glu Glu Glu Ala Val Arg Leu Phe Ile Glu Trp Leu Lys Asn Gly Gly hPro Ser Ser Gly Ala hPro hPro-NH$_2$ [SEQ. ID. NO. 99]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 37. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3711.1.

EXAMPLE 98

Preparation of C-terminal Carboxylic Acid Peptides Corresponding to the above C-terminal Amide Sequences for SEQ ID NOS. 7, 40–61, 68–75, 78–80 and 87–96

Peptides having the sequences of SEQ ID NOS. 7, 40–61, 68–75, 78–80 and 87–96 are assembled on the so called Wang resin (p-alkoxybenzylalacohol resin (Bachem, 0.54 mmole/g)) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLE 99

Preparation of C-terminal Carboxylic Acid Peptides Corresponding to the above C-terminal Amide Sequences for SEQ ID NOS. 62–67, 76, 77 and 81–86

Peptides having the sequences of SEQ ID NOS. 62–67, 76, 77 and 81–86 are assembled on the 2-chlorotritylchloride resin (200–400 mesh), 2% DVB (Novabiochem, 0.4–1.0 mmole/g)) using Fmoc-protected amino acids (Applied Biosystems, Inc.), cleaved from the resin, deprotected and purified in a similar way to Example 37. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLE 100

Preparation of Peptide having SEQ ID NO. 100
Ala Gly Glu Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 100]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal)of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 60% Solvent B in Solvent A over 30 minutes) of the lyophilized peptide gave product peptide having an observed retention time of 19.2 minutes. Electrospray Mass Spectrometry (M): calculated 3171.6; found 3172.

EXAMPLE 101

Preparation of Peptide having SEQ ID NO. 101
His Gly Ala Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 101]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 14.9 minutes. Electrospray Mass Spectrometry (M): calculated 3179.6; found 3180.

EXAMPLE 102

Preparation of Peptide having SEQ ID NO. 102
His Gly Glu Ala Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 102]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 12.2 minutes. Electrospray Mass Spectrometry (M): calculated 3251.6; found 3253.3.

EXAMPLE 103

Preparation of Peptide having SEQ ID NO. 103
His Gly Glu Gly Thr Phe Thr Ser Ala Leu Ser Lys Gln Leu Glu Glu Glu Ala Val Arg Leu Phe Ile Glu Phe Leu Lys Asn-NH$_2$ [SEQ. ID. NO. 103]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 16.3 minutes. Electrospray Mass Spectrometry (M): calculated 3193.6; found 3197.

EXAMPLE 104

Preparation of Peptide having SEQ ID NO. 104
Ala Gly Glu Gly Thr Phe Thr Ser Asp Leu Ser Lys Gln Met Glu Glu Glu Ala Val Arg Leu Phe Ile Glu Trp Leu Lys Asn-NH$_2$ [SEQ. ID. NO. 104]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3228.6.

EXAMPLE 105

Preparation of Peptide having SEQ ID NO. 105
His Gly Ala Gly Thr Phe Thr Ser Asp Leu Ser Lys Gln Met Glu Glu Glu Ala Val Arg Leu Phe Ile Glu Trp Leu Lys Asn-NH$_2$ [SEQ. ID. NO. 105]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3234.7.

EXAMPLE 106

Preparation of Peptide having SEQ ID NO. 106
His Gly Glu Ala Thr Phe Thr Ser Asp Leu Ser Lys Gln Met Glu Glu Glu Ala Val Arg Leu Phe Ile Glu Trp Leu Lys Asn-NH$_2$ [SEQ. ID. NO. 106]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3308.7.

EXAMPLE 107

Preparation of Peptide having SEQ ID NO. 107
His Gly Glu Gly Thr Phe Thr Ser Ala Leu Ser Lys Gln Met Glu Glu Glu Ala Val Arg Leu Phe Ile Glu Trp Leu Lys Asn-NH$_2$ [SEQ. ID. NO. 107]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3250.7

EXAMPLE 108

Preparation of Peptide having SEQ ID NO. 108
His Gly Glu Gly Thr Phe Thr Ser Asp Ala Ser Lys Gln Met Glu Glu Glu Ala Val Arg Leu Phe Ile Glu Trp Leu Lys Asn-NH$_2$ [SEQ. ID. NO. 108]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3252.6.

EXAMPLE 109

Preparation of Peptide having SEQ ID NO. 109
Ala Ala Glu Gly Thr Phe Thr Ser Asp Leu Ser Lys Gln Met Glu Glu Glu Ala Val Arg Leu Phe Ile Glu Trp Leu Lys Asn-NH$_2$ [SEQ. ID. NO. 109]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 110

Preparation of Peptide having SEQ ID NO. 110
Ala Ala Glu Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 110]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 111

Preparation of Peptide having SEQ ID NO. 111
Ala Gly Asp Gly Thr Phe Thr Ser Asp Leu Ser Lys Gln Met Glu Glu Glu Ala Val Arg Leu Phe Ile Glu Trp Leu Lys Asn-NH$_2$ [SEQ. ID. NO. 111]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3214.6.

EXAMPLE 112

Preparation of Peptide having SEQ ID NO. 112
Ala Gly Asp Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 112]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.5.

EXAMPLE 113

Preparation of Peptide having SEQ ID NO. 113
Ala Gly Asp Gly Ala Phe Thr Ser Asp Leu Ser Lys Gln Met Glu Glu Glu Ala Val Arg Leu Phe Ile Glu Trp Leu Lys Asn-NH$_2$ [SEQ. ID. NO. 113]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3184.6.

EXAMPLE 114

Preparation of Peptide having SEQ ID NO. 114
Ala Gly Asp Gly Ala Phe Thr Ser Asp Leu Ser Lys Gln Leu Glu Glu Glu Ala Val Arg Leu Phe Ile Glu Phe Leu Lys Asn-NH$_2$ [SEQ. ID. NO. 114]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3127.5.

EXAMPLE 115

Preparation of Peptide having SEQ ID NO. 115
Ala Gly Asp Gly Thr NaphthylAla Thr Ser Asp Leu Ser Lys Gln Met Glu Glu Glu Ala Val Arg Leu Phe Ile Glu Trp Leu Lys Asn-NH$_2$ [SEQ. ID. NO. 115]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3266.4.

EXAMPLE 116

Preparation of Peptide having SEQ ID NO. 116
Ala Gly Asp Gly Thr Naphthylala Thr Ser Asp Leu Ser Lys Gln Leu Glu Glu Glu Ala Val Arg Leu Phe Ile Glu Phe Leu Lys Asn-NH$_2$ [SEQ. ID. NO. 116]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3209.4.

EXAMPLE 117

Preparation of Peptide having SEQ ID NO. 117
Ala Gly Asp Gly Thr Phe Ser Ser Asp Leu Ser Lys Gln Met Glu Glu Glu Ala Val Arg Leu Phe Ile Glu Trp Leu Lys Asn-NH$_2$ [SEQ. ID. NO. 117]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 118

Preparation of Peptide having SEQ ID NO. 118
Ala Gly Asp Gly Thr Phe Ser Ser Asp Leu Ser Lys Gln Leu Glu Glu Glu Ala Val Arg Leu Phe Ile Glu Phe Leu Lys Asn-$NH_2$ [SEQ. ID. NO. 118]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 119

Preparation of Peptide having SEQ ID NO. 119
Ala Gly Asp Gly Thr Phe Thr Ala Asp Leu Ser Lys Gln Met Glu Glu Glu Ala Val Arg Leu Phe Ile Glu Trp Leu Lys Asn-$NH_2$ [SEQ. ID. NO. 119]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3198.6.

EXAMPLE 120

Preparation of Peptide having SEQ ID NO. 120
Ala Gly Asp Gly Thr Phe Thr Ala Asp Leu Ser Lys Gln Leu Glu Glu Glu Ala Val Arg Leu Phe Ile Glu Phe Leu Lys Asn-$NH_2$ [SEQ. ID. NO. 120]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3141.5.

EXAMPLE 121

Preparation of Peptide having SEQ ID NO. 121
Ala Gly Asp Gly Thr Phe Thr Ser Ala Leu Ser Lys Gln Met Glu Glu Glu Ala Val Arg Leu Phe Ile Glu Trp Leu Lys Asn-$NH_2$ [SEQ. ID. NO. 121]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3170.6.

EXAMPLE 122

Preparation of Peptide having SEQ ID NO. 122
Ala Gly Asp Gly Thr Phe Thr Ser Ala Leu Ser Lys Gln Leu Glu Glu Glu Ala Val Arg Leu Phe Ile Glu Phe Leu Lys Asn-$NH_2$ [SEQ. ID. NO. 122]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3113.5.

EXAMPLE 123

Preparation of Peptide having SEQ ID NO. 123
Ala Gly Asp Gly Thr Phe Thr Ser Glu Leu Ser Lys Gln Met Glu Glu Glu Ala Val Arg Leu Phe Ile Glu Trp Leu Lys Asn-$NH_2$ [SEQ. ID. NO. 123]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3228.6.

EXAMPLE 124

Preparation of Peptide having SEQ ID NO. 124
Ala Gly Asp Gly Thr Phe Thr Ser Glu Leu Ser Lys Gln Leu Glu Glu Glu Ala Val Arg Leu Phe Ile Glu Phe Leu Lys Asn-$NH_2$ [SEQ. ID. NO. 124]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3171.6.

EXAMPLE 125

Preparation of Peptide having SEQ ID NO. 125
Ala Gly Asp Gly Thr Phe Thr Ser Asp Ala Ser Lys Gln Met Glu Glu Glu Ala Val Arg Leu Phe Ile Glu Trp Leu Lys Asn-$NH_2$ [SEQ. ID. NO. 125]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3172.5.

EXAMPLE 126

Preparation of Peptide having SEQ ID NO. 126
Ala Gly Asp Gly Thr Phe Thr Ser Asp Ala Ser Lys Gln Leu Glu Glu Glu Ala Val Arg Leu Phe Ile Glu Phe Leu Lys Asn-NH$_2$ [SEQ. ID. NO. 126]
The above-identified amidated peptiden is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.4.

EXAMPLE 127

Preparation of Peptide having SEQ ID NO. 127
Ala Gly Asp Gly Thr Phe Thr Ser Asp Pentylgly Ser Lys Gln Met Glu Glu Glu Ala Val Arg Leu Phe Ile Glu Trp Leu Lys Asn-NH$_2$ [SEQ. ID. NO. 127]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3230.4.

EXAMPLE 128

Preparation of Peptide having SEQ ID NO. 128
Ala Gly Asp Gly Thr Phe Thr Ser Asp Pentylgly Ser Lys Gln Leu Glu Glu Glu Ala Val Arg Leu Phe Ile Glu Phe Leu Lys Asn-NH$_2$ [SEQ. ID. NO. 128]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3198.6.

EXAMPLE 129

Preparation of Peptide having SEQ ID NO. 129
Ala Gly Asp Gly Thr Phe Thr Ser Asp Leu Ala Lys Gln Met Glu Glu Glu Ala Val Arg Leu Phe Ile Glu Trp Leu Lys Asn-NH$_2$ [SEQ. ID. NO. 129]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3141.5.

EXAMPLE 130

Preparation of Peptide having SEQ ID NO. 130
Ala Gly Asp Gly Thr Phe Thr Ser Asp Leu Ala Lys Gln Leu Glu Glu Glu Ala Val Arg Leu Phe Ile Glu Phe Leu Lys Asn-NH$_2$ [SEQ. ID. NO. 130]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.5.

EXAMPLE 131

Preparation of Peptide having SEQ ID NO. 131
Ala Gly Asp Gly Thr Phe Thr Ser Asp Leu Ser Ala Gln Met Glu Glu Glu Ala Val Arg Leu Phe Ile Glu Trp Leu Lys Asn-NH$_2$ [SEQ. ID. NO. 131]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.4.

EXAMPLE 132

Preparation of Peptide having SEQ ID NO. 132
Ala Gly Asp Gly Thr Phe Thr Ser Asp Leu Ser Ala Gln Leu Glu Glu Glu Ala Val Arg Leu Phe Ile Glu Phe Leu Lys Asn-NH$_2$ [SEQ. ID. NO. 132]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.6.

EXAMPLE 133

Preparation of Peptide having SEQ ID NO. 133
Ala Gly Asp Gly Thr Phe Thr Ser Asp Leu Ser Lys Ala Met Glu Glu Glu Ala Val Arg Leu Phe Ile Glu Trp Leu Lys Asn-N$_2$ [SEQ. ID. NO. 133]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.5.

EXAMPLE 134

Preparation of Peptide having SEQ ID NO. 134
Ala Gly Asp Gly Thr Phe Thr Ser Asp Leu Ser Lys Ala Leu Glu Glu Glu Ala Val Arg Leu Phe Ile Glu Phe Leu Lys Asn-NH$_2$ [SEQ. ID. NO. 134]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.5.

EXAMPLE 135

Preparation of Peptide having SEQ ID NO. 135
Ala Gly Asp Gly Thr Phe Thr Ser Asp Leu Ser Lys Gln Ala Glu Glu Glu Ala Val Arg Leu Phe Ile Glu Trp Leu Lys Asn-NH$_2$ [SEQ. ID. NO. 135]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3154.5.

EXAMPLE 136

Preparation of Peptide having SEQ ID NO. 136
Ala Gly Asp Gly Thr Phe Thr Ser Asp Leu Ser Lys Gln Ala Glu Glu Glu Ala Val Arg Leu Phe Ile Glu Phe Leu Lys Asn-NH$_2$ [SEQ. ID. NO. 136]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.5.

EXAMPLE 137

Preparation of Peptide having SEQ ID NO. 137
Ala Gly Asp Gly Thr Phe Thr Ser Asp Leu Ser Lys Gln Pentylgly Glu Glu Glu Ala Val Arg Leu Phe Ile Glu Trp Leu Lys Asn-NH$_2$ [SEQ. ID. NO. 137]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent 5 A (0.1% TFA in water) and Solvent B (0.1% TFA in ACN).

Analytical RP-HPLC (gradient 30% to 60% Solvent B in Solvent A over 30 minutes) of the lyophilized peptide is then carried out to determine the retention time of the product peptide. Electrospray Mass Spectrometry (M): 10 calculated 3212.4.

EXAMPLE 138

Preparation of Peptide having SEQ ID NO. 138
Ala Gly Asp Gly Thr Phe Thr Ser Asp Leu Ser Lys Gln Pentylgly Glu Glu Glu Ala Val Arg Leu Phe Ile Glu Phe Leu Lys Asn-NH$_2$ [SEQ. ID. NO. 138]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3173.4.

EXAMPLE 139

Preparation of Peptide having SEQ ID NO. 139
Ala Gly Asp Gly Thr Phe Thr Ser Asp Leu Ser Lys Gln Met Ala Glu Glu Ala Val Arg Leu Phe Ile Glu Trp Leu Lys Asn-NH$_2$ [SEQ. ID. NO. 139]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3156.6.

EXAMPLE 140

Preparation of Peptide having SEQ ID NO. 140
Ala Gly Asp Gly Thr Phe Thr Ser Asp Leu Ser Lys Gln Leu Ala Glu Glu Ala Val Arg Leu Phe Ile Glu Phe Leu Lys Asn-NH$_2$ [SEQ. ID. NO. 140]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 141

Preparation of Peptide having SEQ ID NO. 141
Ala Gly Asp Gly Thr Phe Thr Ser Asp Leu Ser Lys Gln Met Glu Ala Glu Ala Val Arg Leu Phe Ile Glu Trp Leu Lys Asn-NH$_2$ [SEQ. ID. NO. 141]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3156.6.

EXAMPLE 142

Preparation of Peptide having SEQ ID NO. 142
Ala Gly Asp Gly Thr Phe Thr Ser Asp Leu Ser Lys Gln Leu Glu Ala Glu Ala Val Arg Leu Phe Ile Glu Phe Leu Lys Asn-NH$_2$ [SEQ. ID. NO. 142]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 143

Preparation of Peptide having SEQ ID NO. 143
Ala Gly Asp Gly Thr Phe Thr Ser Asp Leu Ser Lys Gln Met Glu Glu Ala Ala Val Arg Leu Phe Ile Glu Trp Leu Lys Asn-NH$_2$ [SEQ. ID. NO. 143]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3156.6.

EXAMPLE 144

Preparation of Peptide having SEQ ID NO. 144
Ala Gly Asp Gly Thr Phe Thr Ser Asp Leu Ser Lys Gln Leu Glu Glu Ala Ala Val Arg Leu Phe Ile Glu Phe Leu Lys Asn-NH$_2$ [SEQ. ID. NO. 144]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 145

Preparation of Peptide having SEQ ID NO. 145
Ala Gly Asp Gly Thr Phe Thr Ser Asp Leu Ser Lys Gln Met Glu Glu Glu Ala Ala Arg Leu Phe Ile Glu Trp Leu Lys Asn-NH$_2$ [SEQ. ID. NO. 145]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3186.6.

EXAMPLE 146

Preparation of Peptide having SEQ ID NO. 146
Ala Gly Asp Gly Thr Phe Thr Ser Asp Leu Ser Lys Gln Leu Glu Glu Glu Ala Ala Arg Leu Phe Ile Glu Phe Leu Lys Asn-NH$_2$ [SEQ. ID. NO. 146]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3129.5.

EXAMPLE 147

Preparation of Peptide having SEQ ID NO. 147
Ala Gly Asp Gly Thr Phe Thr Ser Asp Leu Ser Lys Gln Met Glu Glu Glu Ala Val Ala Leu Phe Ile Glu Trp Leu Lys Asn-NH$_2$ [SEQ. ID. NO. 147]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3129.5.

EXAMPLE 148

Preparation of Peptide having SEQ ID NO. 148
Ala Gly Asp Gly Thr Phe Thr Ser Asp Leu Ser Lys Gln Leu Glu Glu Glu Ala Val Ala Leu Phe Ile Glu Phe Leu Lys Asn-NH$_2$ [SEQ. ID. NO. 148]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3072.4.

EXAMPLE 149

Preparation of Peptide having SEQ ID NO. 149
Ala Gly Asp Gly Thr Phe Thr Ser Asp Leu Ser Lys Gln Met Glu Glu Glu Ala Val Arg Ala Phe Ile Glu Trp Leu Lys Asn-NH$_2$ [SEQ. ID. NO. 149]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3172.5.

EXAMPLE 150

Preparation of Peptide having SEQ ID NO. 150
Ala Gly Asp Gly Thr Phe Thr Ser Asp Leu Ser Lys Gln Leu Glu Glu Glu Ala Val Arg Ala Phe Ile Glu Phe Leu Lys Asn-NH$_2$ [SEQ. ID. NO. 150]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.5.

EXAMPLE 151

Preparation of Peptide having SEQ ID NO. 151
Ala Gly Asp Gly Thr Phe Thr Ser Asp Leu Ser Lys Gln Met Glu Glu Glu Ala Val Arg Leu Naphthylala Ile Glu Trp Leu Lys Asn-NH$_2$ [SEQ. ID. NO. 151]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3266.4.

EXAMPLE 152

Preparation of Peptide having SEQ ID NO. 152
Ala Gly Asp Gly Thr Phe Thr Ser Asp Leu Ser Lys Gln Leu Glu Glu Glu Ala Val Arg Leu Naphthylala Ile Glu Phe Leu Lys Asn-NH$_2$ [SEQ. ID. NO. 152]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3209.4.

EXAMPLE 153

Preparation of Peptide having SEQ ID NO. 153
Ala Gly Asp Gly Thr Phe Thr Ser Asp Leu Ser Lys Gln Met Glu Glu Glu Ala Val Arg Leu Phe Val Glu Trp Leu Lys Asn-NH$_2$ [SEQ. ID. NO. 153]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 154

Preparation of Peptide having SEQ ID NO. 154
Ala Gly Asp Gly Thr Phe Thr Ser Asp Leu Ser Lys Gln Leu Glu Glu Glu Ala Val Arg Leu Phe Val Glu Phe Leu Lys Asn-NH$_2$ [SEQ. ID. NO. 154]
The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and

EXAMPLE 155

Preparation of Peptide having SEQ ID NO. 155
Ala Gly Asp Gly Thr Phe Thr Ser Asp Leu Ser Lys Gln Met Glu Glu Glu Ala Val Arg Leu Phe tButylgly Glu Trp Leu Lys Asn-NH$_2$ [SEQ. ID. NO. 155]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3216.5.

EXAMPLE 156

Preparation of Peptide having SEQ ID NO. 156
Ala Gly Asp Gly Thr Phe Thr Ser Asp Leu Ser Lys Gln Leu Glu Glu Glu Ala Val Arg Leu Phe tButylgly Glu Phe Leu Lys Asn-NH$_2$ [SEQ. ID. NO. 156]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3159.4.

EXAMPLE 157

Preparation of Peptide having SEQ ID NO. 157
Ala Gly Asp Gly Thr Phe Thr Ser Asp Leu Ser Lys Gln Met Glu Glu Glu Ala Val Arg Leu Phe Ile Asp Trp Leu Lys Asn-NH$_2$ [SEQ. ID. NO. 157]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 158

Preparation of Peptide having SEQ ID NO. 158
Ala Gly Asp Gly Thr Phe Thr Ser Asp Leu Ser Lys Gln Leu Glu Glu Glu Ala Val Arg Leu Phe Ile Asp Phe Leu Lys Asn-NH$_2$ [SEQ. ID. NO. 158]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 159

Preparation of Peptide having SEQ ID NO. 159
Ala Gly Asp Gly Thr Phe Thr Ser Asp Leu Ser Lys Gln Met Glu Glu Glu Ala Val Arg Leu Phe Ile Glu Ala Leu Lys Asn-NH$_2$ [SEQ. ID. NO. 159]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 160

Preparation of Peptide having SEQ ID NO. 160
Ala Gly Asp Gly Thr Phe Thr Ser Asp Leu Ser Lys Gln Leu Glu Glu Glu Ala Val Arg Leu Phe Ile Glu Ala Leu Lys Asn-NH$_2$ [SEQ. ID. NO. 160]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3081.4.

EXAMPLE 161

Preparation of Peptide having SEQ ID NO. 161
Ala Gly Asp Gly Thr Phe Thr Ser Asp Leu Ser Lys Gln Met Glu Glu Glu Ala Val Arg Leu Phe Ile Glu Trp Ala Lys Asn-NH$_2$ [SEQ. ID. NO. 161]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3172.5.

EXAMPLE 162

Preparation of Peptide having SEQ ID NO. 162
Ala Gly Asp Gly Thr Phe Thr Ser Asp Leu Ser Lys Gln Leu Glu Glu Glu Ala Val Arg Leu Phe Ile Glu Phe Ala Lys Asn-NH$_2$ [SEQ. ID. NO. 162]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.5.

EXAMPLE 163

Preparation of Peptide having SEQ ID NO. 163
Ala Gly Asp Gly Thr Phe Thr Ser Asp Leu Ser Lys Gln Met Glu Glu Glu Ala Val Arg Leu Phe Ile Glu Trp Leu Ala Asn-NH$_2$ [SEQ. ID. NO. 163]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.5.

EXAMPLE 164

Preparation of Peptide having SEQ ID NO. 164
Ala Gly Asp Gly Thr Phe Thr Ser Asp Leu Ser Lys Gln Leu Glu Glu Glu Ala Val Arg Leu Phe Ile Glu Phe Leu Ala Asn-NH$_2$ [SEQ. ID. NO. 164]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.4.

EXAMPLE 165

Preparation of Peptide having SEQ ID NO. 165
Ala Gly Asp Gly Thr Phe Thr Ser Asp Leu Ser Lys Gln Met Glu Glu Glu Ala Val Arg Leu Phe Ile Glu Trp Leu Lys Ala-NH$_2$ [SEQ. ID. NO. 165]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3171.6.

EXAMPLE 166

Preparation of Peptide having SEQ ID NO. 166
Ala Gly Asp Gly Thr Phe Thr Ser Asp Leu Ser Lys Gln Leu Glu Glu Glu Ala Val Arg Leu Phe Ile Glu Phe Leu Lys Ala-NH$_2$ [SEQ. ID. NO. 166]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3114.5.

EXAMPLE 167

Preparation of Peptide having SEQ ID NO. 167
Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro-NH$_2$ [SEQ. ID. NO. 167]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4033.5.

EXAMPLE 168

Preparation of Peptide having SEQ ID NO. 168
His Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro-NH$_2$ [SEQ. ID. NO. 168]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3984.4.

EXAMPLE 169

Preparation of Peptide having SEQ ID NO. 169
His Gly Glu Ala Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro-NH$_2$ [SEQ. ID. NO. 169]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4016.5.

EXAMPLE 170

Preparation of Peptide having SEQ ID NO. 170
His Gly Glu Gly Thr Phe Thr Ser Ala Leu Ser Lys Gln Met Glu Glu Glu Ala Val Arg Leu Phe Ile Glu Trp Leu Lys Asn Gly Gly Pro Ser Ser Gly Ala Pro-NH$_2$ [SEQ. ID. NO. 170]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3861.3.

EXAMPLE 171

Preparation of Peptide having SEQ ID NO. 171
Ala Gly Glu Gly Thr Phe Thr Ser Asp Ala Ser Lys Gln Leu Glu Glu Glu Ala Val Arg Leu Phe Ile Glu Phe Leu Lys Asn Gly Gly Pro Ser Ser Gly Ala Pro-NH$_2$ [SEQ. ID. NO. 171]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3746.1.

EXAMPLE 172

Preparation of Peptide having SEQ ID NO. 172
Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ. ID. NO. 172]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3742.1.

EXAMPLE 173

Preparation of Peptide having SEQ ID NO. 173
His Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala-NH$_2$ [SEQ. ID. NO. 173]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3693.1.

EXAMPLE 174

Preparation of Peptide having SEQ ID NO. 174
His Gly Glu Ala Thr Phe Thr Ser Asp Leu Ser Lys Gln Met Glu Glu Glu Ala Val Arg Leu Phe Ile Glu Trp Leu Lys Asn Gly Gly Pro Ser Ser Gly-NH$_2$ [SEQ. ID. NO. 174]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3751.2.

EXAMPLE 175

Preparation of Peptide having SEQ ID NO. 175
His Gly Glu Gly Thr Phe Thr Ser Ala Leu Ser Lys Gln Met Glu Glu Glu Ala Val Arg Leu Phe Ile Glu Trp Leu Lys Asn Gly Gly Pro Ser Ser-NH$_2$ [SEQ. ID. NO. 175]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3634.1.

EXAMPLE 176

Preparation of Peptide having SEQ ID NO. 176
Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser-NH$_2$ [SEQ. ID. NO. 176]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3526.9.

EXAMPLE 177

Preparation of Peptide having SEQ ID NO. 177
His Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser-NH$_2$ [SEQ. ID. NO. 177]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3477.9.

EXAMPLE 178

Preparation of Peptide having SEQ ID NO. 178
His Gly Glu Ala Thr Phe Thr Ser Asp Leu Ser Lys Gln Met Glu Glu Glu Ala Val Arg Leu Phe Ile Glu Trp Leu Lys Asn Gly Gly Pro-NH$_2$ [SEQ. ID. NO. 178]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3519.9.

EXAMPLE 179

Preparation of Peptide having SEQ ID NO. 179
His Gly Glu Gly Thr Phe Thr Ser Ala Leu Ser Lys Gln Leu Glu Glu Glu Ala Val Arg Leu Phe Ile Glu Phe Leu Lys Asn Gly Gly-NH$_2$ [SEQ. ID. NO. 179]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3307.7.

EXAMPLE 180

Preparation of Peptide having SEQ ID NO. 180
Ala Gly Glu Gly Thr Phe Thr Ser Asp Leu Ser Lys Gln Leu Glu Glu Glu Ala Val Arg Leu Phe Ile Glu Phe Leu Lys Asn Gly-NH$_2$ [SEQ. ID. NO. 180]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3186.5.

EXAMPLE 181

Preparation of Peptide having SEQ ID NO. 181
His Gly Ala Gly Thr Phe Thr Ser Asp Leu Ser Lys Gln Met Glu Glu Glu Ala Val Arg Leu Phe Ile Glu Trp Leu Lys Asn Gly Gly tPro Ser Ser Gly Ala tPro tPro tPro-NH$_2$ [SEQ. ID. NO. 181]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Double couplings are required at residues 37,36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4121.1.

EXAMPLE 182

Preparation of Peptide having SEQ ID NO. 182
His Gly Glu Ala Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala tPro tPro tPro-NH$_2$ [SEQ. ID. NO. 182].

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4173.2.

EXAMPLE 183

Preparation of Peptide having SEQ ID NO. 183
His Gly Glu Gly Thr Phe Thr Ser Ala Leu Ser Lys Gln Met Glu Glu Glu Ala Val Arg Leu Phe Ile Glu Trp Leu Lys Asn Gly Gly NMeala Ser Ser Gly Ala NMeala NMeala-NH$_2$ [SEQ. ID. NO. 183]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3796.1.

EXAMPLE 184

Preparation of Peptide having SEQ ID NO. 184
Ala Gly Glu Gly Thr Phe Thr Ser Asp Leu Ser Lys Gln Met Glu Glu Glu Ala Val Arg Leu Phe Ile Glu Trp Leu Lys Asn Gly Gly hPro Ser Ser Gly Ala hPro-NH$_2$ [SEQ. ID. NO. 184]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. A double coupling is required at residue 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3871.1.

EXAMPLE 185

Preparation of Peptide having SEQ ID NO. 185
His Gly Ala Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ. ID. NO. 185]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3750.2.

EXAMPLE 186

Preparation of Peptide having SEQ ID NO. 186
His Gly Asp Ala Thr Phe Thr Ser Asp Leu Ser Lys Gln Met Glu Glu Glu Ala Val Arg Leu Phe Ile Glu Trp Leu Lys Asn Gly Gly-NH$_2$ [SEQ. ID. NO. 186]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3408.8.

EXAMPLE 187

Preparation of Peptide having SEQ ID NO. 187
Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$ [SEQ. ID. NO. 187]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4120.6.

EXAMPLE 188

Preparation of Peptide having SEQ ID NO. 188
Ala Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-NH$_2$ [SEQ. ID. NO. 188]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4005.5.

EXAMPLE 189

Preparation of C-Terminal Carboxylic Acid Peptides Corresponding to the Above C-Terminal Amide Sequences for Peptides having SEQ ID NOS. 100–166, 172–177, 179–180 and 185–188

C-terminal carboxylic acid peptides corresponding to amidated having SEQ ID NOS. 100–166, 172–177, 179–180 and 185–188 are assembled on the so called Wang resin (p-alkoxybenzylalacohol resin (Bachem, 0.54 mmole/g))

using Fmoc-protected amino acids (Applied Biosystems, Inc.), cleaved from the resin, deprotected and purified in a similar way to that described in Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLE 190

Preparation of C-Terminal Carboxylic Acid Peptides Corresponding to the Above C-Terminal Amide Sequences for Peptides having SEQ ID NOS. 167–171, 178 and 181–184

C-terminal carboxylic acid eptides corresponding to amidated SEQ ID NOS. 167–171, 178 and 181–184 are assembled on the 2-chlorotritylchloride resin (200–400 mesh), 2% DVB (Novabiochem, 0.4–1.0 mmole/g)) using Fmoc-protected amino acids (Applied Biosystems, Inc.), cleaved from the resin, deprotected and purified in a similar way to that described in Example 100. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

Various modifications of the invention in addition to those shown and described herein will become apparent to those skilled in the art from the foregoing description and fall within the scope of the following claims.

We claim:

1. A method for reducing food intake in a subject desirous or in need of reducing food intake, comprising peripherally administering to said subject an amount of an exendin effective to reduce food intake.

2. The method according to claim 1, wherein said peripheral administration is by injection.

3. The method according to claim 1, wherein said peripheral administration is selected from the group consisting of intravenous administration, intraperitoneal administration, subcutaneous administration, intramuscular administration, oral administration, topical administration, transmucosal administration, and pulmonary administration.

4. The method according to claim 1, wherein about 10 µg/70 kg to about 5 mg/70 kg of the exendin is administered per day in single or divided doses.

5. The method according to claim 1, wherein about 10 µg/70 kg to about 2 mg/70 kg of the exendin is administered per day in single or divided doses.

6. The method according to claim 1, wherein about 10 µg/70 kg to about 500 µg/70 kg of the exendin is administered per day in single or divided doses.

7. The method according to claim 1, wherein about 0.1 µg/kg to about 100 µg/kg of the exendin is administered per day in single or divided doses.

8. The method according to claim 1, wherein about 0.1 µg/kg to about 10 µg/kg of the exendin is administered per day in single or divided doses.

9. The method according to claim 1, wherein about 0.1 µg/kg to about 1 µg/kg of the exendin is administered per day in single or divided doses.

10. The method of claim 1, wherein said subject is human.

11. The method of claim 1, wherein said subject suffers from Type II diabetes.

12. The method of claim 1, wherein said subject suffers from an eating disorder.

13. The method of claim 1, wherein said subject suffers from an insulin-resistance syndrome.

14. The method of claim 1, wherein said exendin is exendin-3.

15. The method of claim 1, wherein said exendin is exendin-4.

16. The method of claim 1, further comprising administering a therapeutically effective amount of one or more compounds selected from the group consisting of an amylin agonist, a leptin, and a cholecystokinin (CCK).

17. A method for reducing appetite in a subject desirous or in need of reducing appetite, comprising peripherally administering to said subject an amount of an exendin effective to reduce appetite.

18. The method according to claim 17, wherein said peripheral administration is by injection.

19. The method according to claim 17, wherein said peripheral administration is selected from the group consisting of intravenous administration, intraperitoneal administration, subcutaneous administration, intramuscular administration, oral administration, topical administration, transmucosal administration, and pulmonary administration.

20. The method according to claim 17, wherein about 10 µg/70 kg to about 5 mg/70 kg of the exendin is administered per day in single or divided doses.

21. The method according to claim 17, wherein about 10 µg/70 kg to about 2 mg/70 kg of the exendin is administered per day in single or divided doses.

22. The method according to claim 17, wherein about 10 µg/70 kg to about 500 µg/70 kg of the exendin is administered per day in single or divided doses.

23. The method according to claim 17, wherein about 0.1 µg/kg to about 100 µg/kg of the exendin is administered per day in single or divided doses.

24. The method according to claim 17, wherein about 0.1 µg/kg to about 10 µg/kg of the exendin is administered per day in single or divided doses.

25. The method according to claim 17, wherein about 0.1 µg/kg to about 1 µg/kg of the exendin is administered per day in single or divided doses.

26. The method of claim 17, wherein said subject is human.

27. The method of claim 17, wherein said subject suffers from Type II diabetes.

28. The method of claim 17, wherein said subject suffers from an eating disorder.

29. The method of claim 17, wherein said subject suffers from an insulin-resistance syndrome.

30. The method of claim 17, wherein said exendin is exendin-3.

31. The method of claim 17, wherein said exendin is exendin-4.

32. The method of claim 17, further comprising administering a therapeutically effective amount of one or more compounds selected from the group consisting of an amylin agonist, a leptin, and a cholecystokinin (CCK).

33. A method for reducing food intake in a subject desirous or in need of reducing food intake comprising peripherally administering to said subject an amount of exendin-4 effective to reduce food intake.

34. The method according to claim 33, wherein said peripheral administration is by injection.

35. The method according to claim 33, wherein said peripheral administration is selected from the group consisting of intravenous administration, intraperitoneal administration, subcutaneous administration, intramuscular administration, oral administration, topical administration, transmucosal administration, and pulmonary administration.

36. The method according to claim 33, wherein about 10 µg/70 kg to about 5 mg/70 kg of the exendin-4 is administered per day in single or divided doses.

37. The method according to claim 33, wherein about 10 µg/70 kg to about 2 mg/70 kg of the exendin-4 is administered per day in single or divided doses.

38. The method according to claim 33, wherein about 10 µg/70 kg to about 500 µg/70 kg of the exendin-4 is administered per day in single or divided doses.

39. The method according to claim 33, wherein about 0.1 µg/kg to about 100 µg/kg of the exendin-4 is administered per day in single or divided doses.

40. The method according to claim 33, wherein about 0.1 µg/kg to about 10 µg/kg of the exendin-4 is administered per day in single or divided doses.

41. The method according to claim 33, wherein about 0.1 µg/kg to about 1 µg/kg of the exendin-4 is administered per day in single or divided doses.

42. The method of claim 33, wherein said subject is human.

43. The method of claim 33, wherein said subject suffers from Type II diabetes.

44. The method of claim 33, wherein said subject suffers from an eating disorder.

45. The method of claim 33, wherein said subject suffers from an insulin-resistance syndrome.

46. The method of claim 33, further comprising administering a therapeutically effective amount of one or more compounds selected from the group consisting of an amylin agonist, a leptin, and a cholecystokinin (CCK).

47. A method for reducing appetite in a subject desirous or in need of reducing appetite, comprising peripherally administering to said subject an amount of exendin-4 effective to reduce appetite.

48. The method according to claim 47, wherein said peripheral administration is by injection.

49. The method according to claim 47, wherein said peripheral administration is selected from the group consisting of intravenous administration, intraperitoneal administration, subcutaneous administration, intramuscular administration, oral administration, topical administration, transmucosal administration, and pulmonary administration.

50. The method according to claim 47, wherein about 10 µg/70 kg to about 5 mg/70 kg of the exendin-4 is administered per day in single or divided doses.

51. The method according to claim 47, wherein about 10 µg/70 kg to about 2 mg/70 kg of the exendin-4 is administered per day in single or divided doses.

52. The method according to claim 47, wherein about 10 µg/70 kg to about 500 µg/70 kg of the exendin-4 is administered per day in single or divided doses.

53. The method according to claim 47, wherein about 0.1 µg/kg to about 100 µg/kg of the exendin-4 is administered per day in single or divided doses.

54. The method according to claim 47, wherein about 0.1 µg/kg to about 10 µg/kg of the exendin-4 is administered per day in single or divided doses.

55. The method according to claim 47, wherein about 0.1 µg/kg to about 1 µg/kg of the exendin-4 is administered per day in single or divided doses.

56. The method of claim 47, wherein said subject is human.

57. The method of claim 47, wherein said subject suffers from Type II diabetes.

58. The method of claim 47, wherein said subject suffers from an eating disorder.

59. The method of claim 47, wherein said subject suffers from an insulin-resistance syndrome.

60. The method of claim 47, further comprising administering a therapeutically effective amount of one or more compounds selected from the group consisting of an amylin agonist, a leptin, and a cholecystokinin (CCK).

61. A method for reducing food intake in a subject desirous or in need of reducing body weight, comprising peripherally administering to said subject an amount of exendin-4 effective to lower a plasma lipid level.

62. The method according to claim 61, wherein said peripheral administration is by injection.

63. The method according to claim 61, wherein said peripheral administration is selected from the group consisting of intravenous administration intraperitoneal administration, subcutaneous administration, intramuscular administration, oral administration, topical administration, transmucosal administration, and pulmonary administration.

64. The method of claim 61, further comprising administering a therapeutically effective amount of one or more compounds selected from the group consisting of an amylin agonist, a leptin, and a cholecystokinin (CCK).

65. A method for reducing appetite in a subject desirous or in need of reducing body weight, comprising peripherally administering to said subject an amount of exendin-4 effective to lower a plasma lipid level.

66. The method according to claim 65, wherein said peripheral administration is by injection.

67. The method according to claim 65, wherein said peripheral administration is selected from the group consisting of intravenous administration, intraperitoneal administration, subcutaneous administration, intramuscular administration, oral administration, topical administration, transmucosal administration, and pulmonary administration.

68. The method of claim 65, further comprising administering a therapeutically effective amount of one or more compounds selected from the group consisting of an amylin agonist, a leptin, and a cholecystokinin (CCK).

* * * * *

UNITED STATES PATENT AND TRADEMARK OFFICE
CERTIFICATE OF CORRECTION

PATENT NO.    : 6,956,026 B2
DATED         : October 18, 2005
INVENTOR(S)   : Young, Andrew A. and Bhavsar, Sunil Page 1 of 1

It is certified that error appears in the above-identified patent and that said Letters Patent is hereby corrected as shown below:

Column 188,
Lines 26-58, delete "61. A method for reducing food intake" ends with "and a cholecystokinin (CCK).".

Signed and Sealed this

Thirty-first Day of January, 2006

JON W. DUDAS
*Director of the United States Patent and Trademark Office*

UNITED STATES PATENT AND TRADEMARK OFFICE
CERTIFICATE OF CORRECTION

PATENT NO.   : 6,956,026 B2
DATED        : October 18, 2005
INVENTOR(S)  : Young, Andrew A. and Bhavsar, Sunil It is certified that error appears in the above-identified patent and that said Letters Patent is hereby corrected as shown below:

<u>Title page,</u>
Item [75], Inventors, delete "Nigel Robert Arnold Beeley, Solana Beach, CA (US)" and insert -- Andrew A. Young, Rancho Santa Fe, CA (US) --.

<u>Column 188,</u>
Lines 26-58, delete from "61. A method for reducing food intake" and ending with "and a cholecystokinin (CCK).".

Signed and Sealed this

Twenty-fifth Day of April, 2006

JON W. DUDAS
*Director of the United States Patent and Trademark Office*

UNITED STATES PATENT AND TRADEMARK OFFICE
CERTIFICATE OF CORRECTION

PATENT NO. : 6,956,026 B2
APPLICATION NO. : 09/003869
DATED : October 18, 2005
INVENTOR(S) : Beeley et al.

It is certified that error appears in the above-identified patent and that said Letters Patent is hereby corrected as shown below:

Column 188, Line 28, delete "lower a plasma lipid level" and replace with --reduce food intake--.

Column 188, Line 44, delete "lower a plasma lipid level" and replace with --reduce appetite--.

Signed and Sealed this

Fourth Day of November, 2008

JON W. DUDAS
*Director of the United States Patent and Trademark Office*